US011623025B2

(12) United States Patent
Shefi et al.

(10) Patent No.: US 11,623,025 B2
(45) Date of Patent: Apr. 11, 2023

(54) METHODS AND KITS FOR GUIDING GROWTH OF CELLS OR CELL COMPONENTS AND USES THEREOF IN TISSUE REPAIR

(71) Applicant: BAR ILAN UNIVERSITY, Ramat Gan (IL)

(72) Inventors: Orit Shefi, Rosh HaAyin (IL); Merav Antman-Passig, Petach Tiqva (IL)

(73) Assignee: BAR ILAN UNIVERSITY, Ramat Gan (IL)

( * ) Notice: Subject to any disclaimer, the term of this patent is extended or adjusted under 35 U.S.C. 154(b) by 439 days.

(21) Appl. No.: 16/078,413

(22) PCT Filed: Feb. 23, 2017

(86) PCT No.: PCT/IL2017/050235

§ 371 (c)(1),
(2) Date: Aug. 21, 2018

(87) PCT Pub. No.: WO2017/145163

PCT Pub. Date: Aug. 31, 2017

(65) Prior Publication Data

US 2019/0046692 A1 Feb. 14, 2019

Related U.S. Application Data

(60) Provisional application No. 62/298,474, filed on Feb. 23, 2016.

(51) Int. Cl.

| | |
|---|---|
| ***A61K 38/39*** | (2006.01) |
| ***A61K 35/30*** | (2015.01) |
| ***A61K 35/36*** | (2015.01) |
| ***C12N 5/071*** | (2010.01) |
| ***C12N 5/0793*** | (2010.01) |
| ***A61K 41/00*** | (2020.01) |
| ***A61K 33/24*** | (2019.01) |
| ***A61L 27/38*** | (2006.01) |
| ***A61K 38/18*** | (2006.01) |
| ***A61L 27/04*** | (2006.01) |
| ***A61L 27/24*** | (2006.01) |
| ***A61L 27/50*** | (2006.01) |
| ***A61L 27/52*** | (2006.01) |
| ***A61L 27/54*** | (2006.01) |
| ***A61L 27/58*** | (2006.01) |
| ***A61L 27/60*** | (2006.01) |
| *B82Y 5/00* | (2011.01) |

(52) U.S. Cl.

CPC .......... *A61L 27/3895* (2013.01); *A61K 35/30* (2013.01); *A61K 35/36* (2013.01); *A61K 38/185* (2013.01); *A61K 38/39* (2013.01); *A61K 41/00* (2013.01); *A61L 27/047* (2013.01); *A61L 27/24* (2013.01); *A61L 27/38* (2013.01); *A61L 27/383* (2013.01); *A61L 27/3813* (2013.01); *A61L 27/50* (2013.01); *A61L 27/52* (2013.01); *A61L 27/54* (2013.01); *A61L 27/58* (2013.01); *A61L 27/60* (2013.01); *C12N 5/0619* (2013.01); *C12N 5/0625* (2013.01); *A61K 33/24* (2013.01); *A61L 2300/414* (2013.01); *A61L 2400/06* (2013.01); *A61L 2430/32* (2013.01); *A61L 2430/34* (2013.01); *B82Y 5/00* (2013.01); *C12N 2529/00* (2013.01); *C12N 2533/54* (2013.01)

(58) Field of Classification Search

None

See application file for complete search history.

(56) References Cited

U.S. PATENT DOCUMENTS 6,057,137 A * 5/2000 Tranquillo ......... A61B 17/1128 435/174
2012/0214217 A1 8/2012 Grogan et al.

OTHER PUBLICATIONS

Shete etal, Journal of Magnetism and Magnetic Materials, 2015 (e-pub Oct. 31, 2014), vol. 377, pp. 406-410. (Year: 2015).*
Antman-Passig et al., "Remote Magnetic Orientation of 3D Collagen Hydrogels for Directed Neuronal Regeneration", Nano Letters, 2016, vol. 16, No. 4, pp. 2567-2673.
Baranes et al., "Topographic Cues of Nano-Scale Height Direct Neuronal Growth Pattern", Biotechnology and Bioengineering, 2012, vol. 109, pp. 1791-179.
Ceballos et al., "Magnetically Aligned Collagen Gel Filing a Collagen Nerve Guide Improves Peripheral Nerve Regeneration", Experimental Neurology, 1999, vol. 158, pp. 290-300.
Chen et al., "Microstructures and rheological properties of tilapia fish-scale collagen hydrogels with aligned fibrils fabricated under magnetic fields" Acta Biomaterialia, 2011, vol. 7, pp. 644-652.
Cheng et al., "An electrochemical fabrication process for the assembly of anisotropically oriented collagen bundles", Biomaterials, 2008, vol. 29, pp. 3278-3288.
Guo et al., "Flow and magnetic field induced collagen alignment", Biomaterials, 2007, vol. 28, pp. 1105-1114.
Wang et al., "Creation of highly aligned electrospun poly-L-lactic acid fibers for nerve regeneration applications", Journal of Neural Engineering, 2009, vol. 6:016001.
Huber et al., "Signaling at the growth cone: Ligand-receptor complexes and the control of axon growth and guidance", Annual Review of Neuroscience, Feb. 2003, pp. 509-563.

(Continued)

*Primary Examiner* — Allison M Fox

(74) *Attorney, Agent, or Firm* — Vorys, Safer, Seymour and Pease LLP; Anthony P. Venturino; Maryellen Feehery Hank

(57) ABSTRACT

Provided subject matter relates to tissue engineering. More specifically provided are kits, devices and methods for in situ repair and regeneration of guided and functional growth of cells and cell components by providing into the injury site biomaterial solution including the cell(s), magnetic particles and solidifying the biomaterial while applying the magnetic field.

15 Claims, 15 Drawing Sheets

Specification includes a Sequence Listing.

(56) References Cited

OTHER PUBLICATIONS

Kim et al., Independent Control of Topography for 3D Patterning of the ECM Microenvironment, Advanced Materials, 2016, vol. 28, pp. 132-137.
You et al., "Nanoengineering the Heart: Conductive Scaffolds Enhance Connexin 43 Expression", Nano Letters 2011, American Chemical Society, vol. 11, pp. 3643-3648.
Johnson et al., "3D Printed Anatomical Nerve Regeneration Pathways", Advanced Functioning Materials, 2015, vol. 25, pp. 6205-6217.
Koh et al., "Enhancement of neurite outgrowth using nano-structured scaffolds coupled with laminin", Biomaterials, 2008, vol. 29, pp. 2574-3582.
Lee et al., "Microfluidic alignment of collagen fibers for in vitro cell culture", Biomedical Microdevices, 2006, vol. 8, pp. 35-41.
Li et al., "Genomic and Morphological Changes of Neuroblastoma Cells in Response to Three-Dimensional Matrices", Tissue Engineering, 2007, vol. 13, pp. 1035-1047.
Sarig-Nadir et al., "Laser Photoablation of Guidance Microchannels into Hydrogels Directs Cell Growth in Three Dimensions", Biophysical Journal, 2009, vol. 96, pp. 4743-4752.
Schmidt et al., "Neural Tissue Engineering: Strategies for Repair and Regeneration", Annu. Rev. Biomed. Eng., 2003, vol. 5, pp. 293-347.
Shevach et al., "Nanoengineering gold particle composite fibers for cardiac tissue engineering", Journal of Materials Chemistry B, 2013, vol. 1, pp. 5210-5217.
Siemionow et al., "Current Techniques and Concepts in Peripheral Nerve Repair", International Review of Neurobiology, 2009, vol. 87, pp. 141-172.
Slaughter et al., "Hydrogels in Regenerative Medicine", Adv Mater, 2009, vol. 21, pp. 3307-3329.
Vader et al., "Strain-Induced Alignment in Collagen Gels", PLoS ONE, 2009, vol. 4, Issue 6, e5902.
Xie et al., "Noninvasive Neuron Pinning with Nanopillar Arrays", Nano Letters, 2010, vol. 10, pp. 4020-4024.
Yang et al., "Electrospinning of nano/micro scale poly(L-lactic acid) aligned fibers and their potential in neural tissue engineering". Biomaterials, 2005, vol. 26, pp. 2603-2610.
Yao et al., "Orienting Neurite Growth in Electrospun Fibrous Neural Conduits", Journal of Biomedical Materials Research Part B: Applied Biomaterials, 2009, vol. 90, pp. 483-491.
Zrinyi, "Intelligent polymer gels controlled by magnetic fields", Colloid Polym Sci, 2000, vol. 278, pp. 98-103.

* cited by examiner

Fig. 1A
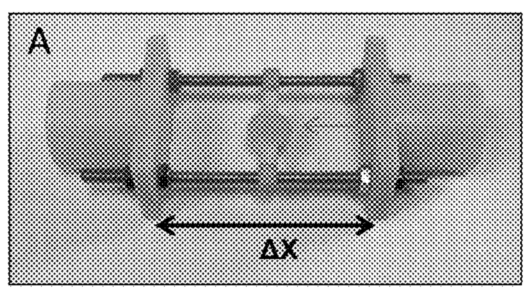
Fig. 1B
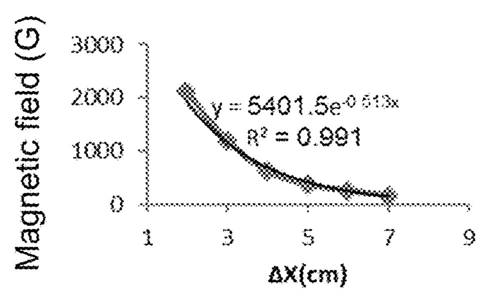
Fig. 2A
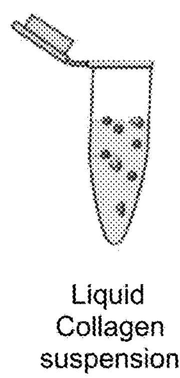
Fig. 2B
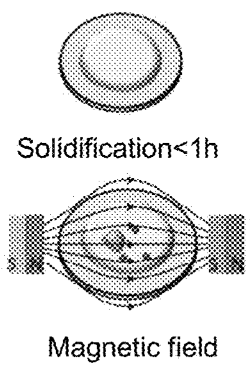
Fig. 2C
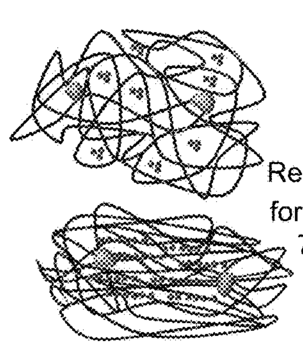
Fig. 2D
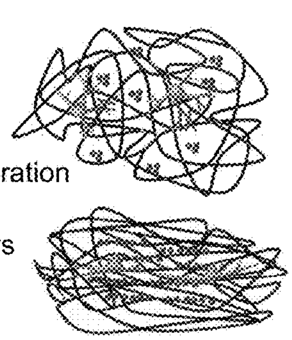
Fig. 3A
Fig. 3B
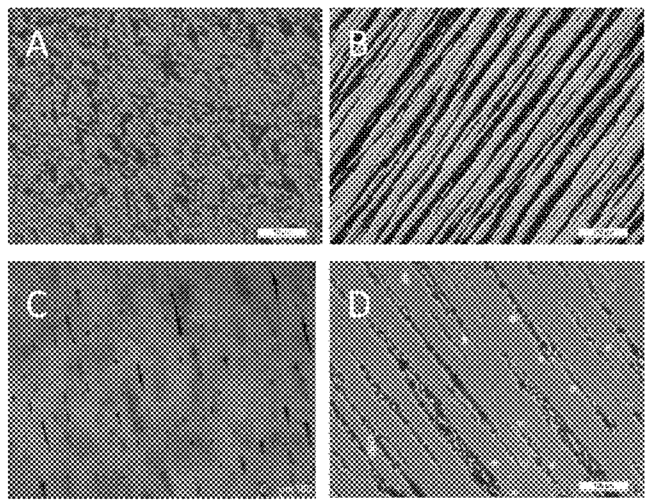
Fig. 3C
Fig. 3D Fig. 4A Fig. 4B
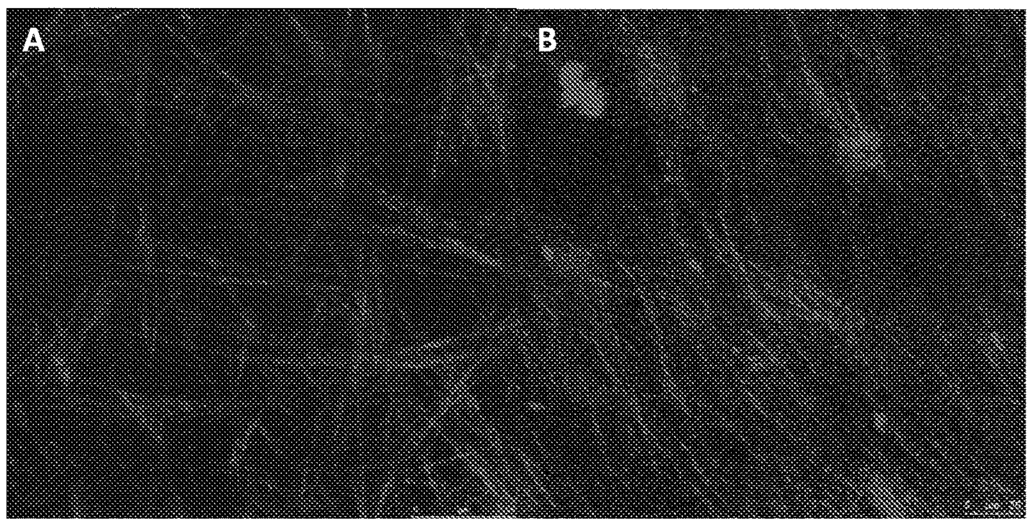
Fig. 5A Fig. 5B Fig. 5C
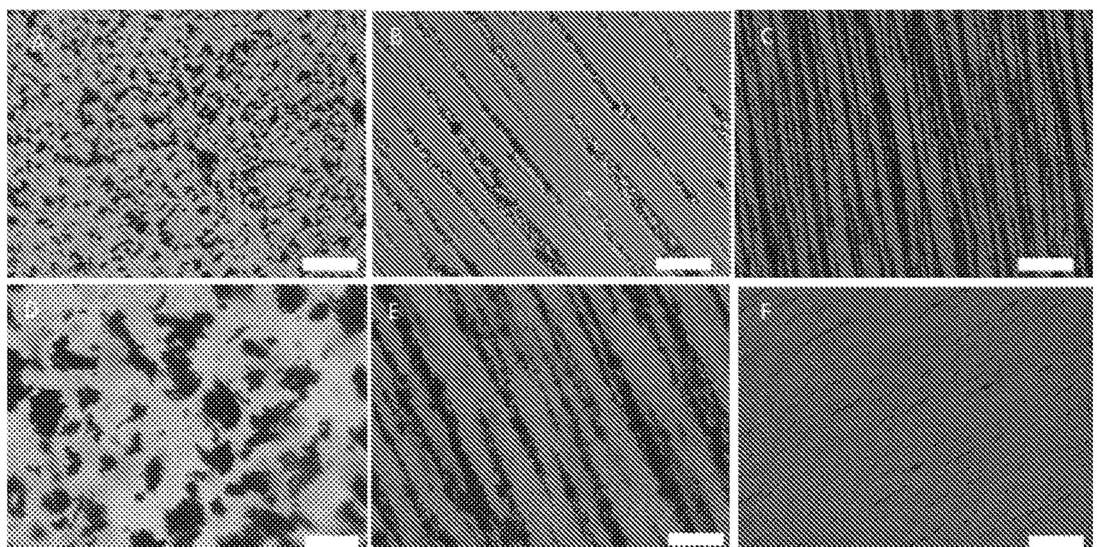
Fig. 5D Fig. 5E Fig. 5F
Fig. 6A Fig. 6B Fig. 6C Fig. 6D
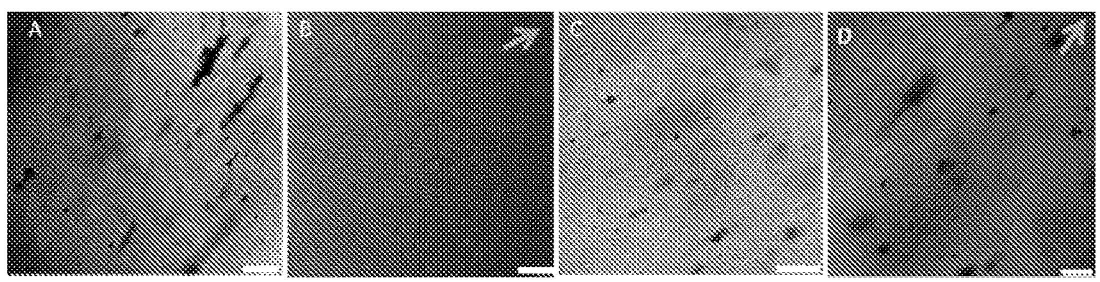

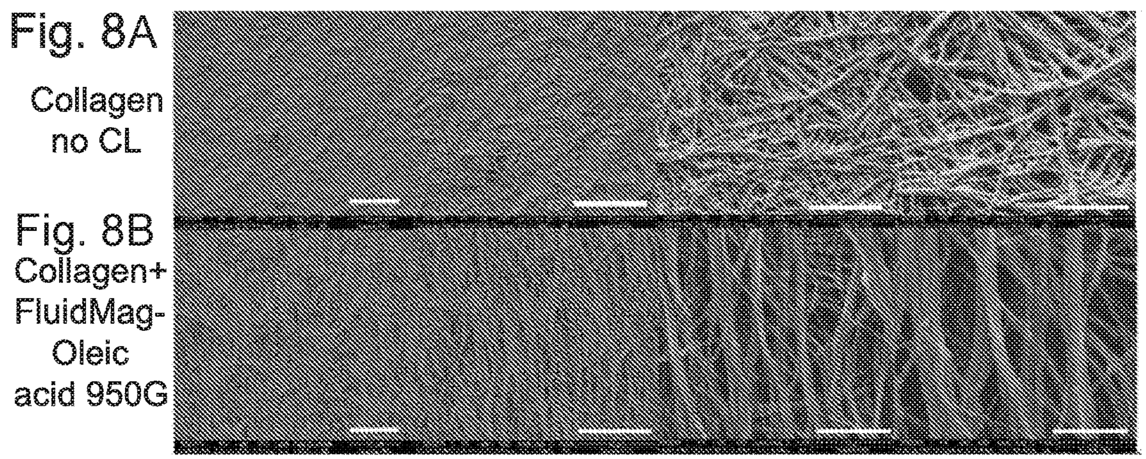
Fig. 8A
Collagen no CL
Fig. 8B
Collagen+ FluidMag-Oleic acid 950G
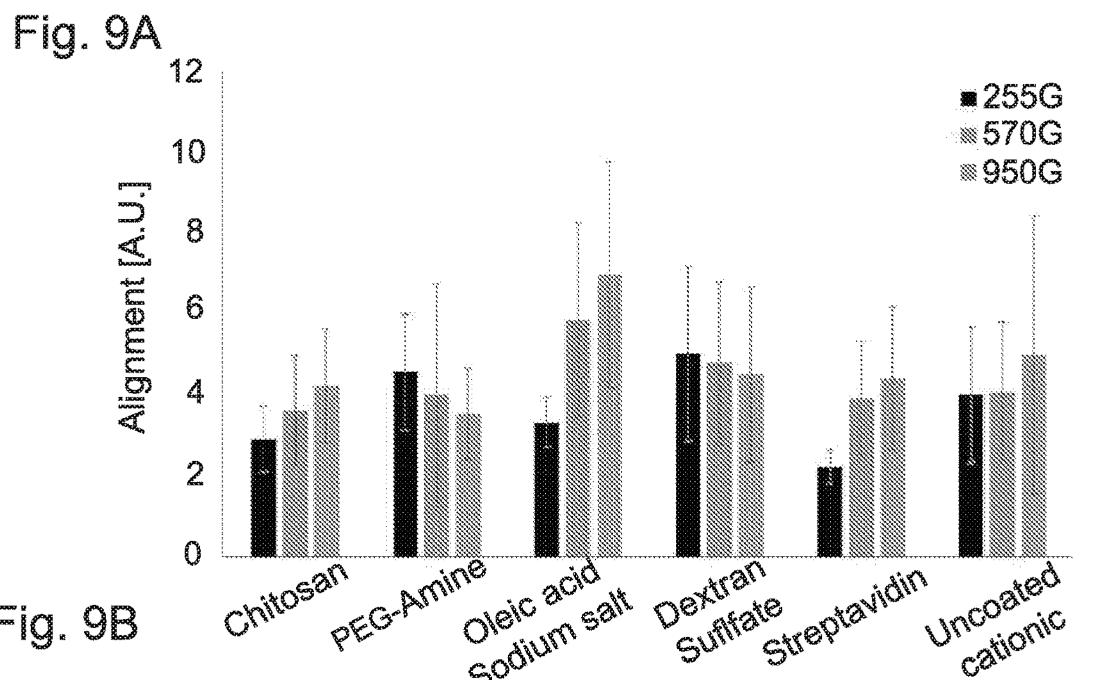
Fig. 9A
255G
570G
950G
Alignment [A.U.]
12
10
8
6
4
2
0
Chitosan
PEG-Amine
Oleic acid Sodium salt
Dextran Suflfate
Streptavidin
Uncoated cationic
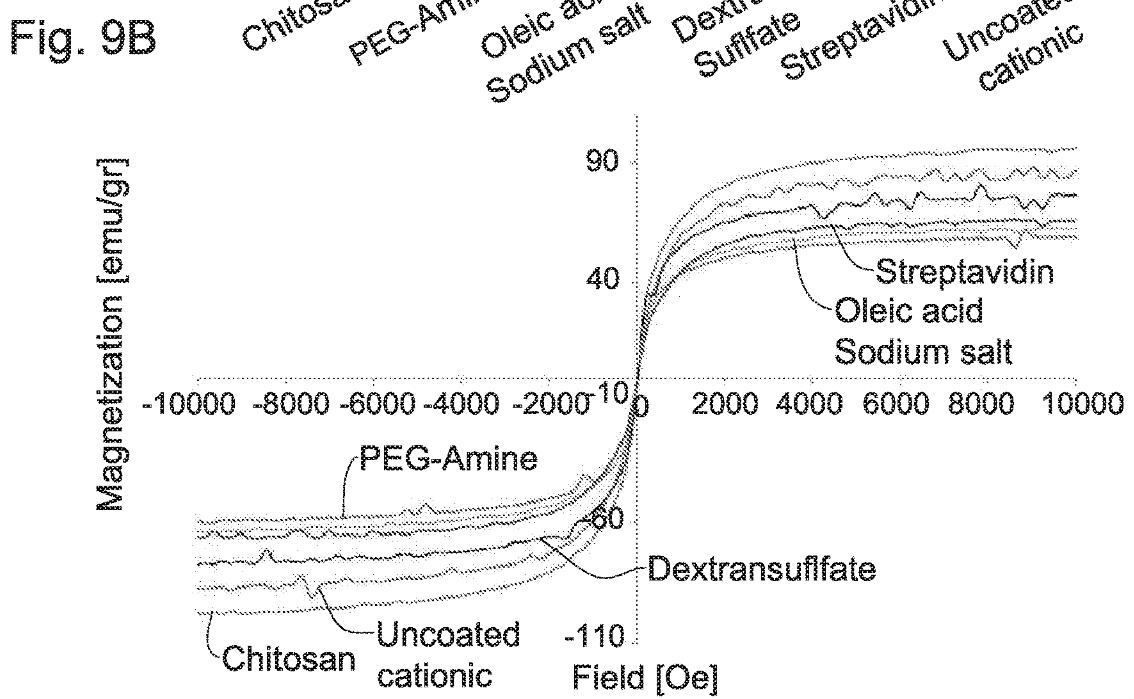
Fig. 9B
Magnetization [emu/gr]
90
40
-10
-60
-110
-10000 -8000 -6000 -4000 -2000 0 2000 4000 6000 8000 10000
Field [Oe]
Streptavidin
Oleic acid Sodium salt
PEG-Amine
Dextransuflfate
Uncoated cationic
Chitosan Fig. 10A
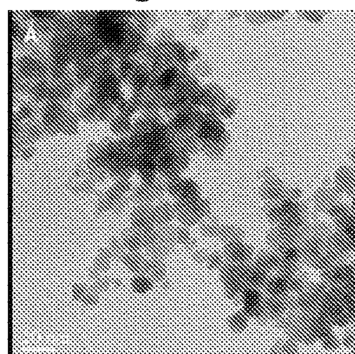
Fig. 10B
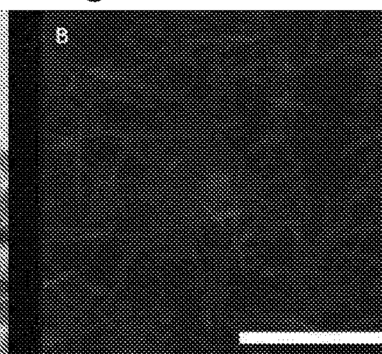
Fig. 10C
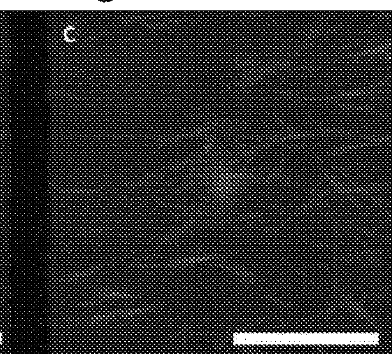
Fig. 11A
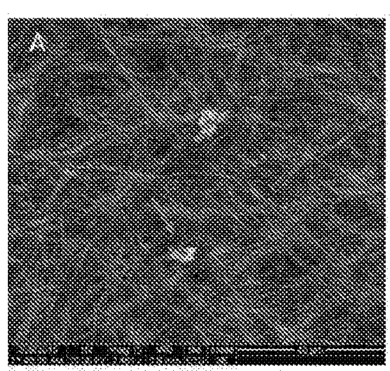
Fig. 11B
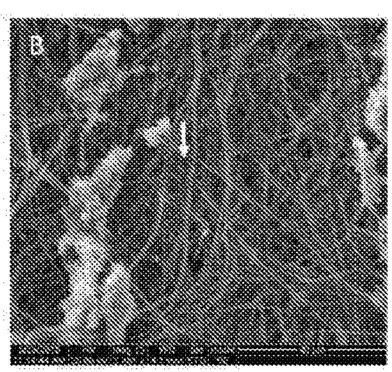
Fig. 11C
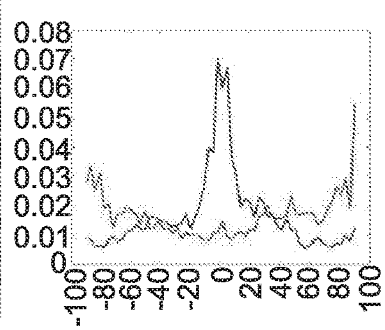
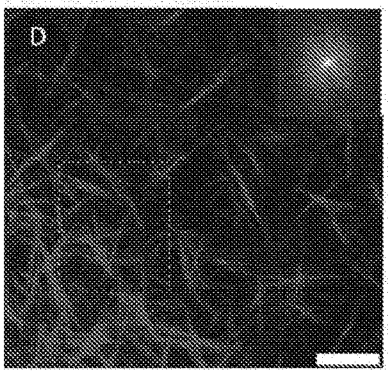
Fig. 11D
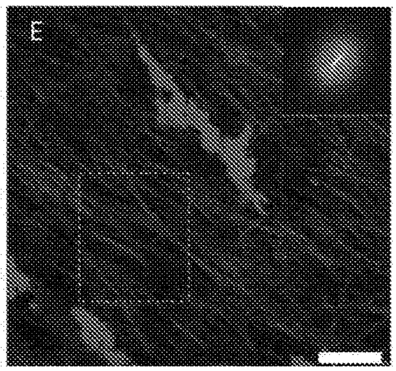
Fig. 11E
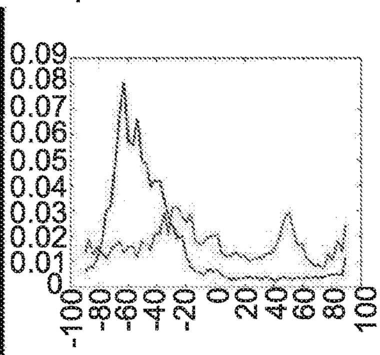
Fig. 11F Fig. 12A
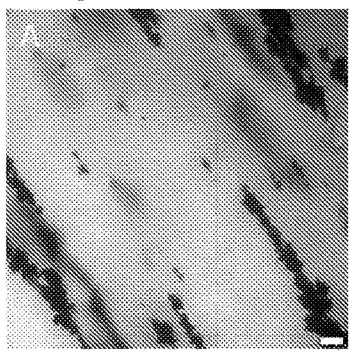
Fig. 12B
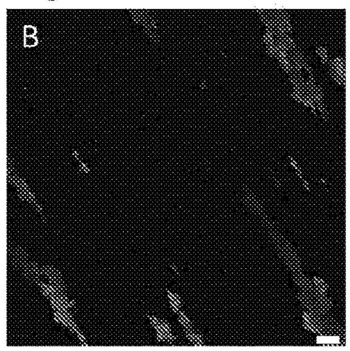
Fig. 12C
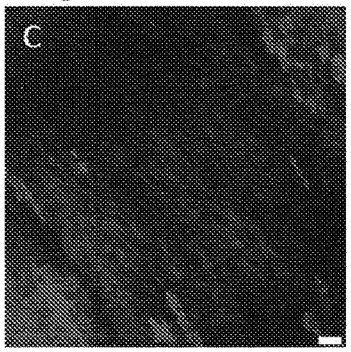
Fig. 12D
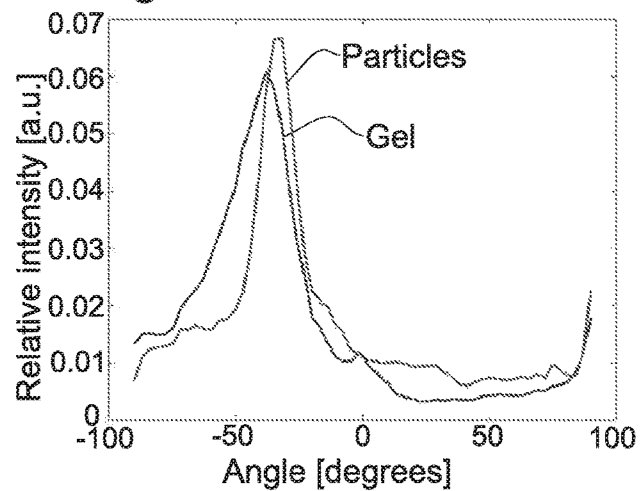
Fig. 12E
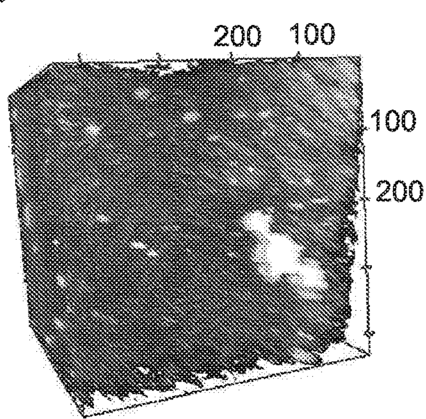
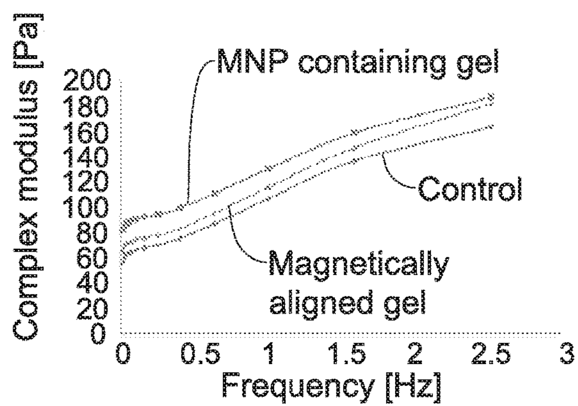
Fig. 13A
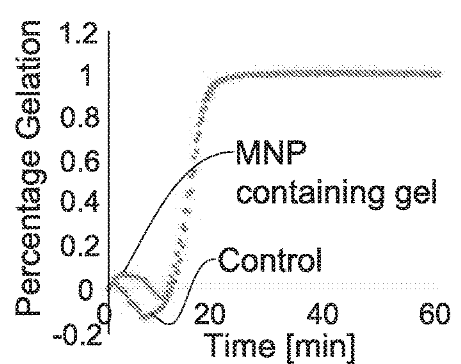
Fig. 13B

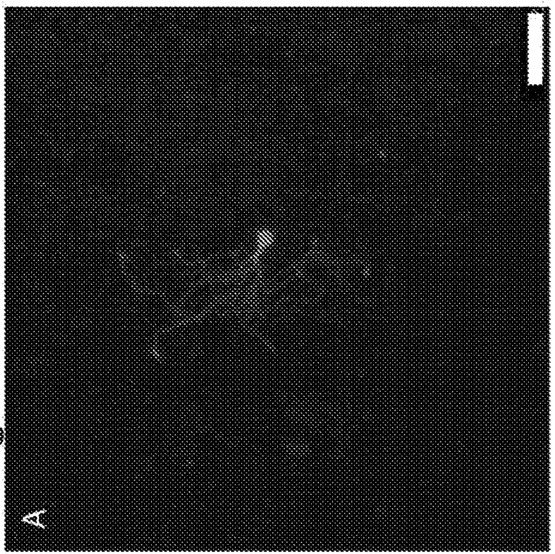
Fig. 16A
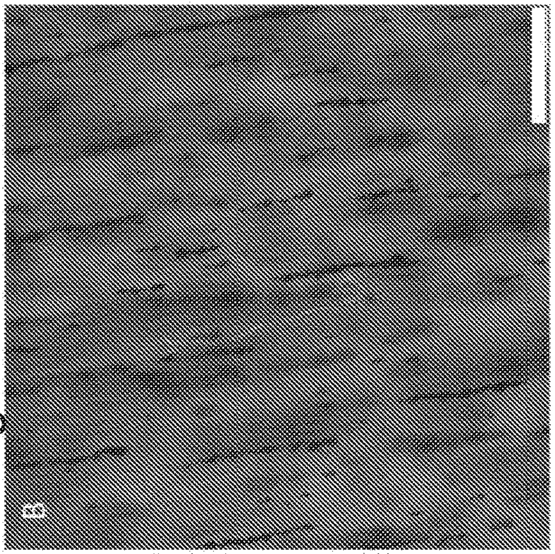
Fig. 16B
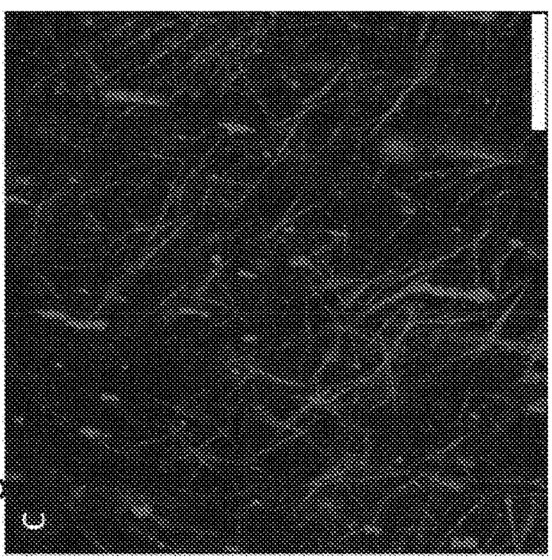
Fig. 16C
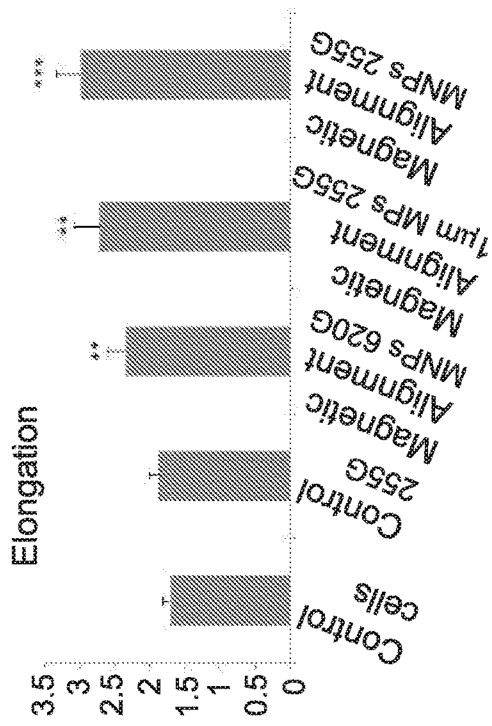
Fig. 16D
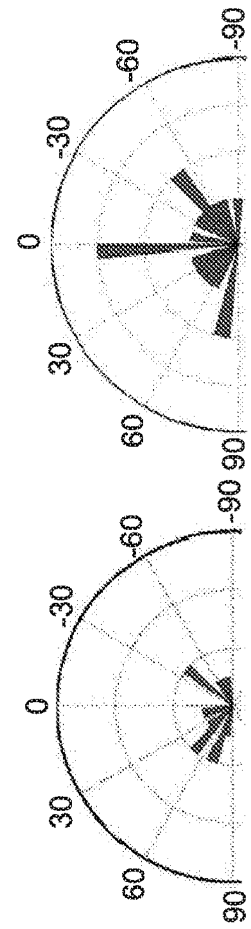
Fig. 16E
Fig. 16F Fig. 17A
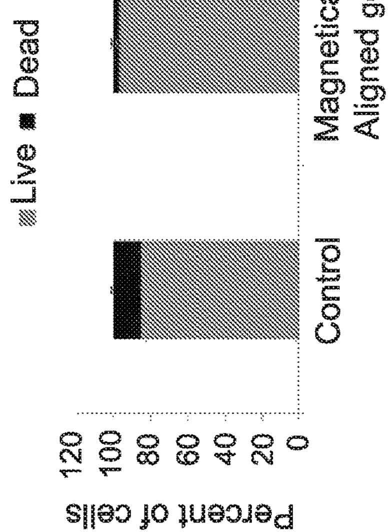
Fig. 17B
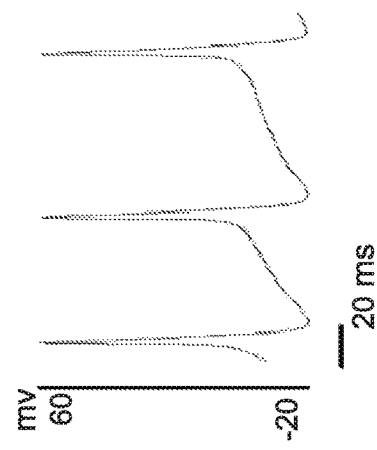
Fig. 17C
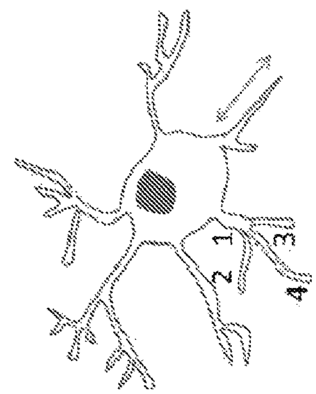
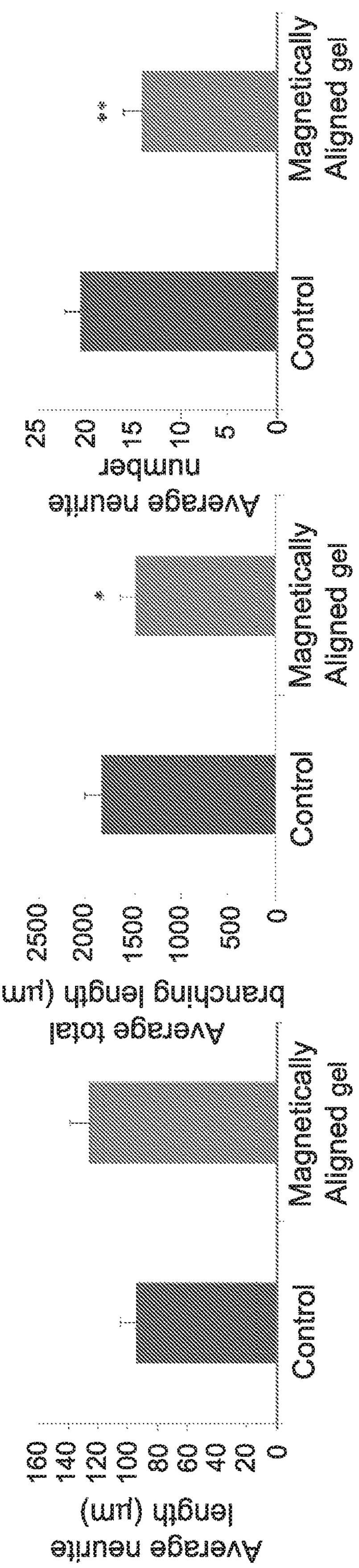
Fig. 17D
Fig. 17E
Fig. 17F Fig. 18A
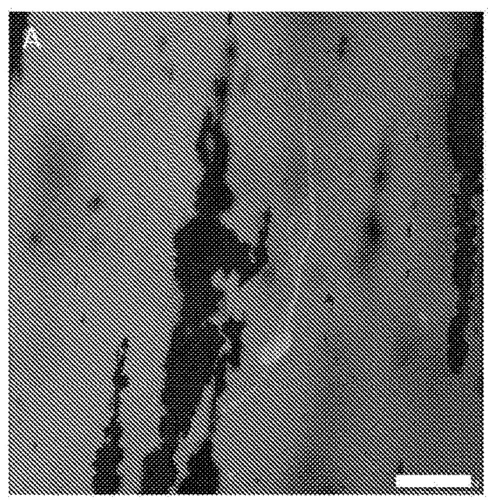
Fig. 18B
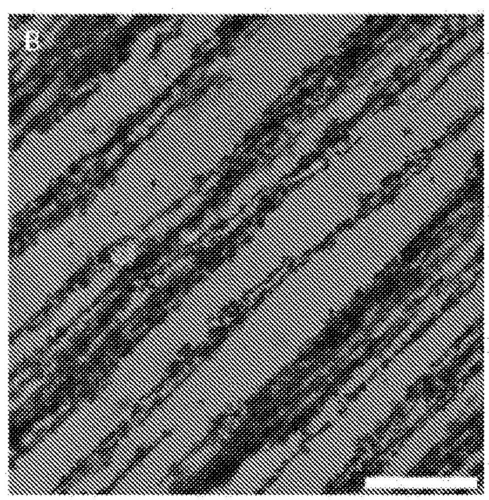
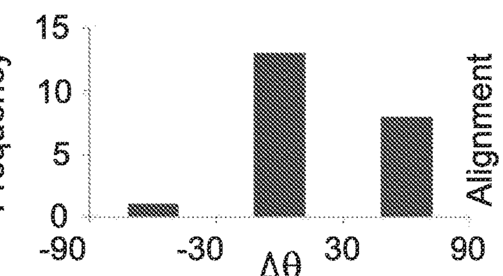
Fig. 18C
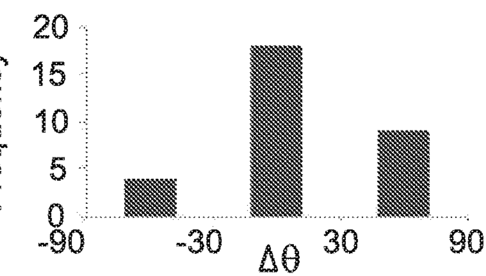
Fig. 18D
Fig. 19A
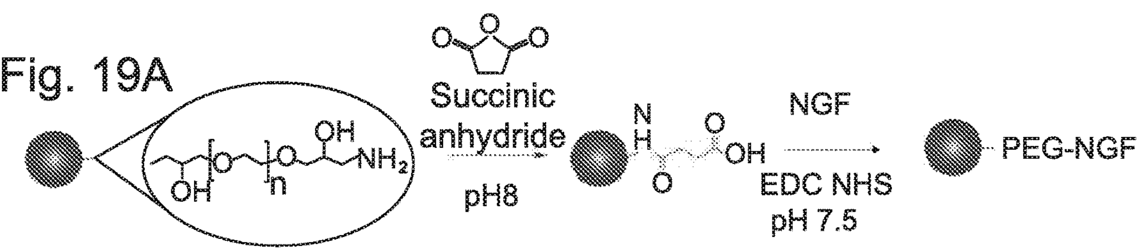
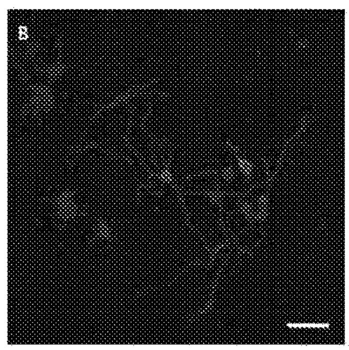
Fig. 19B
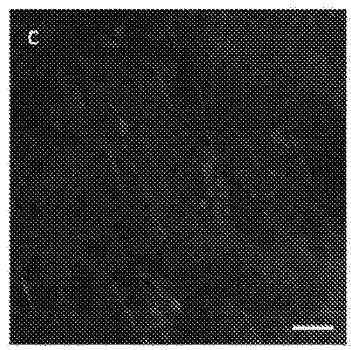
Fig. 19C
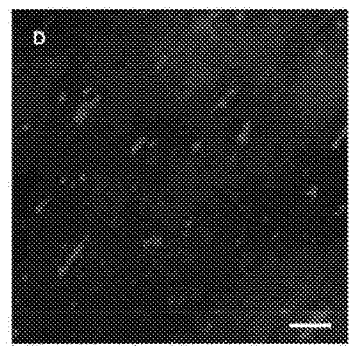
Fig. 19D

METHODS AND KITS FOR GUIDING GROWTH OF CELLS OR CELL COMPONENTS AND USES THEREOF IN TISSUE REPAIR

SEQUENCE LISTING

The Sequence Listing submitted in text format (.txt) filed on Aug. 22, 2018, named "SequenceListing.txt", created on Aug. 20, 2018 (38.5 KB), is incorporated herein by reference.

FIELD OF THE INVENTION

The present invention relates to tissue engineering. More specifically the invention provides kits, devices and methods for in situ repair and regeneration of guided and functional growth of cells and cell components.

BACKGROUND ART

References considered to be relevant as background to the presently disclosed subject matter are listed below:

[1] Slaughter B V et al., Adv. Mater. 21: 3307-3329 (2009).
[2] Siemionow M et al., Int. Rev. Neurobiol. 87:141-172 (2009).
[3] Schmidt C E et al., Annu. Rev. Biomed. Eng. 5: 293-347 (2003).
[4] Huber A B et al., Annu. Rev. Neurosci. 26:509-563 (2003).
[5] Xie C et al., Nano Lett. 10: 4020-4024 (2010).
[6] Baranes K et al., Biotechnol. Bioeng. 109:1791-1797 (2012).
[7] Johnson B N et al., Adv. Funct. Mater. 25: 6205 (2015).
[8] Han Bing, W et al., Neural. Eng. 6:016001 (2009).
[9] Li G N et al., Tissue Eng. 13:1035-1047 (2007).
[10] Yang F et al., Biomaterials 26: 2603-2610 (2005).
[11] Lee P et al., Biomed. Microdevices 8:35-41 (2006).
[12] Vader D et al., PloS one 4:e5902 (2009).
[13] Sarig-Nadir O et al. Biophys. J. 96: 4743-4752 (2009).
[14] Xingguo Cheng et al., Biomaterials 29: 3278-3288 (2008).
[15] Ceballos D et al., Exp. Neurol. 158: 290-300 (1999).
[16] Chen S et al., Acta Biomaterialia 7: 644-652 (2001).
[17] Gue C and Kaufman L. Biomaterials 28: 1105-1114 (2007).
[18] Yao L et al., J. Biomed. Mater. Res. 90(B): 483-491 (2009).
[19] Koh, H et al., Biomaterials 29: 3574-3582 (2008).
[20] You J O et al., Nano Lett. 11 (9): 3643-3648 (2011).
[21] Shevach M. et al., J. Mater. Chem. B. 1(39): 5210-5217 (2013).

BACKGROUND OF THE INVENTION

Hydrogel biomaterials, due to their unique biocompatibility, flexible methods of synthesis, range of constituents, and desirable physical characteristics, have been the material of choice for many applications in regenerative medicine. Hydrogels are particularly attractive scaffolding material because their mechanical properties can be tailored to mimic those of natural tissues. As scaffolds, hydrogels are used to provide bulk and mechanical constitution to a tissue construct, whether cells are adhered to or suspended within the 3D gel framework [1]. Neural tissue pathologies resulting from either physical trauma or neurodegenerative diseases detrimentally affect the quality of life of many patients worldwide. The ability of mammalian neuronal cells to spontaneously repair and regain functionality is limited, presenting a critical therapeutic challenge for researchers [2]. Major efforts have been devoted to the development of supportive tissues and scaffolds, aimed at creating modified environments for promoting neuronal regeneration. It has been shown that guiding and directing neuronal outgrowth during the regeneration period can enhance neuronal repair and recovery [3].

A fundamental mechanism of neuronal guidance is the sensitivity of neurons to extracellular topography [4]. Previous studies have shown that interactions with planar surfaces decorated with organized topographical elements even of nanometer heights lead to directed neuronal growth patterns [5,6]. However, in order to develop a supportive microenvironment for neuronal regeneration in vivo, implantable 3-dimensional scaffolds are required [7]. Various strategies, utilizing nanofibrous scaffolds [8] as well as different types of hydrogels [1, 9] have been examined as platforms for neuronal tissue engineering affecting axonal extension and cell spreading. Several methods have been used to fabricate scaffolds with aligned fibrils as cell-directing cues including electorspinning [10] microfluidics [11], strain-induced alignment [12], fabrication of prescribed patterns within the 3D constructs [13] and electrochemical alignment by application of electric currents [14]. Strong magnetic fields have also been used to modify fiber orientation [15, 16]. In all of these studies scaffolds were designed and fabricated ex vivo, prior to the interaction with the cells or implantation site. Attempt of in situ scaffold preparation were made by Gue and Kaufman describing the alignment of 2D and 3D collagen gels using streptavidin coated micro-magnetic beads and a small magnet, both in plain and cell-bearing gels. In most cases, the micro-beads were pulled-out of the gel [17]. However, an in situ alignment by solidifying cell bearing gels forming a functional scaffold that is specifically adjusted to the injured tissue, has not been disclosed by the prior art.

Similarly, recent studies have focused on controlling micro structures, orientation of scaffolds and properties, including of hydrogels, for tissue engineering and enhanced regeneration [18, 19]. Embedding metallic nanometric elements has been found to be effective in promoting cell-scaffold interactions affecting growth as well as the activity of excitable membrane cells [18, 20, 21]. Usually, these methods require ex-vivo manipulations prior to implantation. The ability to implant a scaffold directly into the injured site, then manipulating its orientation according to the pathological need, is still a therapeutic challenge.

There is therefore need in the art to provide novel biomaterial scaffolds and dynamic methods capable of guiding growth of cells or cell components in a body site.

SUMMARY OF THE INVENTION

In a first aspect, the invention provides a method for guiding growth of a cell, a mixture of cells, plurality of cells, or cell component/s. More specifically, the method of the invention may comprise the following steps:

In a first step (a), providing at least one liquid biomaterial or biomaterial solution, comprising the cell/s, plurality of cells, or mixture of cells and magnetic particles or any conjugate, mixture, embedment and encasement thereof or any composition or matrix comprising the same. In the next step (b), providing at least one or at least two magnetic sources placed at a distance providing a magnetic field having a strength of between about 5 G to about 5000 G. The next step (c), involves solidifying the biomaterial while applying the magnetic field, thereby aligning along the magnetic field lines, at least one of the magnetic particles or aggregates thereof and components of the biomaterial. The method of the invention may comprise a further step of removing the magnetic sources once the biomaterial is solid. In the next step (d), allowing cell growth within the solidified biomaterial obtained in step (c), thereby guiding the growth of the cells or cell components longitudinally oriented along at least one of the aligned magnetic particles or aggregates thereof and the aligned components of the biomaterial.

In yet a further aspect, the invention relates to a method of treating or repairing tissue or organ injury in a subject. More specifically, the method of the invention may comprise the steps of: (a) providing into the site of the injured tissue or organ, at least one liquid biomaterial or biomaterial solution comprising cell/s, plurality of cells, or mixture of cells and magnetic particles or any conjugate, mixture, embedment and encasement thereof or any composition or matrix comprising the same. Next, in step (b), providing at least one or at least two magnetic sources placed at a distance providing a magnetic field having a strength of between about 5 G to about 5000 G. The next step (c) involves in situ solidifying the biomaterial while applying the magnetic field. Solidifying the biomaterial under magnetic field provides the alignment of at least one of the magnetic particles or aggregates thereof and/or components of the biomaterial along the magnetic field lines. In the next step (d), allowing growth of cells or cell component/s within the solidified biomaterial.

In yet a further aspects, the invention provides a method of promoting wound healing in a subject.

In another aspect, the invention provides a kit or system comprising: (a) at least one liquid biomaterial or biomaterial solution comprising cell/s, or mixture of cells and magnetic particles or any conjugate, mixture, embedment and encasement thereof or any composition or matrix comprising the same; and (b) at least one or at least two magnetic sources providing a magnetic field having a strength of between about 5 G to about 5000 G.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiment of the invention will become apparent by the hand of the following figures.

BRIEF DESCRIPTION OF THE FIGURES

FIG. 1A-1B. Magnetic actuation set up for in vitro experiment

FIG. 1A. shows an image of magnetic actuation set up. Collagen gel solution placed on the portable stage (one-head grey arrow) allowed to solidify under the influence of the magnetic field emitted by the magnets placed in the plastic holders. Magnetic field strength is adjusted via moving the holders.

FIG. 1B. shows magnetic field strength as a function of distance from stage.

FIG. 2A-2D. Schematic overview of the experimental procedure showing collagen fiber alignment induced by magnetic particles and magnetic actuation FIG. 2A. Liquid collagen suspension was prepared containing neurons (random shape) and magnetic particles (MPs, dark circles).

FIG. 2B. Suspension was plated on top of cover slips and allowed to solidify either spontaneously (top), or under the influence of a magnetic field of 255 G set by two parallel bar magnets (indicated as S/N bars) (bottom).

FIG. 2C. Zoom into collagen gels. Control gel reveals random distribution of MNP aggregates (dark circles) and random collagen fiber orientation (light grey lines) (Top). In gels solidified under the influence of a magnetic field MPs form aggregate strings aligned along the direction of the magnetic lines (dark circles) and collagen fibers align as well (light grey lines) (Bottom).

FIG. 2D. Neuronal growth was followed for 7 days as neurons developed neurits in the direction of the magnetically-aligned cues.

FIG. 3A-3D. Tunability of magnetic particle alignment

FIG. 3A. shows 1.5 mg/mL collagen gel containing SiMag particles (3 μm) under no magnetic field.

FIG. 3B. shows 1.5 mg/mL collagen gel containing SiMag particles (3 μm) under 1120 G.

FIG. 3C. shows 3 mg/mL collagen gel containing SiMag particles (3 μm) under 255 G (gray arrows indicate magnetic particles in different planes).

FIG. 3D. shows 1.5 mg/mL collagen gel containing Mag/R-DXS 150 nm under 255 G magnetic field.

FIG. 4A-4B. Confocal reflectance images

FIG. 4A. shows confocal reflectance images of a control gel.

FIG. 4B. shows confocal reflectance images of a gel containing MAG/R-UC Magnetite core 100 nm which was solidified under 255 G, resulting in oriented collagen fibers.

FIG. 5A-5F. Formation of aligned magnetic particle strings within the collagen gels Two gel concentrations were examined: 1.4 mg/mL (top panels, FIGS. 5A, 5B, 5C) and 3 mg/mL (bottom panels, FIGS. 5D, 5E, 5F). The effect of one magnetic field is presented (255 G).

FIG. 5A. shows MPs (1 μm) mixed into collagen gels (1.4 mg/mL) and solidified with no magnetic field that form random aggregates distributed homogenously in the gel.

FIG. 5B. shows 100 nm MNPs that form magnetic strings in collagen gels (1.4 mg/mL) solidified in the presence of a magnetic field (255 G).

FIG. 5C. shows 1 μm MPs that form magnetic strings in collagen gels (1.4 mg/mL), that have solidified in the presence of a magnetic field.

FIG. 5D. shows MNPs (100 nm) mixed into collagen gels (3 mg/mL) and solidified with no magnetic field. Aggregates are formed and distributed randomly (lighter aggregates are out of phase aggregates).

FIG. 5E. shows magnetic strings that were formed in gels (3 mg/mL) containing MNPs (100 nm), solidified in the presence of a magnetic field.

FIG. 5F. shows 1 μm MPs that form magnetic strings in gels (3 mg/mL) solidified in the presence of a magnetic field. Scale bar=100 μm.

FIG. 6A-6D. Phase images of collagen fibers in different gel complexes demonstrate non-aligned and aligned distribution of fibers Gels of 3 mg/mL containing different MNPs were solidified under the influence of 255 G at 25° C. Gels were imaged after solidification. Magnetic field direction for each image is indicated with a grey arrow.

FIG. 6A. Gel containing 100 nm MNPs coated with Dextransulfate (MAG/R-DXS)

FIG. 6B. Gel containing 100 nm MNPs coated with Starch (MAG/R-D). Here, MNPs do not form visible magnetic strings.

FIG. 6C. Gel with uncoated 50 nm MNPs (fluidMAG-UC/C).

FIG. 6D. Gel containing 100 nm uncoated particles (fluidMag-UC/C) shows directed orientation of fibers. Scale bar=50 μm.

Figure 7:
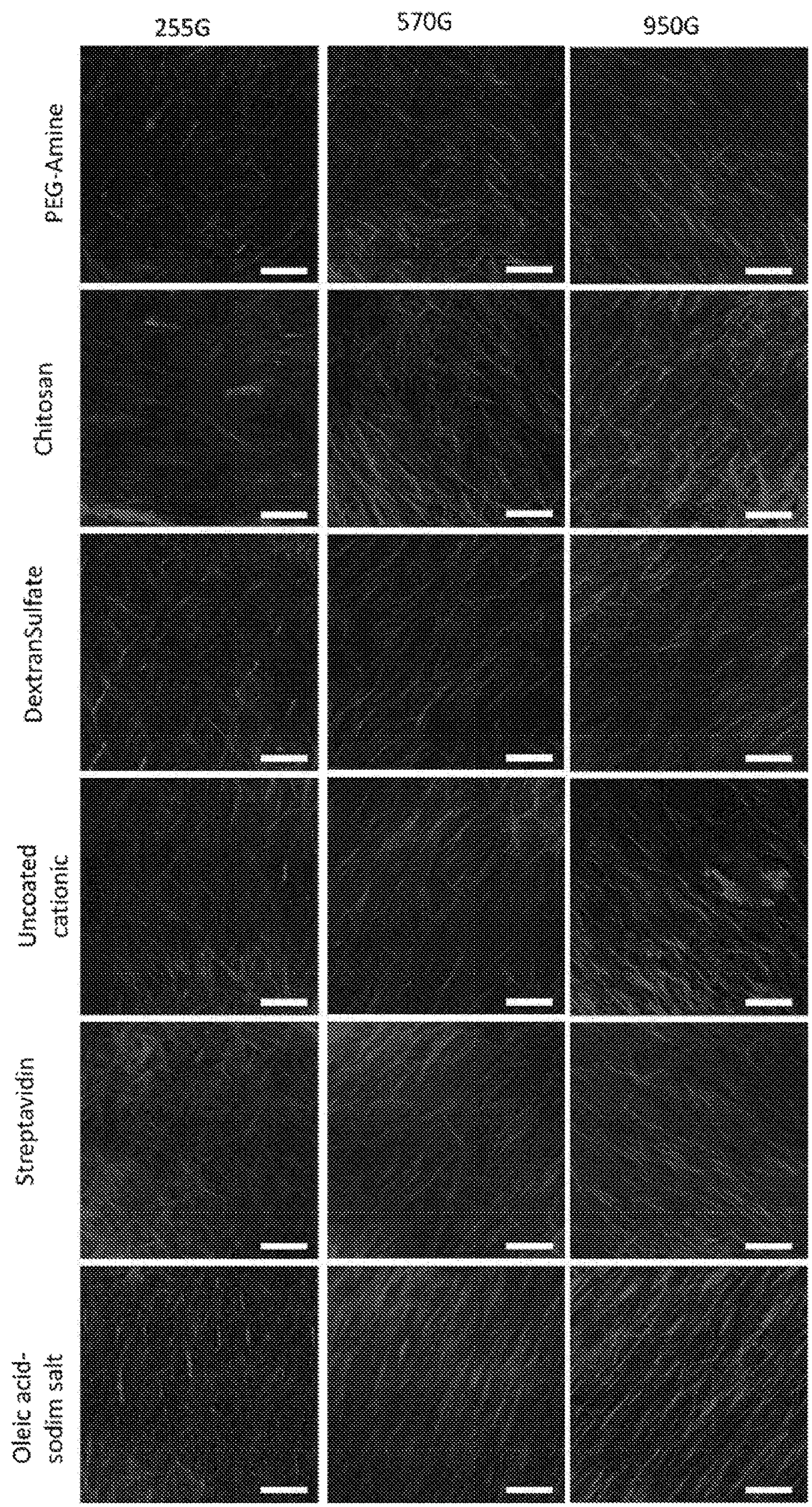
FIG. 7. Effect of different MNPs in different magnetic field strength

Sample confocal reflectance images of magnetically aligned gels, with various MNPs and magnetic fields. Scale bar=100 μm.

FIG. 8A-8B. SEM images of Aligned collagen fibers

FIG. 8A. Control 3 mg/mL collagen gels, without MNPs or magnetic fields (Upper panel).

FIG. 8B. Collagen gels magnetically oriented via incorporation of Oleic acid sodium salt MNPs and solidified under 950 G. scale bar from left to right 50, 40, 10, 5 μm (Lower panel).

FIG. 9A-9B. Effect of MNP coating on collagen alignment.

FIG. 9A. Normalized FFT analysis of CRM images

FIG. 9B. SQUID analysis of MNPs

FIG. 10A-10C. iron oxide nanoparticles effect on collagen fiber alignment.

FIG. 10A. TEM image of Iron oxide nanoparticles synthesized by co-precipitation.

FIG. 10B. Control collagen gel (3 mg/mL)

FIG. 10C. Collagen gel (3 mg/mL) containing iron oxide nanoparticles solidified under 570 G. scale bar=100 μm FIG. 11A-11F. Collagen fiber alignment induced by magnetic string formation FIG. 11A. SEM image of collagen gel (3 mg/mL) containing 100 nm MNPs showing random fiber orientation.

FIG. 11B. SEM image of the same collagen gel solidified under the influence of 255 G magnetic field, showing partial alignment of collagen fibers (white arrow) correlating to magnetic aggregate string direction (grey arrows).

FIG. 11C. FFT analysis plot showing fiber orientation corresponding to indent depicted area in image B in black (no particles are included within the analyzed area) compared to image A in grey.

FIG. 11D. CRM image of collagen gel (3 mg/mL) solidified under the influence of 255 G magnetic field without MNPs. FFT analysis images for the area depicted in shown in corresponding top right corner.

FIG. 11E. CRM image of the 3 mg/mL collagen gel containing 100 nm MNPs solidified under the influence of 255 G magnetic field, showing fiber alignment. FFT analysis images for the area depicted in FIG. 11D and FIG. 11E and shown in corresponding top right corner.

FIG. 11F. FFT analysis plot of same depicted areas in D (black) and E (grey).

Scale bar=75 μm.

FIG. 12A-12E. Collagen fiber alignment

FIG. 12A. Phase image of a collagen gel embedded with MNPs after solidification under magnetic field (255 G).

FIG. 12B. Confocal image of fluorescently labeled particles of the same image as in A. MNPs are in light gray.

FIG. 12C. CRM image of the same gel demonstrating induced alignment of collagen fibers.

FIG. 12D. FFT plot of the magnetic strings (light gray, corresponding to image B) and collagen fibers (dark gray, corresponding to image C), showing high resemblance in maximal peak.

FIG. 12E. 3D reconstruction of collagen fibers of magnetically aligned gel.

Scale bar=50 μm.

FIG. 13A-13B. Measurements of physical properties of magnetically MNPs containing gels FIG. 13A. Rheometry measurements of complex modulus curves for control gels, with or without particles, solidified under the presence of magnetic field, compared to magnetically aligned gels.

FIG. 13B. Turbidity measurements of gelation kinetics for gels with and without MNPs.

FIG. 14A-14D. Neuronal orientation in magnetically aligned gels

Figure 14A:
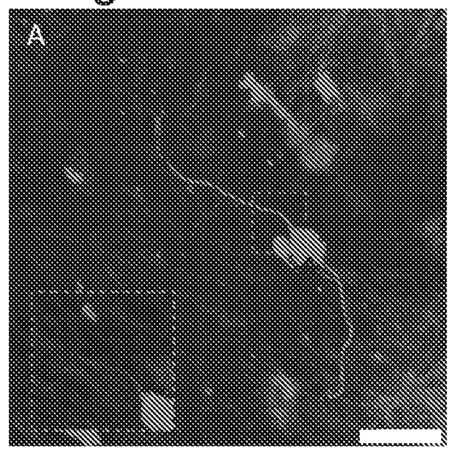

FIG. 14A. Confocal z-stack image of a leech neuron grown in a magnetically aligned gel (3 mg/mL, MNPs of 100 nm, a magnetic field of 255 G). Neuron is fluorescently labeled. Background is a single CRM image from stack, showing fiber alignment. Indent shows neurite following aligned collagen fibers.

Figure 14B:
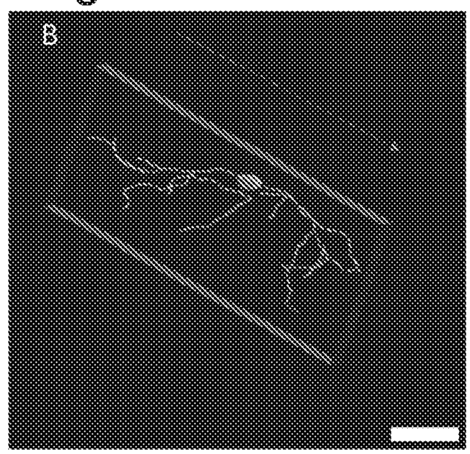

FIG. 14B. Corresponding 3D cuboid representation of the neuron with neurite tracing analysis. The long axis of the cuboid represents the direction of growth. Red arrow represents the orientation of the magnetic particle strings.

Figure 14C:
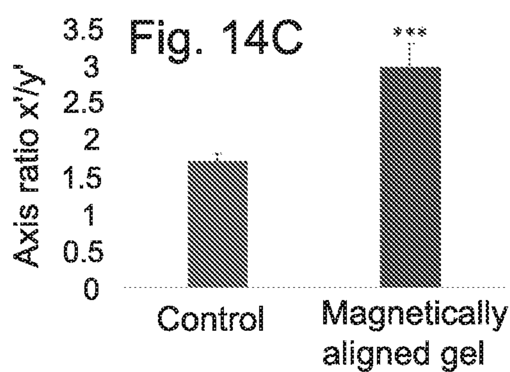

FIG. 14C. The elongation of neurons is measured by the aspect ratio between the long axis and the short axis of the cuboid for neurons in magnetically aligned gels and in control gels.

Figure 14D:
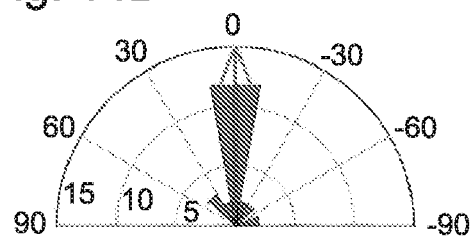

FIG. 14D. Histogram of deviation of orientation angle $\Delta\theta$ binned±15°. Deviation of orientation angle is defined as the difference between the cuboid representation angle and magnetic string orientation (depicted in grey arrow). Statistical analysis of the distribution of $\Delta\theta$ is not normal or uniform (one sample Kolmogorov-Smirnov Test). Scale bar 100 μm, ***$p<0.0005$.

FIG. 15A-15D. Neuronal growth in magnetically aligned gels

Figure 15A:
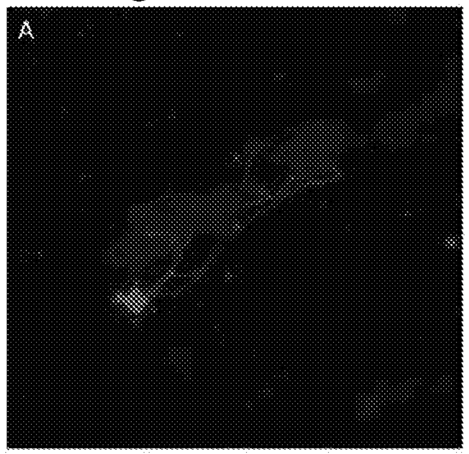
Figure 15B:
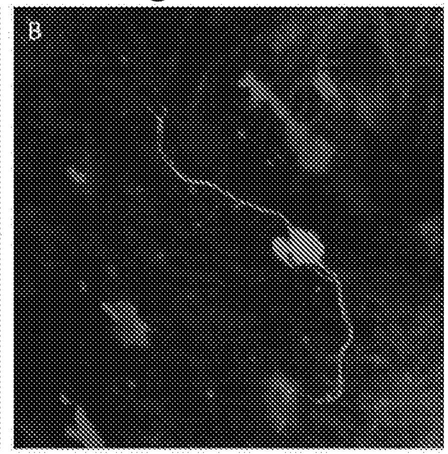

FIG. 15A-15B. show confocal z-stack of leech neurons grown in magnetically aligned gels.

Figure 15C:
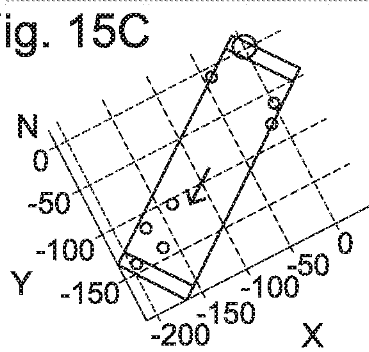
Figure 15D:
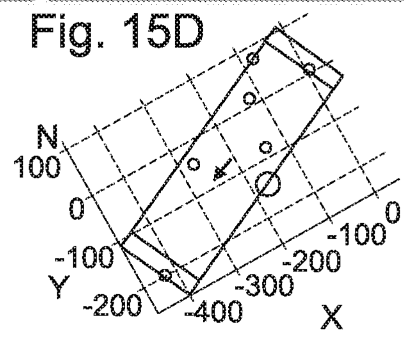

FIG. 15C-15D. show corresponding cuboid representation of the same cells. Grey arrow depicts calculated cuboid orientation and red arrow depicts magnetic string orientation. $\Delta\theta$ was calculated as the difference between the magnetic string orientation and the cuboid orientation.

FIG. 16A-16F. Neuronal growth in magnetically actuated gels of 3 mg/mL under different conditions FIG. 16A. Leech Neuron stack image grown in control gel, absent of MPs and magnetic field.

FIG. 16B. Confocal stack image of a Leech neuron combined with a phase image of the gel grown in 3 mg/mL embedded with 1 μm solidified under the influence of a magnetic field of 255 G.

FIG. 16C. CRM image of the same gel as in FIG. 16B showing no clear orientation.

FIG. 16D. Elongation of neurons in the magnetically actuated gels as compared to cells grown in gels without MNPs or magnetic field (control cells), cells grown in gels without MNPs and solidified under 255 G magnetic field (control 255 G), gels containing 100 nm MNPs and solidified under 620 G (Magnetic alignment MNPs 620 G), gels containing 1 μm MPs and solidified under 255 G (Magnetic Alignment 1 μm 255 G). Elongation of magnetically aligned gels is also shown for gels containing 100 nm MNPs and solidified under 255 G, as shown in FIG. 5 (Magnetic Alignment MNPs 255 G)

FIG. 16E. Histogram of deviation of orientation angle Δθ of neurons in gels containing MNPs (100 nm) solidified under 620 G show no significant alignment.

FIG. 16F. Histogram of deviation of orientation of neurons grown in gels containing 1 μm MPs solidified under 255 G. Total of 27.7% of neurons grow within ±30° (chi-square 0.333 df 2). Scale bar=100 μm, p<0.01. *p<0.005 compared to control cells.

FIG. 17A-17F. Neuron viability assay

FIG. 17A. 7 days after seeding viability of leech neurons in magnetically aligned gels was measured using a live/dead assay.

FIG. 17B. Electrophysiological activity of a single neuron after 6 days in a magnetically aligned gel.

FIG. 17C. Schematic representation of a neuron illustrating the measured morphometric parameters. Numbers indicate neurites, green arrow represents neurite length.

FIG. 17D. Average neurite length of neurons in magnetically aligned gels vs. control gels.

FIG. 17E. Average total branching length of neurons in treated vs. control gels.

FIG. 17F. Average neurite number of neurons in magnetically aligned gels vs. control gels. *p<0.05**p<0.01.

FIG. 18A-18D. PC12 alignment in magnetically aligned gels FIG. 18A. Confocal stack image of a PC12 cell grown for 7 days in magnetically aligned gel of 3 mg/mL collagen gel containing 100 nm MNPs solidified under the influence of a magnetic field of 255 G.

FIG. 18B. Confocal stack image of a PC12 cell grown in 1.4 mg/mL collagen gel containing 1 μm MPs solidified under a magnetic field of 255 G.

FIG. 18C. Histogram of deviation of orientation angle Δθ binned±30° of gels as in A (chi-square 9.739 df 2).

FIG. 18D. Histogram of deviation of orientation angle Δθ binned±30° of gels as in B (chi-square 8.313 df 2). scale bar=75 μm.

FIG. 19A-19D. NGF-Functionalized MNPs for directing neuronal differentiation FIG. 19A. NGF conjugation schematic to MNPs.

FIG. 19B. α-tubulin labeled PC12 cells grown in 3 mg/mL collagen gel control for 1 week, with consecutive NGF treatment (50 ng/mL every 2 days). In the presence of NGF PC12 cells sprout neuronal process in all directions.

FIG. 19C. α-tubulin labeled PC12 cells grown in magnetically aligned collagen gels containing NGF-MNPs for 1 week. Collagen fiber alignment is visualized via background CRM image. Neurite orientation is guided by fiber alignment and NGF-MNP strings.

FIG. 19D. Negative control of α-tubulin labeled PC12 cells grown in 3 mg/mL collagen gel containing fluidMag-PEG/Amine for 1 week, without NGF treatment. In the absence of NGF PC12 cells do not grow neuronal processes. Scale bar=100μ.

Figure 20B:
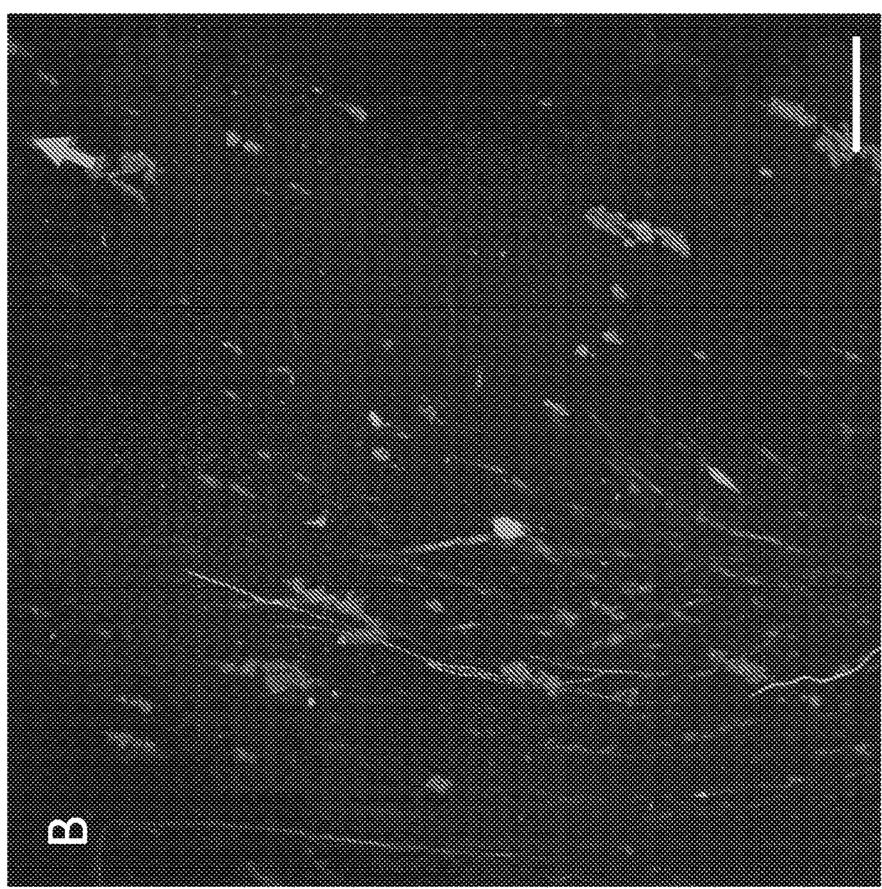
Figure 20A:
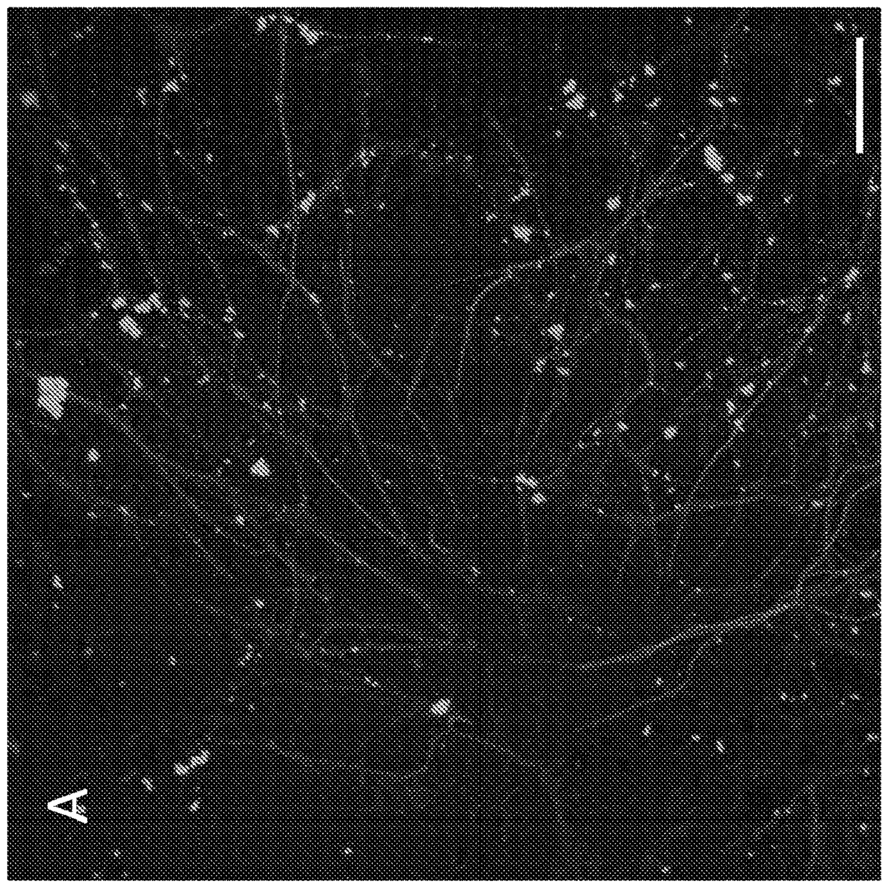

FIG. 20A-20B. Mouse DRG explant neurite outgrowth

FIG. 20A. Confocal z-stack image of neuronal outgrowth (neurofilament labeled) of mouse DRG grown within a control collagen gel for 1 week.

FIG. 20B. Confocal z-stack image of neuronal outgrowth (neurofilament labeled) of mouse DRG grown within magnetically aligned collagen gel.

Grey arrow indicates magnetic line direction. Scale bar=100 μm.

Figure 21A:
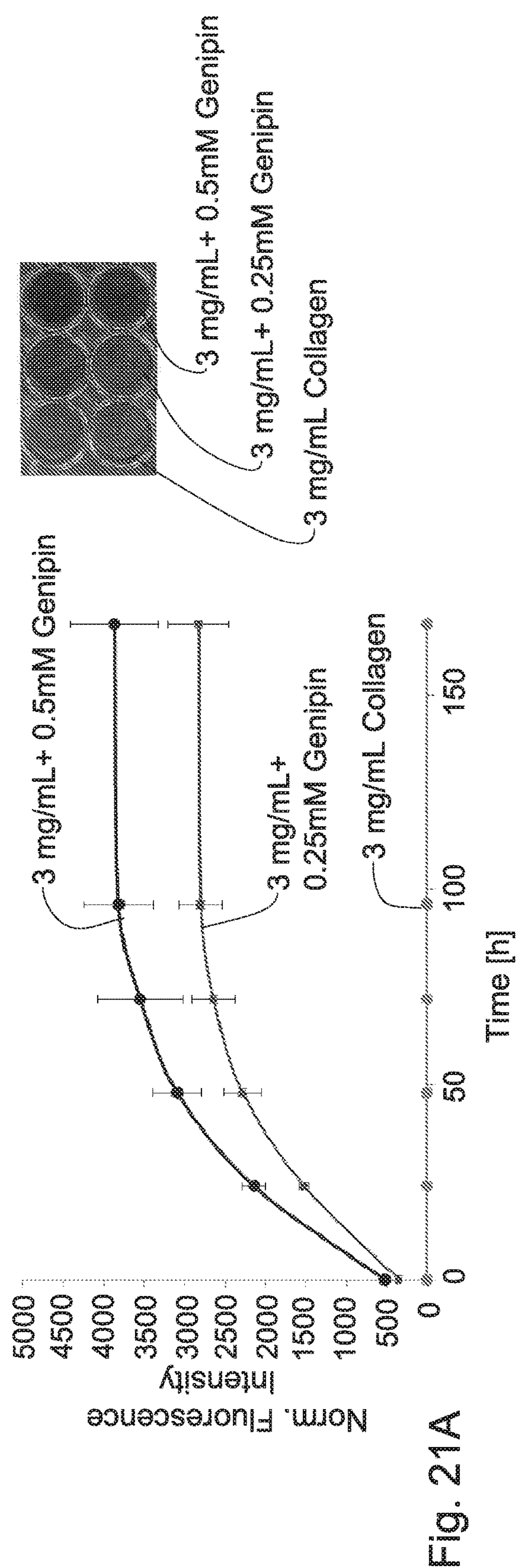
Figure 21B:
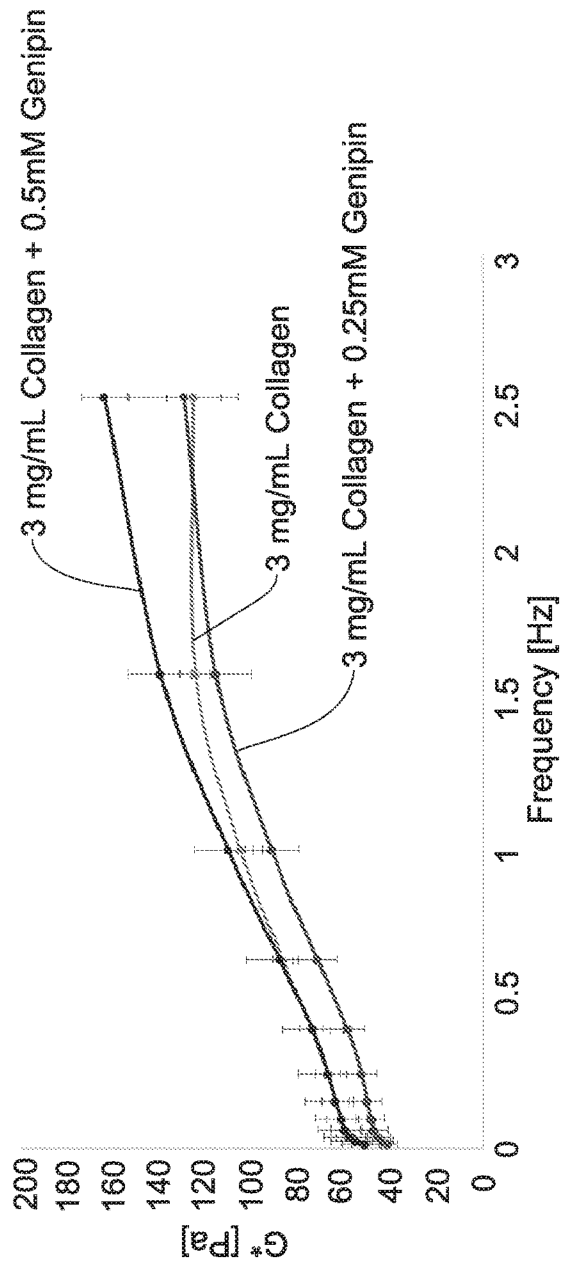

FIG. 21A-21B. The effect of genipin cross-linking on collagen gels

FIG. 21A. Fluorescence measurements (ex. 595 nm/em. 630 nm) of collagen gels (3 mg/mL) containing 0.25 or 0.5 mM genipin. Indent image of cross linked gels showing the effect of cross linking on absorbance. Left: control 3 mg/mL collagen gel, middle: 3 mg/mL collagen gel containing 0.25 mM genipin, right: 3 mg/mL collagen gel containing 0.25 mM genipin.

FIG. 21B. complex modulus of collagen gels (3 mg/mL) containing 0.25 or 0.5 mM genipin following 1 week post gelation.

FIG. 22A-22E. The Effect of Genipin cross-linking on gel matrix

Figure 22A:
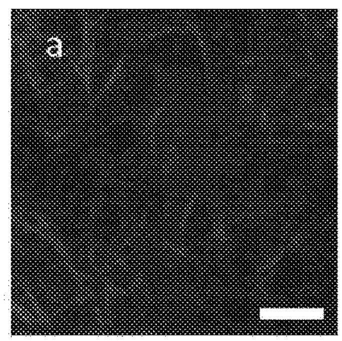

FIG. 22A. Sample CRM images of control gel 3 mg/mL gel

Figure 22B:
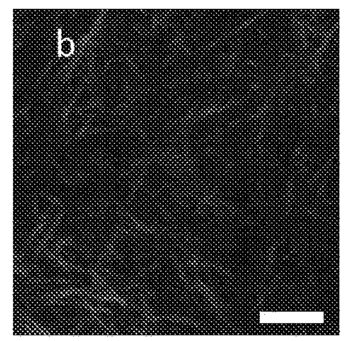

FIG. 22B. Sample CRM images of gel treated with 0.25 mM genipin

Figure 22C:
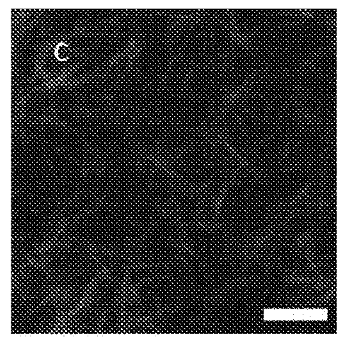

FIG. 22C. Sample CRM images of gel treated with 0.5 mM genipin.

Figure 22D:
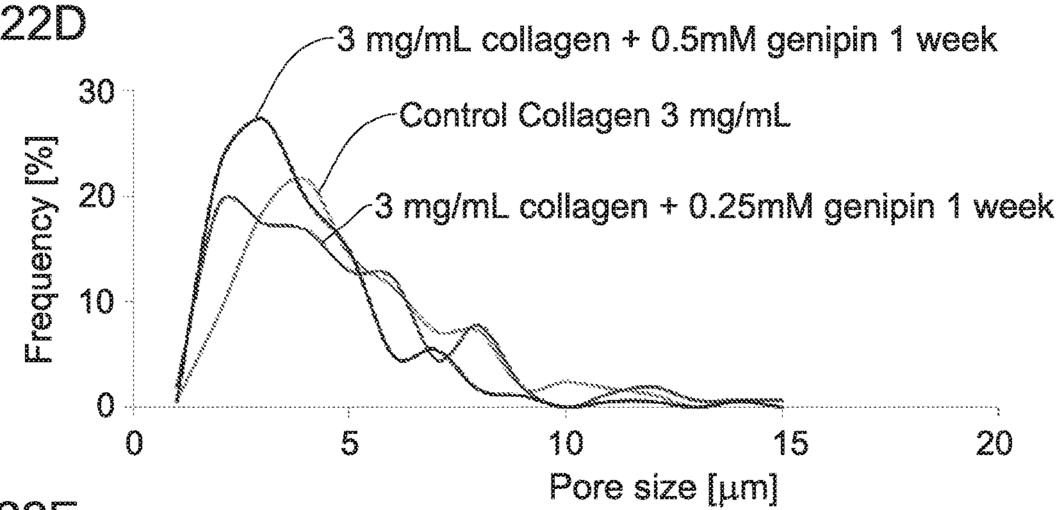

FIG. 22D. Analysis of pore size distribution driven from CRM images show a small decrease in pore size in cross-linked gels.

Figure 22E:
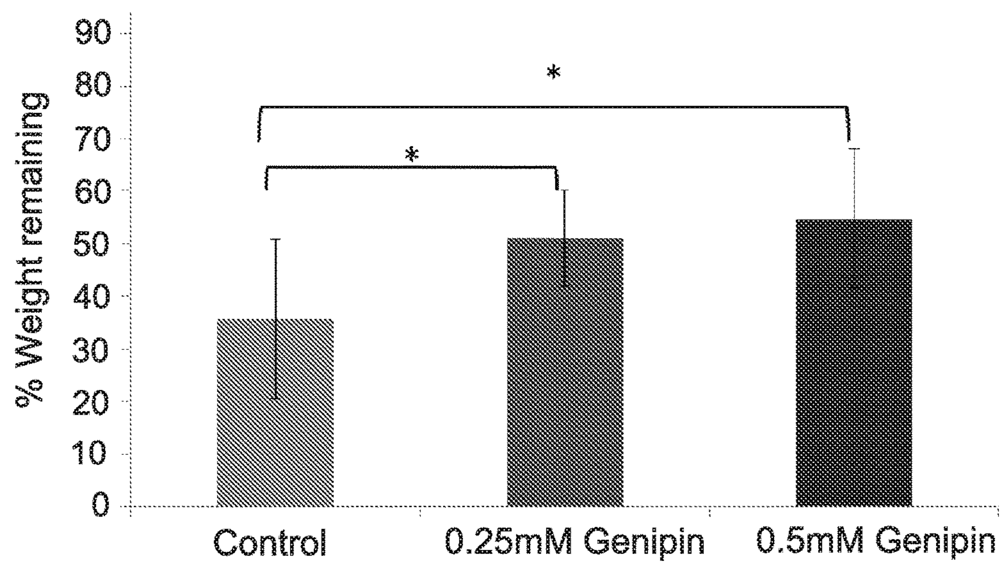

FIG. 22E. Degradation of cross-linked gels in collagenase (0.5 mg/mL in PBS, 17 h). scale bar=50 μm. *p<0.05.

FIG. 23A-23D. Fibroblasts in cross-linked and magnetically aligned collagen gels FIG. 23A. confocal z-stack tubulin labeled 3T3 cell grown for 1 week within magnetically aligned and cross linked gel (3 mg/mL gel with 0.25 mM genipin, fluidMag-OA 950 G).

Figure 23A:
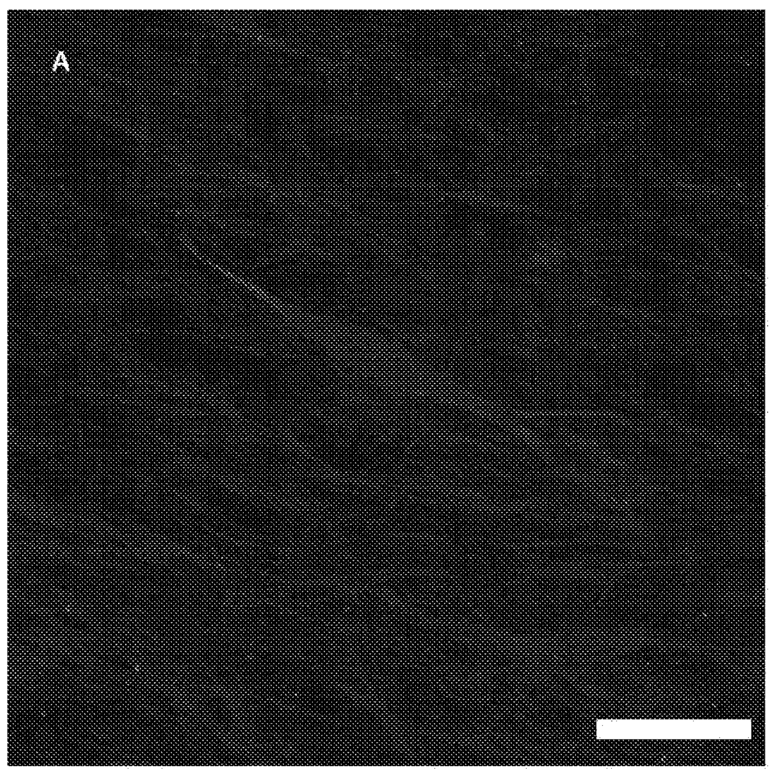
Figure 23B:
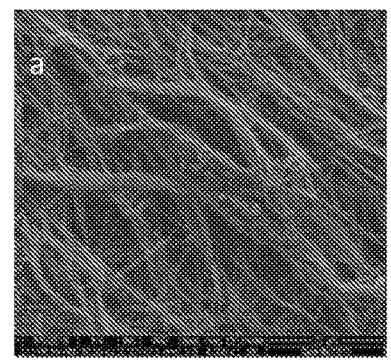

FIG. 23B. high resolution SEM image of a 3T3 cell grown on top of aligned and cross linked gel.

Figure 23C:
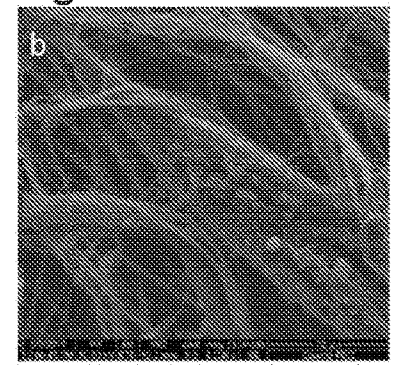

FIG. 23C. high resolution SEM image of a 3T3 cell grown on top of aligned and cross linked gel.

Figure 23D:
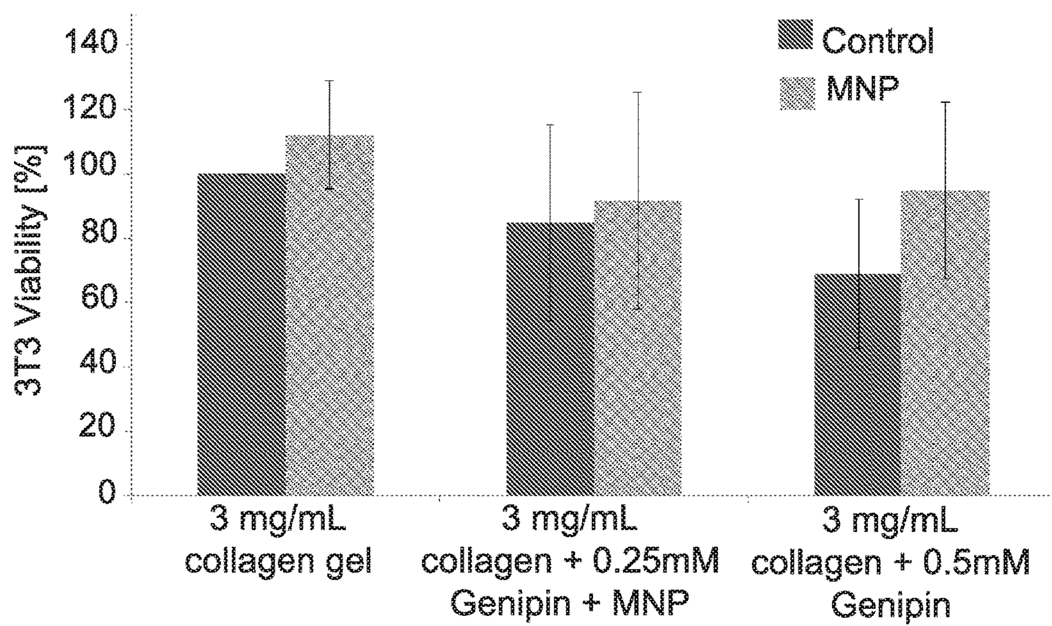

FIG. 23D. Viability assay of 3T3 cells within cross-linked gels, with fluidMag-OA and without. Results of 3 individual experiments. Scale bar=50 micron.

Figure 24A:
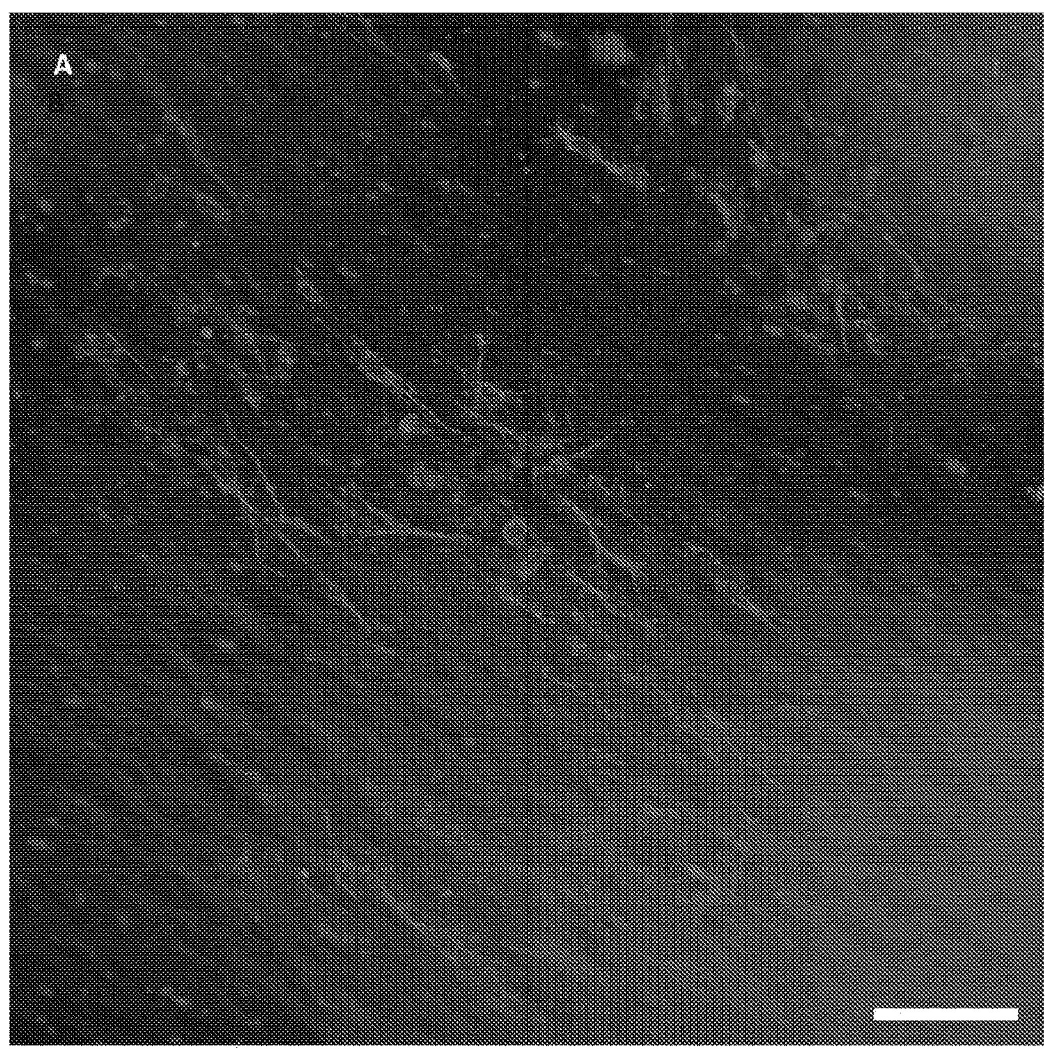
Figure 24B:
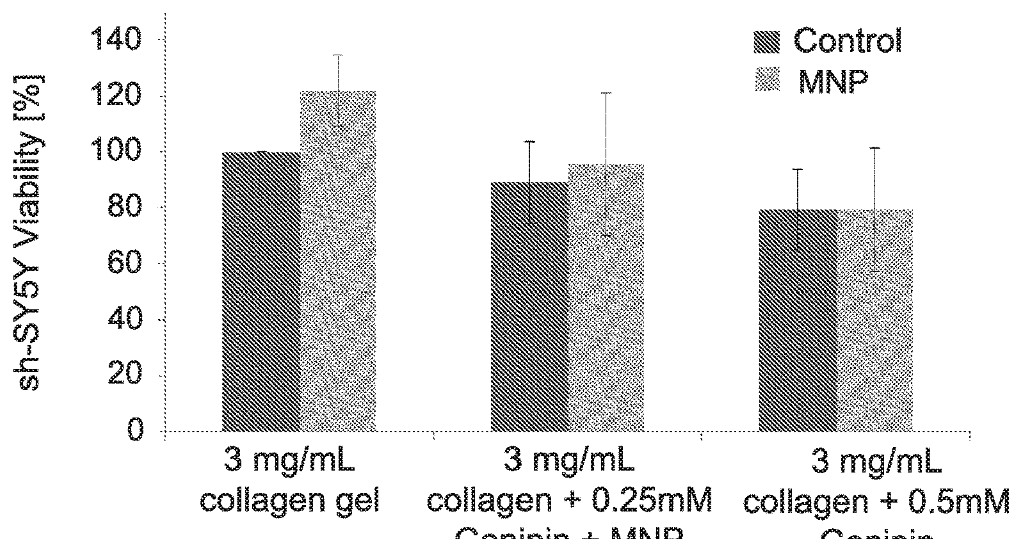

FIG. 24A-24B. SHSY-5Y cells in cross-linked and magnetically aligned collagen gels FIG. 24A. confocal z-stack tubulin labeled SH-SY5Y grown for 1 week within magnetically aligned and cross linked gel (3 mg/mL gel with 0.25 mM genipin, fluidMag-OA 950 G). Background CRM image shows fiber alignment FIG. 24B. Viability assay of SH-SY5Y cells within cross-linked gels, with fluidMag-OA and without. Results of 3 individual experiments. Scale bar=100 micron.

DETAILED DESCRIPTION OF THE INVENTION

The present invention now presents the development of a method to create 3D platforms based on collagen hydrogel combined with magnetic nano particles (MNPs), as scaffolds for functional neuronal regeneration. The method of the invention allows controlling the alignment of the magnetic gel-based scaffolds dynamically and remotely. By actuating a relatively low external magnetic field, the magnetic elements have aggregated into magnetic particle strings along the magnetic field lines within the gel. The present invention demonstrates that these strings have served as physical cues for neurons that developed in close proximity to the particles, leading to elongated and directed growth pattern. Interestingly, the movement and alignment of the magnetic particles during the gelation period (less than an hour) have led to the alignment of the collagen fibers as well. As gelation proceeds, following MNP stabilization, collagen fibers keep elongating, retaining the initial orientation in a template-like manner. This process was found to be sensitive to the formation and dynamics of the MNP strings within the collagen.

The invention shows that in gels that combined the alignment process of both particles and fibers, the neuronal branching tree was significantly co-oriented with the scaffold. Based on the neuronal response to the different examined gels, the inventors have concluded, that high concentration collagen gels mixed with nanometric magnetic particles (having a dry core diameter of about 10 nm) demonstrate optimal conditions for directing neuronal regeneration. Similar results were obtained also with fibroblasts, thereby establishing the feasibility of skin regeneration as well.

Moreover, the ability to implant a scaffold directly into the injured site, then manipulating its orientation according to the pathological need, is a therapeutic challenge successfully addressed by the present invention. This gel has been achieved by controlling gel orientation remotely post implantation during the gelation period. More specifically, the method of the invention involves provision of the MNP containing collagen (e.g., by injection) as a liquid directly into the injured site. Such approach holds the potential to fill complex defect shapes and to be aligned according to the pathology need. The ability to program the magnetic fields allows designing different microstructure orientations of the regenerative platform in the desired orientation. The present invention, together with recent advances involving magnetic nanoparticles and the penetrability of magnetic fields into human tissue, open future possibilities for remotely controlled scaffolds for tissue engineering applications.

Thus, in a first aspect, the invention provides a method for guiding growth of a cell, a mixture of cells, plurality of cells, or cell component/s. More specifically, the method of the invention may comprise the following steps:

In a first step (a), providing at least one liquid biomaterial or biomaterial solution, comprising the cell/s, plurality of cells, or mixture of cells and magnetic particles or any conjugate, mixture, embedment and encasement thereof or any composition or matrix comprising the same. In the next step (b), providing at least one or at least two magnetic sources that according to some embodiments, may be placed at a distance providing a magnetic field having a strength of between about 5 G to about 5000 G. The next step (c), involves solidifying the biomaterial while applying the magnetic field, thereby aligning along the magnetic field lines, at least one of the magnetic particles or aggregates thereof and components of the biomaterial. The method of the invention may comprise a further step of removing the magnetic sources once the biomaterial is solid. In the next step (d), allowing cell growth within the solidified biomaterial obtained in step (c), thereby guiding the growth of the cells or cell components in some embodiments, longitudinally oriented, along at least one of the aligned magnetic particles or aggregates thereof and the aligned components of the biomaterial. In some embodiments, the growth of the cells may be oriented along magnetic field lines.

It should be noted that in some embodiments, steps (a) to (d) of the method of the invention may be repeated several times, specifically, 1, 2, 3, 4, 5, 6, 7, 8, 9, 10 times or more, thereby creating different layers of solidified and aligned biomaterial comprising cell/s and magnetic particles. In yet some further embodiments, the layers may be either identical or different (e.g., having different composition of at least one of biomaterial, cells and beads).

It should be noted that in some embodiment, the method of the invention may be performed either in vivo, specifically in a living organism, more specifically, in situ, within the injured tissue. In yet some further embodiments, the method of the invention may be performed in vitro, out of the body or injured tissue, for example, in a device, cell culture or any external system.

The present invention thus provides a method for guiding and controlling cell growth that may in some embodiments be a cell growth in an implant and in further embodiments, in an implant in situ. The phrases "guiding growth" or "directing growth" as used interchangeably herein refer to causing an object (e.g., a cell or cell component) to grow or migrate in a particular direction.

More specifically, in a first step, the method of the invention provides a biomaterial solution. The term "liquid biomaterial" or "biomaterial solution" as used herein refers to a biocompatible material that is suitable for introduction into a living body, specifically provided as a solution, specifically, in an injectable form.

In some specific embodiments, the biomaterials useful in the present invention may be polymeric biomaterials. Polymerization of the polymeric biomaterials of the invention may lead to solidification thereof, and therefore, in some embodiments, the polymeric biomaterial used by the method of the invention may be provided in an un-polymerized state. Different chemical structures and functional groups in such polymers govern their morphology and properties, and allow precise control of the creation of desired molecular architectures for a wide range of applications in the biomedical field. Biomaterials derived from polymers generally fall into two categories: naturally occurring and human-made synthetic materials. Collagens, alginate and chitosan based materials are the best examples of biomaterials derived from natural resources. The polymers derived from synthetic origins may be divided into two classes: non-biodegradable and biodegradable synthetic polymers. As indicated above, the un-polymerized liquid biomaterial, or biomaterial solution of the invention is provided by the method of the invention with cells and magnetic particles.

In some specific embodiments, the invention provides the use of magnetic particles in the biopolymer solution of the invention. Magnetic particles are a class of particle that can be manipulated using magnetic fields. Such particles commonly consist of two components, a core made of magnetic material, often iron, nickel and cobalt, and a chemical component that has functionality. The term "magnetic beads" and "magnetic particles" are used herein interchangeably and refer to any particle dispersible or suspendable in solution, which may be attracted or guided by application of a magnetic field. Non-limiting examples of magnetic particles include microspheres, conjugates, micelles, colloids, liposomes, aggregates or complexes of a ferromagnetic, paramagnetic or superparamagnetic material.

It is within the spirit of this disclosure to use magnetic nanoparticles of any type of material. A person of ordinary skill in the art with the benefit of this disclosure will know which type of material is best for a particular situation. For example, magnetite may be a good choice because it has a large saturation magnetization, so relatively large forces can be generated with relatively fewer particles. Further specific magnetic particles relevant to the present invention will be discussed in more detail herein after.

The term "magnetic" refers to a material, which is paramagnetic, ferromagnetic, superparamagnetic and/or antiferromagnetic, examples of which include elemental iron, chromium manganese (e.g., chromium dioxide), cobalt, nickel, or a compound thereof. The iron compound may be an iron salt, which may be selected from the group, which includes magnetite ($Fe_3O_4$), maghemite ($Fe_2O_3$) and greigite ($Fe_3S_4$), or any combination thereof.

In some specific embodiments, either ferromagnetic or superparamagnetic particles may be used by the methods of the invention. The magnetic nanoparticles which are super-paramagnetic rather than ferromagnetic providing the important advantages of not attracting each other when not in the presence of an external magnetic field thereby avoiding the formation of clusters. Super-paramagnetic particles exhibit magnetic properties similar to paramagnetic particles. These particles but do not retain any significant magnetization in the absence of an external magnetic field (a field smaller or comparable to the earth's field) but have ferromagnetic characteristics such as susceptibilities of many thousands, when exposed to a magnetic field. Exposure to magnetic fields polarize the particles along the magnetic field lines and the particles will follow magnetic force lines in a non-uniform magnetic field.

It should be appreciated that in certain embodiments, the biomaterial provided by the methods of the invention may comprise magnetic particles of one type or more, specifically, 1, 2, 3, 4, 5, 6, 7, 8, 9, 10 or more. The magnetic particles used may vary in size, composition and coating.

In the next step (b), the method of the invention provides at least one magnetic source providing a magnetic field having a strength of between about 5 Gauss (G) to about 5000 G. The term "magnetic source" as used herein refers to a material or object that produces a magnetic field, e.g. a magnet. This magnetic field is responsible for the most notable property of a magnet: a force that pulls on other ferromagnetic materials, such as iron, and attracts or repels other magnets. In some embodiments, at least one magnetic source may be provided by the invention. In some further embodiments, at least two magnetic sources or more may be provide by the invention. In yet some further embodiments, plurality of magnetic sources, optionally arranged in an array, may be provided by the methods and kits of the invention. In some specific embodiments, two magnetic sources may be used by the method of the invention.

Magnets for use in the medical arts and in particular those suitable for aligning magnetic particles in the biomaterial of the invention, specifically those having the specified structural properties discussed herein before, are familiar to those of skill in the art. They include either a superconducting magnet or fixed/rare earth magnet with sufficient field density uniformity and magnetic field gradient to direct the magnetic particles and hold them in place. Specifics of magnetic field strength will vary by need, such that stronger fields/gradients will be used when the magnet is required to act at greater distances, and weaker fields/gradients may be used when the magnet can be localized closer to the magnetic particles in the biomaterial of the invention and/or the implant produced by the methods of the invention. The magnetic sources used by the method of the invention provide a magnetic field having a strength of between about 5 G to about 5000 G. It should be understood that such magnetic field is applied on the biomaterial of the invention.

The term "magnetic field" refers to a magnetic effect of electric currents and magnetic materials and is specified, at any given point, by both a direction and a magnitude (or strength); as such, it is a vector field.

According to some embodiments, magnetic fields, created either with permanent magnets or current-carrying wires, may apply forces to the magnetic particles. Such forces may move the magnetic particles, or hold them in the region of, maximum magnetic field amplitude.

The magnetic fields utilized in the systems and methods of the present disclosure may be provided by any suitable source. Such sources include, but are not limited to, magnetic fields generated by magnets, magnetic fields generated by the flow of electric current, or a combination thereof. In certain embodiments, suitable magnetic fields generated by the flow of electric current may be provided by the flow of electric current through one or more conductive wires.

Thus, in certain embodiments, the methods of the invention may use as a magnetic source permanent magnets or electromagnets.

A permanent magnet is an object made from a material that is magnetized and creates its own persistent magnetic field. Materials that can be magnetized, which are also the ones that are strongly attracted to a magnet, are called ferromagnetic (or ferrimagnetic). These include iron, nickel, cobalt, some alloys of rare earth metals, and some naturally occurring minerals such as lodestone.

Some specific properties used to compare permanent magnets include Remanence (Br) which measures the strength of the magnetic field, Coercivity (Hci) which corresponds to the material's resistance to becoming demagnetized, Energy product (BHmax) i.e. the density of magnetic energy, Curie temperature (TC) which is the temperature at which the material loses its magnetism.

An electromagnet is made from a coil of wire that acts as a magnet when an electric current passes through it but stops being a magnet when the current stops. Often, the coil is wrapped around a core of "soft" ferromagnetic material such as steel, which greatly enhances the magnetic field produced by the coil.

In yet some specific embodiments, the methods of the invention may use as a magnetic source permanent magnet/s.

It should be noted that the magnetic sources and the magnetic field provided thereby must be flexible and adapted to the specific therapeutic need. Thus, a person of ordinary skill in the art with the benefit of this disclosure will know whether it is more advantageous to use permanent magnets, current carrying magnets, or some combination thereof. For example, permanent magnets may produce larger fields and forces. Wires may be more easily patterned to form magnetic field patterns, may make smaller structures, and may be more flexible for manipulation.

Magnetic fields of some embodiments of the present inventions, produce force fields to attract and align the magnetic particles comprised within the biomaterial of the invention along the magnetic field lines. In yet some further embodiments, the magnetic field provided by the permanent magnets used by the methods and kits of the invention, produces force field sufficient to align different components of the biomaterial used by the invention.

In some embodiments, the magnetic field useful in the method of the invention may be a static magnetic field (also referred to as electrostatic field) i.e. the field does not vary with time. A static magnetic field is created by a magnet or charges that move as a steady flow (as in appliances using direct current). In contrast, time-varying electromagnetic fields, which reverse their direction at a regular frequency, are produced by appliances using alternating current (AC). In this case, the magnetic fields is associated with a specific frequency. It should be noted that in most cases a static magnetic field may be applicable in the method of the invention, however, in some embodiments where appropriate also a time-varying electromagnetic field may be applied. In several embodiments, the magnetic field may be applied for a time period ranging from about 1 minute up to about 5 hours.

In some specific embodiments, the methods of the invention may provide as a magnetic source neodymium magnet/s. Neodymium magnet (also known as NdFeB, NIB or Neo magnet), the most widely used type of rare-earth magnet, is a permanent magnet made from an alloy of neodymium, iron and boron to form the Nd2Fe14B tetragonal crystalline structure. Neodymium magnets are graded according to their maximum energy product, which relates to the magnetic flux output per unit volume. Higher values indicate stronger magnets and range from N35 up to N52. Letters following the grade indicate maximum operating temperatures (often the Curie temperature), which range from M (up to 100° C.) to EH (200° C.). In some specific embodiments, neodymium magnet with the following grades may be used in the methods and kits of the invention, specifically, N50, N35-N52, N33M-N48M, N30H-N45H, N30SH-N42SH, N30UH-N35UH, N28EH-N35EH.

Neodymium magnets have higher remanence, much higher coercivity and energy product, but often lower Curie temperature than other types. Special neodymium magnet alloys that include terbium and dysprosium have been developed that have higher Curie temperature, allowing them to tolerate higher temperatures. It should be noted that any neodymium magnet specified above may be used by the method of the invention, as well as the kits described herein after. In some embodiments, NdFeB Grad N50 may be used by the methods of the invention.

It should be appreciated that for providing a magnetic field having a strength of between about 5 G to 500 G, the number of magnetic sources, specifically, magnets, the size thereof, configuration and orientation, as well as their related distance, may be manipulated. For example, in some embodiments, at least one magnetic source may be provided by the invention. In some further embodiments, at least two magnetic sources may be provide by the invention. In more specific embodiments, 1, 2, 3, 4, 5, 6, 7, 8 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more magnetic sources, or an array of plurality of magnetic sources, may be used by the method of the invention. Still further, the magnetic sources, specifically magnets, may be arranged in any configuration to direct magnetic field lines at the desired configuration. In yet some further embodiments, any shape of magnets may be used, specifically, bar, rods, horseshoe, disc, sphere, cylinders, cubes, plates, rings and the like. In some specific embodiments, different combinations of magnets may be used. In some embodiments, for specific design of magnetic line shape and flux, simulations may be used to prepare the shape of magnets and combination.

In some specific embodiments, at least two magnetic sources, specifically magnets, may be placed each on each side of the biomaterial solution of the invention, to create magnetic field lines that are parallel to the surface of the biomaterial. In some further specific embodiments an array of magnets may be placed to augment the magnetic field lines, such as Halbach Arrays to give a static field of various shapes. This includes spheres, S-shapes, cylinder, hexagon. Changing magnet sizes can affect magnetic line arrangement leading to highly controlled line structures, even complex.

In some specific embodiments, different alignment structures may be fabricated and arranged on top, or within, of consisting gel aligned structures to achieve complex architectures.

In yet some further embodiments, it should be noted that arranging the poles of each magnet with respect to the other magnets may also affect the direction of the field lines. For example, arranging the direction of north pole and the south pole of each of the magnets used with respect to the other magnet/s may be also used as a tool for creating magnetic field lines having a desired non-regular structure.

It must be understood that the size of the magnets or magnetic source/s may also vary. In some embodiments, magnets useful in the method of the invention may have a size ranging between about 0.1 to 5000 mm, specifically, about 1 mm to 500 mm or more, by 1 mm to 500 mm More specifically, about 1, 2, 3, 4, 5, 6, 7, 8 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, 500 mm or more, by about 1, 2, 3, 4, 5, 6, 7, 8 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, 500 mm or more. In some particular and non-limiting embodiments, two magnets of about 18 mm by 18 mm, may be used.

Still further, it should be also understood that the distance between the magnetic sources, as well as the distance between each of the magnetic sources and the biomaterial solution of the invention, may also vary to provide the desired magnetic field strength. As demonstrated by FIG. 1B, the distance between the two magnetic sources may range between about 0.1 cm to 100 cm, specifically, about 0.1, 0.2, 0.3, 0.4, 0.5, 0.6, 0.7, 0.8, 0.9, 1, 2, 3, 4, 5, 6, 7, 8 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 cm or more. In some specific embodiments, the distance between the two magnetic sources may range between about 1 cm to 15 cm.

In yet another embodiments, the distance between the magnets and the site of injury and/or the biomaterial of the invention may range from about 0.1 cm to about 50 cm specifically, about 1, 2, 3, 4, 5, 6, 7, 8 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 cm and more specifically, about 1 to 15 cm.

In yet some further embodiments, the magnetic field strength provided by the method of the invention may range between about 5 G to about 5000 G. More specifically, in some embodiments, the magnetic field provided by the method of the invention may be at a strength of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1000, 1050, 1100, 1200, 1250, 1300, 1350, 1400, 1450, 1500, 1550, 1600, 1650, 1700, 1750, 1800, 1850, 1900, 1950, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000 G or more.

In some particular and non-limiting embodiments, the method of the invention may use magnetic sources providing a magnetic field having a strength of 225 G. In some specific embodiments, said magnetic field strength may be used for biomaterial solution comprising uncoated magnetic beads having a size of between 10 nm to 100 nm. In yet some further specific and non-limiting embodiments, the methods of the invention may use magnetic sources providing a magnetic field having a strength of 950 G. In some specific embodiments, said magnetic strength may be applied on biomaterial solution comprising magnetic beads coated with oleic acid having a size of between about 10 nm to 100 nm. In yet some further specific and non-limiting embodiments, the methods of the invention may use magnetic sources providing a magnetic field having a strength of 570 G.

In some embodiments, one or more magnetic fields or magnetic field gradients may be employed in the methods of the invention (e.g., an external source of magnetic fields or magnetic field gradients). Such fields or gradients can be generated by, for example, one or more magnets and associated medical devices placed within or adjacent to a target tissue.

In the next step (c) of the methods of the invention, the biomaterial provided in step (a) is allowed to solidified or polymerized, while the magnetic field in the indicated strength, is applied.

The term "solidifying" refers to a transition state or a process wherein a liquid material become solid or hard, specifically with respect to its previous state. It should be noted that solidification may be also a gelation of the biomaterial used by the invention. In yet some further embodiments, solidification may involve polymerization of the gel. Solidification of a material may be induced by change in temperature (either cooling or heating), addition of cross-linking agent or exposure to light, specifically, ultraviolet (UV) irradiation. In some embodiments, a biomaterial of the invention may be considered as solidified if it is at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or about 100% more solid than its previous liquid state.

As noted above, "to solidify" the biomaterial solution of the invention may also involve changing the temperature of the biomaterial. In some specific embodiments, the biomaterial solution of the invention is kept liquid in a temperature of about 4° C. to about 15° C. In yet some further embodiments, the biomaterial solution of the invention is allowed to solidify at a temperature of between about 20° C. to 40° C., specifically, about 20, 21, 22, 23, 24, 25, 26, 27, 28, 29, 30, 31, 32, 33, 34, 35, 36, 37, 38, 39, 40° C. In some particular embodiments, the biomaterial solution of the invention may be solidified at a temperature of 25° C. In yet some further embodiments, the biomaterial solution of the invention may be solidified at a temperature of 37° C. It should be understood that the temperature used for solidification also affects the time required to solidify the biomaterial solution. For example, the time required for solidification may range between about 1 minutes or less to about 1 hour or more, specifically, 1, 2, 3, 4, 5, 10, 20, 25, 30, 35, 40, 45, 50, 55, 60 minutes or more. In some specific embodiments, the biomaterial solution of the invention may be solidified at a temperature of 25° C. for about 40 minutes. In yet some further specific embodiments, the biomaterial solution of the invention may be solidified at a temperature of 37° C. for about 30 minutes. It must be understood that the solidification time and conditions may be also manipulated by the skilled artisan, as a function of the thickness of the biomaterial layers applied and the concentration of the biomaterial polymer in the solution. It should be noted that temperature can be controlled by setting external temperature to the potential container, for example, syringe that hold the biomaterial. Still further, as mentioned above, the solidification step may involve exposure of the biomaterial solution of the invention to photo-polymerization (exposure to specific light wave-length, for example, UV) or chemical-polymerization, by changing the pH, or adding a cross-linker. In some particular embodiments, a cross linker such as genipin, or carbodiamide cross-linking may be used. Thus, in some embodiments, step (c) of the method of the invention may further comprise the addition of a cross-linking agent to the biomaterial solution of the invention in an amount sufficient that the gel will solidify under the indicated magnetic field.

This, in yet some further embodiments, step (c) of the method of the invention may further comprise an additional stage of providing suitable conditions for solidifying the biomaterial. Such conditions may include, temperature, time, pH, exposure to light of particular wave length, addition of cross linkers and the like, as discussed above.

The next step (d) involves allowing cell growth within the solidified biomaterial. It should be noted that in certain embodiments, cell growth as used herein encompasses cell division and proliferation, but may also relate to elongation, thickening, branching out, splitting, multiplication, maturation and development of cell, cell components, organelles or any projections thereof. It must be understood that to allow the growth or at least a partial growth of the cells or cell components in step (d) of the methods of the invention, further agents, compounds or reagents required for cell growth, may be added to the biomaterial solution. Such reagents may include specific growth medium, serum, antibiotics, growth factors and the like. Thus, in certain embodiments, the at least one biomaterial solution/s provided by the methods of the invention may further comprise growth factors including but not limited to at least one of epidermal growth factor (EGF), transforming growth factor P (TGFB- 1, TGFss-2), platelet derived growth factor (PDGF-AA, PDGF-AB, PDGF-BB), fibroblast growth factor (FGF), insulin-like growth factors (IGF), tumor necrosis factors (TNF), colony stimulating factors (CSFs), nerve growth factors (NGF), ciliary neurotrophic factor (CNTF), glial derived neurotrophic factor (GDNF) and the like, and/or therapeutic agents including but not limited to at least one of cytokines, interleukins or other co-factors such as heparin or calmodulin, antibiotics, antineoplastic and antibacterials, to further stimulate or control the growth of cells or any component/s thereof.

According to some embodiments, the liquid biomaterial used by the method of the invention may be liquid hydrogel.

The term “gel” as used herein refers to a polymer network or semisolid colloidal suspension of a solid in a liquid. “Hydrogel” in certain embodiments, refers to a crosslinked form of soft polymers that has the ability to form scaffolds for a variety of uses, such as tissue engineering, delivery of active molecules, and biosensors and actuators. Hydrogels can be synthesized both from natural and synthetic polymers. The examples of hydrogels from natural polymers may include but are not limited to collagen, gelatin, hyaluronic acid, chondroitin sulfate, chitin and chitosan, fibrin, fibrinogen, Hyaluronan, laminin, alginate, starch, cellulose, and their derivatives. Hydrogels from natural polymers have many advantages over the synthetically derived ones such as low toxicity and good biocompatibility because of their chemical structures and are very akin to the structure of glycosaminoglycan (GAG) molecules present in the native extracellular matrix (ECM). Hydrogels from synthetic polymers are prepared by chemical polymerization methods. Various types of monomers, for examples, acrylates, methacrylates, acrylamides, esters, carboxylic acid and polyfunctional monomers, can be utilized for the preparation of synthetic hydrogels. It should be noted that in certain embodiments, any of the hydrogels disclosed herein is applicable in the methods and kits or systems of the invention, as well as the implants prepared thereby, that are also encompassed by the invention.

In some specific embodiments, the hydrogel used by the methods of the invention (as well as by the kits of the invention described herein after), may be a natural polymer. In yet some further specific embodiments, a suitable polymer can be any biocompatible, non-immunogenic and, optionally, bio-erodible polymer which can form a hydrogel matrix or scaffold. In yet some further embodiments, such matrix or scaffold may be suitable for therapeutic applications as an implant, specifically for tissue repair and tissue engineering purpose, as will be elaborated herein after.

In some embodiments, the hydrogels used by the invention may be biocompatible, specifically, not causing or enhancing a biological reaction when implanted or otherwise administered within a mammal. The hydrogels, and any breakdown products of the hydrogels or polymers, preferably are not significantly toxic to living cells, or to organisms. The hydrogels also may have liquid crystalline properties for example at high concentration, which are useful in controlling the rate of delivery.

Ionic properties can be provided in the backbone of the polymers making up the hydrogels, conferring the further property of control of delivery and/or physical state by control of the ionic environment, including pH, of the polymer or hydrogel.

When the hydrogel is desired to be a temporary matrix for replacement by natural tissue, the material can be designed for biodegradability and system release, for example, by providing hydrolyzable linkages, using relatively low molecular weight chains, biodegradable crosslinking agents, biodegradable polymer backbones and/or low molecular weight polymer backbone sections. Alternatively, when less degradable hydrogels are desired, non-hydrolyzable linkages, chains of higher molecular weight, non-degradable crosslinking agents and/or higher molecular weight polymer backbone sections can be used.

It should be noted that polysaccharides that may be useful in the methods and kits of the present invention may include agarose and microbial polysaccharides such as Pullulan (1,4-;1,6-D-Glucan), Scleroglucan (1,3; 1,6-a-D-Glucan), Chitin (1,4-beta-D-Acetyl Glucosamine), Chitosan (1,4-beta-D-N-Glucosamine), Elsinan (1,4-;1,3-a-D-Glucan), Xanthan gum (1,4-beta-D-Glucan with D-mannose; D-glucuronic acid as side groups), Curdlan (1,3-beta-D-Glucan (with branching)), Dextran (1,6-a-D-Glucan with some 1,2; 1,3-;1,4-a-linkages), Gellan (1,4-beta-D-Glucan with rhamose, D-glucuronic acid), Levan (2,6-beta-D-Fructan with some beta-2,1-branching), Emulsan (Lipoheteropolysaccharide), and Cellulose (1,4-beta-D-Glucan). methyl cellulose, Hyaluronic acid, Chondroitin sulfate and Heparin, Still further, in some specific embodiments, examples of biopolymers which can be used in the present invention include collagen, alginic acid, polyvinyl alcohol, proteins, such as chondroitin sulfate, elastin, laminin, heparan sulfate, fibronectin and fibrinogen, Poly-(L-ornithine), Poly L-(lactic acid), poly(lactic-co-glycolic acid). In some embodiment, a combination or mixture of one or more biopolymers can be used to form the biopolymer forms, or layers of the invention.

In yet some further embodiments, the biomaterial of the invention may comprise a combination of two or more biopolymers. In some embodiments, the biomaterial solution provided by the invention may comprise 1, 2, 3, 4, 5, 6, 7, 8, 9, 10 or more biopolymers. In yet some specific embodiments, the biomaterial of the invention may comprise collagen and fibrin. In some alternative embodiments the biomaterial of the invention may comprise a combination of collagen and Hyaluronan.

In yet some specific embodiments, the hydrogel used by the methods of the invention may be collagen, specifically a collagen solution.

The term “collagen” as used herein refers to the main structural protein in the extracellular space in the various connective tissues in animal bodies. Depending upon the degree of mineralization, collagen tissues may be rigid (bone), compliant (tendon), or have a gradient from rigid to compliant (cartilage). Collagen, in the form of elongated fibrils, is mostly found in fibrous tissues such as tendons, ligaments and skin. It is also abundant in corneas, cartilage, bones, blood vessels, the gut, intervertebral discs and the dentin in teeth. In muscle tissue, it serves as a major component of the endomysium.

The collagen can be of the soluble or the insoluble type. In certain embodiments, collagen useful in the present invention may be soluble collagen.

So far, 28 types of collagen have been identified and described. They can be divided into several groups according to the structure they form: Fibrillar collagen (Type I, II, III, V, XI) and Non-fibrillar collagen as FACIT (Fibril Associated Collagens with Interrupted Triple Helices; Type IX, XII, XIV, XVI, XIX), Short chain (Type VIII, X), Basement membrane (Type IV), Multiplexin (Multiple Triple Helix domains with Interruptions; Type XV, XVIII), MACIT (Membrane Associated Collagens with Interrupted Triple Helices; Type XIII, XVII) and others (Type VI, VII).

The five most common types include, Type I found in skin, tendon, vascular ligature, organs, bone (main component of the organic part of bone, over 90% of the collagen in the human body), Type II found in cartilage (main collagenous component of cartilage), Type III found in reticulate (main component of reticular fibers), commonly alongside type I, Type IV that forms the basal lamina, the epithelium-secreted layer of the basement membrane and Type V found on the cell surfaces, hair and placenta.

It must be understood that according to certain embodiments, fibrillar collagen may be used as a biomaterial by the methods and kits of the invention.

It should be appreciated that the invention encompass the use of either a purified or recombinant collagen. In yet some further embodiments, specifically for therapeutic applications in the human body, collagen of a human source may be used in the methods and kits of the invention. Specifically, at least one of Collagen type I, alpha 1, as denoted by Accession number AAH36531, Collagen type I, alpha 2, as denoted by Accession number AAH54498, Collagen type II, alpha 1, as denoted by Accession number AAI16450, Collagen type III alpha 1 as denoted by Accession number AGL34959, Collagen, type IV, alpha 4 as denoted by Accession number EAW70845, Collagen, type IV, alpha 2, as denoted by Accession number EAX09112, Collagen, type IV, alpha 1, as denoted by Accession number EAX09109, Collagen, type IV, alpha 6, as denoted by Accession number EAX02687, Collagen, type IV, alpha 3, as denoted by Accession number EAW70855, Collagen, type IV, alpha 5, as denoted by Accession number AAI51847, Collagen, type V, alpha 2, as denoted by Accession number EAX10906, Collagen, type V, alpha 1 as denoted by Accession number EAW88131 and Collagen, type V, alpha 3, as denoted by Accession number EAW84061.

In some specific embodiments, the collagen used by the method of the invention may be collagen type I.

As used herein the term, "Type I collagen" is characterized by two alpha1 (I) chains, and one alpha2 (I) chains (heterotrimeric collagen). The alpha1 (I) chains are approximately 300 nm long. Type I collagen is predominantly found in bone, skin (in sheet-like structures), and tendon (in rope-like structures). Type I collagen is further typified by its reaction with the protein core of another connective tissue component known as a proteoglycan. It should be noted that in certain embodiments, the methods and kits of the invention may use as a biomaterial at least one of the human Collagen type I, alpha 1, that comprises the amino acid sequence as denoted by SEQ ID NO. 1, and encoded by the nucleic acid sequence as denoted by SEQ ID NO. 2, and the human Collagen type I, alpha 2, that comprises the amino acid sequence as denoted by SEQ ID NO. 3, and encoded by the nucleic acid sequence as denoted by SEQ ID NO. 4.

It should be appreciated that in some further embodiments, any commercially available collagen, specifically collagen type I, may be used for the methods and kits of the invention. More specifically, a large variety of collagen derived products are available. For example, Type I collagen can be bought as pepsin-solubilized dermal type I collagen (Vitrogen 100, FXP-019) and Type II collagen from chicken sternal cartilage can be bought as powder (Sigma Aldrich, CAS Number 9007-34-5). Suitable types of injectable collagen materials comprise recombinant human collagen type I, recombinant human collagen type III, tissue engineered human-based collagen type I, porcine collagen type I, porcine collagen type III, human type IV placental collagen, for example, at a 2% concentration at neutral pH in phosphate buffered saline ("PBS"), solubilized elastin peptides with bovine collagen, and bovine collagen including ZYDERM® I, ZYDERM® II, and ZYPLAST® collagen implants.

Still further, in some embodiments, the biomaterial used by the methods and kits of the invention may comprise any type of collagen, specifically, those disclosed herein, or any combinations thereof or any combination of collagen with any suitable bio polymer/s.

In some embodiments, the concentration of the collagen solution may range between about 0.1 to about 10 mg/ml. Specifically, in some embodiments, a collagen solution having a concentration of 0.1, 0.2, 0.3, 0.4, 0.5, 0.6, 0.7, 0.8, 0.9, 1.1, 1.2, 1.3, 1.4, 1.5, 1.6, 1.7, 1.8, 1.9, 2, 2.5, 3, 3.5, 4, 4.5, 5, 5.5, 6, 6.5, 7, 7.5, 8, 8.5, 9, 9.5, 10 mg/ml or more, may be used. In more specific embodiments, a collagen solution of 1.4 mg/ml is used in the methods and kits of the invention. In yet some more specific embodiments, a collagen solution of 3 mg/ml is used in the methods and kits of the invention.

As also mentioned herein before, in some embodiments, the collagen gel may be cross-linked by addition of a cross liking agent. In some particular embodiments, the collagen type I biomaterial solution of the invention may be cross-linked using genipin. Genipin is a chemical compound found in *Gardenia* fruit extract. It is an aglycone derived from an iridoid glycoside called geniposide present in fruit of *Gardenia jasminoides*. Genipin is an excellent natural cross-linker for proteins, collagen, gelatin, and chitosan cross-linking Thus, in some embodiments, for a mixture of two or more polymeric biomaterials, genipin may be used as an appropriate cross-linker. It has a low acute toxicity in mice, therefore, much less toxic than glutaraldehyde and many other commonly used synthetic cross-linking reagents.

In some further embodiments, magnetic particles suitable for the method of the invention, may be particles composed of any one of a magnetite core, a maghemite core, Ferrite core or iron oxide core.

Ferrite nanoparticles or iron oxide nanoparticles (iron oxides in crystal structure of maghemite or magnetite) are the most explored magnetic nanoparticles up to date.

Magnetite is a mineral and one of the main iron ores. With the chemical formula $Fe_3O_4$, it is one of the oxides of iron. Magnetite is ferrimagnetic; it is attracted to a magnet and can be magnetized to become a permanent magnet itself. Maghemite (Fe2O3, γ-Fe2O3) is a member of the family of iron oxides. It has the same spinel ferrite structure as magnetite and is also ferrimagnetic.

In certain embodiments, magnetic particles suitable for the method of the invention, may be uncoated or coated magnetic particles.

It should be noted that uncoated magnetic particles were demonstrated by the invention as particularly useful in a magnetic field having a strength of 225 G and collagen gels of 1.4 mg/ml and 3% mg/ml. Thus, in yet some other embodiments, magnetic particles suitable for the method of the invention may be uncoated magnetic particles.

The term "uncoated magnetic particles" as used herein refers to magnetic particles wherein the surface of the particles was not covered partially or completely by any additional substance.

In yet some alternative embodiments, biocompatible magnetic nanoparticles, primarily composed of a magnetite (Fe3O4) and/or maghemite (Fe2O3) core with either a silica, dextran, or PYA coating may be utilized in the present invention. Such particles may be synthesized following methods known in the art. However, it will be understood that other magnetic nanoparticles may be utilized. Particle sizes can range from 0.1 nm up to a few microns e.g. 1 to 10 μm. Commercially available magnetic nanoparticles with varying surface chemistry may also be used.

Thus, in yet another embodiment, magnetic particles suitable for the method of the invention may be coated magnetic particles.

The term "coated" refers herein to functional coating i.e. covering that is applied to the surface of an object, usually referred to as the substrate. The coating itself may be an all-over coating, completely covering the substrate, or it may only cover parts of the substrate. Functional coatings may be applied to change the surface properties of the substrate, such as adhesion, wettability, corrosion resistance, or wear resistance. In some cases, the coating adds a completely new property such as a magnetic response or electrical conductivity. Relevant coating of the magnetic particles may enable adhesion/conjugation of biological factors of interest, as for example NGF, described in more details herein after, to create functionalized magnetic particles.

The surface of a maghemite or magnetite magnetic nanoparticle is relatively inert and does not usually allow strong covalent bonds with functionalization molecules. However, the reactivity of the magnetic nanoparticles can be improved by coating, for example with a layer of silica onto their surface. The silica shell can be easily modified with various surface functional groups via covalent bonds between organo-silane molecules and silica shell.

Therefore, magnetic particles or nanoparticles, may comprise a magnetic core with a biocompatible coating. The biocompatible coating may comprise a polymer, e.g., dextran, polyvinyl alcohol (PVA), polyethylenimine (PEI), silica, dextransulfate, starch, citric acid salt, PEG/Amine, Chitosan, Streptavidin, or Oleic acid sodium salt.

In yet some specific embodiments, any magnetic particles of any size used by the methods and kits of the invention, specifically, in case of micro-particles, may be coated particles, provided that said coating is not a Streptavidin coating.

In more specific embodiments, the magnetic particles suitable for the method of the invention may be magnetic particles coated with oleic acid-sodium salt.

In yet some further particular and non-limiting embodiments, such magnetic particles coated with oleic acid-sodium salt may be suitable for use in 3 mg/ml or 1.5 mg/ml collagen gel, where a magnetic field having a strength of about 950 G is applied.

In other embodiments, the magnetic beads suitable for the methods of the invention may be at least one of conjugated, attached, linked, mixed with, encapsulated within, or encapsulating at least one of cell growth and/or trophic factor, cell guiding and cell selective agent.

In more specific embodiments, the magnetic beads may be conjugated, attached, linked either directly by chemical and non-chemical bonding or alternatively, indirectly via a linker or linking moiety, e.g., PEG used herein.

In some further embodiments, the magnetic particles conjugated, attached, linked, mixed with, encapsulated within, or encapsulating at least one of cell growth and/or trophic factor, cell guiding and cell selective agent, may be coated magnetic particles.

In some embodiments, the magnetic particles conjugated, attached, linked, mixed with, encapsulated within, or encapsulating at least one of cell growth and/or trophic factor, cell guiding and cell selective agent, may be uncoated magnetic particles. The term "conjugation" or "association" may be used interchangeably with the term "entrapped", "attachment", "linked", "embedded", "absorbed" and the like, and contemplates any manner by which the at least one bioactive agent or moiety is held by or within the magnetic nanoparticles used by the present invention. This may include for example, physical, chemical or non-chemical attachment to the carrier. In some embodiments, chemical attachment may be via a linker, such as polyethylene glycol.

The linker can be composed of any assembly of atoms, including oligomeric and polymeric chains, which functions to connect one or more of the magnetic beads to a specific bioactive agent. In some cases, the linker may be an oligomeric and polymeric chain, such as an oligo- or polyethylene glycol chain, or an oligo- or poly(amino acid) chain.

In many cases, the linker may be a linear chain, however, in some embodiments, the linker/s may contain one or more branch points. In the case of branched linker, the terminus of each branch point can be functionalized with a bioactive agent.

One or more ends of the linking group may include a functional group used to facilitate attachment of a bioactive agent and a magnetic bead. The functional group may be an atom or group of atoms that contains at least one atom that is neither carbon nor hydrogen. In some embodiments, the functional group may be a halo functional group, such as a fluoro, chloro, bromo, or iodo group; an oxygen-containing functional group, such as a hydroxyl, carbonyl, aldehyde, acetal, hemiacetal, hemiketal, ester, orthoester, carboxylic acid, carboxylate, or ether group; a nitrogen-containing functional group, such as an amide, amine, imine, azide, cyanate, nitrate, nitrile, nitrite, or pyridyl group; phosphorus containing functional groups, such as a phosphate or phosphono group; or a sulfur-containing functional group, such as a sulfide, sulfonyl, sulfonamido, sulfino, sulfo, sulfinyl, sulfhydryl, carbonothioyl, or disulfide group.

In some embodiments, the functional group may be a carboxylic acid, a chemical moiety which can be derived from a carboxylic acid by one or more chemical reactions (such as a condensation reaction to form an ester, amide, or thioester, or a reduction reaction to form an aldehyde or alcohol), an analog of a carboxylic acid in which one or more of the atoms is replaced by a sulfur atom, or an analog of a chemical moiety which could be derived from a carboxylic acid by one or more chemical reactions in which one or more of the atoms is replaced by a sulfur atom. In certain embodiments, the functional group may be a secondary amide, tertiary amide, secondary carbamate, tertiary carbamate, urea, carbinol, ether, carboxylic acid, or ester.

In some embodiments, the magnetic beads of the method of the invention may be conjugated, attached, linked, mixed with, encapsulated within, or encapsulating at least one cell growth factor.

A growth factor as used herein is a naturally occurring substance acting as a signaling molecule, capable of stimulating cellular growth, proliferation, healing, and cellular differentiation. Usually it is a protein or a steroid hormone. Growth factors are important for regulating a variety of cellular processes.

In some specific embodiments, such growth factor may be Nerve Growth Factor (NGF). More specifically, Nerve growth factor (NGF) is a neurotrophic factor and neuropeptide primarily involved in the regulation of growth, maintenance, proliferation, and survival of certain target neurons. NGF is initially in a 130-kDa complex of 3 proteins—Alpha-NGF, Beta-NGF, and Gamma-NGF (2:1:2 ratio) when expressed. This form of NGF is also referred to as proNGF (NGF precursor). The gamma subunit of this complex acts as a serine protease, and cleaves the N-terminal of the beta subunit, thereby activating the protein into functional NGF.

Still further, "Nerve trophic factors" as defined herein refer to proteins able to stimulate survival and growth of nerve cells. Most of the characterized actions of nerve trophic actors relate to developmental events and suggest that the temporal and local regulation of expression of these proteins plays a role during maturation of the nervous system. Nerve trophic factors are also important in the function of the adult nervous system for the maintenance of structural integrity and regulation of plasticity. Such processes are altered by diseases and neurodegenerative events following acute injury to the nervous system. This has prompted speculation that nerve trophic factors are involved in the structural alterations which occur in response to injury and disease.

Nerve trophic factors are found among several protein families, including neurotrophins, fibroblast growth factors, the epidermal growth factor protein family, and lymphokines to name but a few. Nerve growth factor (NGF) is the best characterized member of the nerve trophic factor protein families NGF belongs to the protein family called neurotrophins, the other known members of which are brain-derived neurotrophic factor (BDNF), neurotrophin-3 (NT-3), neurotrophin-4 (NT-4), and neurotrophin-5 (NT-5). Individual neurotrophins are highly conserved among mammalian species and share at least about 50% amino acid sequence homology with each other known member of this group. Specifically, for use herein are nerve trophic factors having amino acid sequences that comprise a sequence sharing at least about 50%, preferably at least about 60%, homology with each of the sequences of human NGF, human BDNF, human NT-3, human NT-4, and human NT-5. In yet some further specific and non-limiting embodiments, a human NGF may be used by the invention. In more specific embodiments the NGF used by the method of the invention may comprise an amino acid sequence as denoted by Accession number: CAA37703. In yet more specific embodiments, the NGF used in the methods and kits of the invention may comprise the amino acid sequence as denoted by SEQ ID NO. 5, and encoded by the nucleic acid sequence as denoted by SEQ ID N. 6.

Alternatively, mammalian nerve trophic factors can be used herein that have amino acid sequences comprising six cysteine residues in relative positions that are strictly conserved and in common with the sequences of the currently known nerve trophic factors of rats, humans, chickens, and frogs (*Xenopus*).

In yet some specific embodiments, further growth factors that may be linked, conjugated or attached to the nanoparticles used by the method of the invention may include but are not limited to, Ang-1 for repair of blood vessel, heart, and muscle that promotes maturation and stability of blood vessel; BMP-2 for repair of bone and cartilage that promotes migration of osteoblasts; BMP-7 for repair of Bone, cartilage and kidney that enhances differentiation and migration of osteoblasts, as well as renal development; BMP-9 for repair of bone that enhances osteogenic differentiation and bone formation; EGF for repair of dermal tissue, epithelia tissue, and nerve healing that maintains epithelial cell growth, proliferation and differentiation; EPO for repair of nerve, spine, and wound healing that promotes the survival of red blood cells and development of precursors to red blood cells and protects the myocardium from ischemic injury; G-CSF; GM-CSF for repair of epithelial tissues, circulating leukocytes, act as a paracrine fashion to recruit circulating neutrophils, monocytes and lymphocytes to enhance their functions in host defense; HGF for repair of bone, liver, and muscle that promotes proliferation and migration of cells; IGF-1 for repair of muscle, bone, cartilage, liver, lung, kidney, nerve, and skin that enables cell proliferation and inhibition of cell apoptosis; GDF-5 for repair of the central nervous system that increases the survival of neurons; GDF-8 (myostatin) for repair of muscle that controls the growth and differentiation of muscle cells; GDF-10 for skeletal repair that enhances skeletal morphogenesis; GDF-11 for repair of muscle that promotes regenerative capacity of satellite cells; NGF for repair of nerve, spine, and brain that promotes survival and proliferation of neural cells; TGF-α for repair of brain and skin that assists proliferation of basal cells or neural cells; TGF-β for repair of bone and cartilage that enhances proliferation and differentiation of bone-forming cells, anti-proliferative factor for epithelial cells. Further suitable growth factors may include somatomedins (somatomedin-C), platelet derived growth factors (PDGF), hepatocytic growth factors, keratinocyte growth factors, and any combinations thereof. It should be understood that the exact composition of the growth factors or any other bioactive agent/s that may be used and linked to the nanoparticles used by the methods of the invention, may be elected by the skilled artisan in accordance with the therapeutic need.

In yet some further embodiments, the magnetic beads of the invention may be conjugated or attached to any trophic factor. A "trophic factor" can be generally defined as any molecule that supports the survival of cells. Nerve growth factors are polypeptides that regulate the proliferation, survival, migration, and differentiation of cells in the nervous system. More specifically, the survival of neurons is regulated by survival factors, called neurotrophic factors. It should be noted that any neurotrophic factor may be used by the methods of the invention (specifically, attached to the nanoparticles of the invention). In yet some non-limiting examples, such neurotrophic factors include, but are not limited to, Nerve Growth Factor (NGF): there are three NGF-related trophic factors: BDNF, NT3, and NT4, which regulate survival of various neuronal populations. The Trk receptor tyrosine kinase proteins act as receptors for NGF and related factors. Trk dimerization and phosphorylation leads to activation of various intracellular signaling pathways including the MAP kinase, Akt, and PKC pathways, thereby regulating neuronal cells. Ciliary neurotrophic factor (CNTF) is another protein that acts as a survival factor for motor neurons. CNTF acts via a receptor complex that includes CNTFRα, GP130, and LIFRβ. Activation of the receptor leads to phosphorylation and recruitment of the JAK kinase, which in turn phosphorylates LIFRβ. LIFRβ acts as a docking site for the STAT transcription factors. JAK kinase phosphorylates STAT proteins, which dissociate from the receptor and translocate to the nucleus to regulate gene expression.

Glial derived neurotrophic factor (GDNF) is a member of the TGFb family of proteins, and is a potent trophic factor for striatal neurons. The functional receptor is a heterodimer, composed of type 1 and type 2 receptors. Activation of the type 1 receptor leads to phosphorylation of Smad proteins, which translocate to the nucleus to activate gene expression. As noted above, it must be appreciated that in certain embodiments, any of the neurotrophic factors discussed above or any combinations thereof, may be linked, or conjugated to, or encompassed within the magnetic nanoparticles used by the methods and kits of the invention.

In yet some further embodiments, any other types of trophic factors such as cholinergic differentiation factor/Leukemia inhibitory factor (CDF/LIF), epidermal growth factor (EGF), insulin-like growth factor (IGF), basic fibroblast growth factor (bFGF), platelet-derived growth factor (PDGF) and the like, may be linked, conjugated or encompassed by the magnetic nanoparticles used by the methods and kits of the invention.

Still further, in some embodiments, the magnetic nanoparticles used by the methods and kits of the invention may be linked, conjugated or encompass at least one axon guiding compound. Axon guidance is a process by which neurons send out axons to reach the correct targets. More specifically, axons often follow very precise paths in the nervous system, guided by specific factors. Growing axons have a highly motile structure at the growing tip called the growth cone, which "sense" the extracurricular activities in the environment for signals that instruct the axon which direction to grow. These signals, called guidance cues, can be fixed in place or diffusible and they either can attract or repel axons. Growth cones contain receptors that recognize these guidance cues and interpret the signal into a chemotropic response. The general theoretical framework is that when a growth cone "senses" a guidance cue, the receptors activate various signaling molecules in the growth cone that eventually affect the cytoskeleton.

Several important classes of axon guidance molecules and their receptors useful in the methods and kits of the invention include but are not limited to Netrins: Netrins (and neogenins) are secreted molecules that can act to attract or repel axons by binding to their receptors, DCC and UNC5.

Slits aka Sli: Secreted proteins that normally repel growth cones by engaging Robo (Roundabout) class receptors.

Ephrins: Ephrins are cell surface molecules that activate Eph receptors on the surface of other cells. This interaction can be attractive or repulsive. In some cases, Ephrins can also act as receptors by transducing a signal into the expressing cell, while Ephs act as the ligands. Signaling into both the Ephrin- and Eph-bearing cells is called "bi-directional signaling."

Semaphorins: The many types of Semaphorins are primarily axonal repellents, and activate complexes of cell-surface receptors called Plexins and Neuropilins.

Cell adhesion molecules (CAMs): are integral membrane proteins mediating adhesion between growing axons and eliciting intracellular signaling within the growth cone. CAMs are the major class of proteins mediating correct axonal navigation of axons growing on axons (fasciculation). There are two CAM subgroups: IgSF-CAMs (belonging to the immunoglobulin superfamily) and Cadherins (Ca-dependent CAMs). It should be appreciated that any of the axon guiding factors described herein or any combinations thereof may be attached, conjugated or linked to the magnetic particles used by the methods and kits of the invention.

In addition, many other classes of extracellular molecules are used by nerve growth cones to navigate properly: developmental morphogens, such as BMPs, Wnts, Hedgehog, and FGFs; extracellular matrix and adhesion molecules such as laminin, tenascins, proteoglycans, N-CAM, and L1; growth factors like NGF; neurotransmitters and modulators like GABA. In some embodiments, any one of the factors mentioned herein may be conjugated or linked to the magnetic beads used by the invention.

In yet some further embodiments, the magnetic particles of the invention may be further connected, conjugated, linked or attached to any further bioactive material or agent. Suitable bioactive agents include, but are not limited to, tissue growth enhancing substances such as growth factors, angiogenic factors, immune system suppressors such as anti-inflammatory agents, antibiotics, cell-binding proteins and peptides, and the like and growth factors as indicated above.

In some embodiments, the core diameter of the magnetic particles of the method of the invention, may range between about 0.1 nm to 100 μm. More specifically, 0.1, 0.2, 0.3, 0.4, 0.5, 0.6, 0.7, 0.8, 0.9, 1, 2, 3, 4, 5, 6, 7, 8 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1000 nm that is 1 μm, and further 1, 2, 3, 4, 5, 6, 7, 8 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 μm or more.

In some specific embodiments, the core diameter of the magnetic particles may ranges between about 1 nm to 1 μm. In more specific embodiments, the dry diameter of the magnetic particles may be 10 nm. In yet some further embodiments, the dry diameter of the magnetic particles may be 20 nm. In still further embodiments, the dry diameter of the magnetic particles may be 50 nm. In yet some further embodiments, the hydrodynamic diameter of the magnetic particles may be 100 nm.

It should be appreciated that the biomaterial used by the methods and kits of the invention may comprise one or more types of magnetic particles, specifically, 1 to 10, more specifically, 1, 2, or 3 types that may vary in size, coating, composition as described before. In some specific embodiments, the biomaterial of the invention may be collagen type I. In yet some further embodiments, the collagen type I is collagen solution of 1.4 or of 3 mg/ml. In yet some further embodiments, the solution of 1.4 or of 3 mg/ml used by the method of the invention comprises cells or cell mixtures and magnetic beads having a dry diameter of about 10 nm. In yet some further embodiments, the magnetic beads used are beads having a diameter of about 20 nm or of 50 nm or of 100 nm.

As noted above, the final step of the method of the invention, step (d), involves allowing growth, or at least a partial growth of the cells and/or cell component/s along the magnetic field lines. In yet more specific embodiments, the growth of the cells is aligned and directed along the magnetic beads that were arranged and aligned during the solidification of the biomaterial, along the magnetic field lines. In yet some further embodiments, during solidification and application of the magnetic field, components of the biomaterial are also aligned along the magnetic field lines. Therefore, in some embodiments, in step (d), the cells and cell components are allowed to grow, along the aligned magnetic beads and/or aligned components of the biomaterial.

In some specific embodiments, the component/s of the biomaterial used in the method of the invention, specifically, where the biomaterial used comprise collagen, the biomaterial components may be at least one of collagen fibrils and collagen fibers.

"Collagen fibril" refers to an elongated form of collagen, composed of molecules of tropocollagen in linear array. In Type I collagen, the tropocollagen molecules are associated in periodic, staggered arrays that give the appearance of cross-banding, forming unit fibrils; these unit fibrils are aggregated in bundles to form larger fibrils, with longitudinal striations, which may themselves be aggregated into "collagen fibers".

Thus, in more specific embodiments, the alignment of the cells employed in the methods and kits of the invention may be along the aligned fibers or fibrils of the collagen and/or along the magnetic beads.

In some embodiments, the magnetic sources of the method of the invention may be portable magnetic sources. In some embodiments, said magnetic source may be comprised within a device and held by or connected to adjustable holders.

Thus, in some embodiments, the magnetic source/s provided by the invention should be removed upon solidification of the biomaterial and are therefore portable. In some specific embodiments, the magnetic sources are provided within a device and held by adjustable holders. The term "adjustable holder" refers to a holder which position can be modified in order to comply with a specific need, specifically, shape, size and distance.

Thus, in some embodiments, the distance between the magnetic source/s, optionally, held by the device holders, may be changed, thereby providing a magnetic field having the required strength. A non-limiting example for such a device or apparatus is presented by FIG. 1A. It should be therefore appreciated that the invention further encompasses such particular device, for example, the device as presented by FIG. 1A. In yet some further embodiments, the invention further encompasses and combinations of the device and the magnetic sources and/or the biomaterial of the invention.

As discussed above, the biomaterial provided by the methods and kits of the invention comprise cells, plurality of cells or cell mixtures. The term "cell" as used herein encompasses any living cell including, but not limited to any mammalian cell. Thus, in some particular embodiments, said cells may be mammalian cells.

In yet other embodiments, the cells suitable for the method of the invention may be at least one of neuronal cells or skin cells and any mixtures thereof.

In more specific embodiments, skin cells may include epidermal and dermal cells, comprising fibroblasts, keratinocytes, Langerhans cells, Merkel cells and melanocytes.

In yet some other specific embodiments, neuronal cells may comprise neurons and glial cells.

In certain embodiments, the cells suitable for the method of the invention may be epithelial cells, endothelial cells, chondrocytes, muscle cells, osteoblasts, ligament cells, tendon cells and fascia cells (ligament, tendons and fascia are made of connective tissue that includes epithelial cells, muscle cells and nerves).

The phrase "mixture of cells" or plurality of cells, as used herein refers to plurality of cells of different types e.g., at least two of skin cells, neuronal cells, epithelial cells, endothelial cells, chondrocytes, muscle cells, osteoblasts, ligament cells, tendon cells and fascia cells (ligament, tendons and fascia are made of connective tissue that includes epithelial cells, muscle cells and nerves).

As noted above, the method of the invention may guide the growth of cells or cell components. The phrase "cell component" as used herein refers to any portion, organelle, or projection from the cell body including, but not limited to, a neurite, specifically, axon and/or dendrite.

In some specific embodiments, the biomaterial provided by the methods and kits of the invention may comprise at least one neuronal cell. It should be noted that as used herein, the term neuronal cells encompass any cell of the nervous system and include, neurons and glial cells. More specifically, "Neuron" refers to an excitable cell type in the nervous system that processes and transmits information by electrochemical signaling. Neurons are the core components of the CNS (brain and spinal cord) and the peripheral nerves. "Neuronal" means pertaining to neurons. A typical neuron consists of a cell body (soma), dendrites, and an axon. The term neurite as indicated above, is used to describe either a dendrite or an axon, particularly in its undifferentiated stage. Dendrites are thin structures that arise from the cell body, often extending for hundreds of micrometers and branching multiple times, giving rise to a complex "dendritic tree". An axon (also called a nerve fiber when myelinated) is a special cellular extension (process) that arises from the cell body at a site called the axon hillock and travels for a distance, as far as 1 meter in humans or even more in other species. The cell body of a neuron frequently gives rise to multiple dendrites, but never to more than one axon.

Glial cells, also referred to herein as neuroglia or simply glia are non-neuron cells that maintain homeostasis, form myelin, and provide support and protection for neurons in the central and peripheral nervous systems. In the central nervous system, glial cells include oligodendrocytes, astrocytes, ependymal cells and microglia, and in the peripheral nervous system glial cells include Schwann cells and satellite cells. In yet some further embodiments, the method of the invention may be used for manipulating and aligning cells in scar tissue, for example, glial cells, to facilitate smooth healing of the scar tissue.

It should be therefore noted that in some embodiments, the biomaterial provided by the methods and kits of the invention may comprise any neuronal cell or any combinations thereof. In more specific embodiments, the biomaterial solution provided by the methods and kits of the invention may comprise neuron/s. In yet some further embodiments, the biomaterial provided by the methods and kits of the invention may comprise any glial cell, specifically, at least one of oligodendrocytes, astrocytes, ependymal cells, microglia and Schwann cells. In yet some further embodiments, the biomaterial provided by the methods and kits of the invention may comprise a mixture of neurons and at least one of the glial cells indicated herein.

In some embodiments, the biomaterial provided by the methods and kits of the invention may comprise skin cells.

In yet some further specific embodiments, the biomaterial provided by the methods and kits of the invention may comprise fibroblasts. Fibroblasts are cells that synthesizes the extracellular matrix and collagen, the structural framework (stroma) for animal tissues, and plays a critical role in wound healing. Fibroblasts are the most common cells of connective tissue in animals Dermal fibroblasts are cells within the dermis layer of skin which are responsible for generating connective tissue and allowing the skin to recover from injury. Using organelles (particularly the rough endoplasmic reticulum), dermal fibroblasts generate and maintain the connective tissue which unites separate cell layers. Furthermore, these dermal fibroblasts produce the protein molecules including laminin and fibronectin which comprise the extracellular matrix. By creating the extracellular matrix between the dermis and epidermis, fibroblasts allow the epithelial cells of the epidermis to affix the matrix, thereby allowing the epidermal cells to effectively join together to form the top layer of the skin. Dermal fibroblasts are derived from mesenchymal stem cells.

In yet some further embodiments, the biomaterial provided by the methods and kits of the invention may comprise keratinocytes. In further embodiments, the biomaterial provided by the methods and kits of the invention may comprise Langerhans cells. In still further embodiments, the biomaterial provided by the methods and kits of the invention may comprise Merkel cells. In some further embodiments, the biomaterial provided by the methods and kits of the invention may comprise melanocytes. As noted above, the biomaterial provided by the methods and kits of the invention may comprise a mixture of cells, thus, according to some embodiments, the biomaterial provided by the methods and kits of the invention may comprise at least two of fibroblasts, keratinocytes, Langerhans cells, Merkel cells and melanocytes. It should be noted that in certain embodiments the biomaterial provided by the methods and kits of the invention may comprise at least one type of neuronal cells as indicated above and at least one type of skin cells indicated herein.

In yet some further embodiments, the biomaterial provided by the methods and kits of the invention may comprise myocytes. A myocyte (also known as a muscle cell) is the type of cell found in muscle tissue. Myocytes are long, tubular cells that develop from myoblasts to form muscles in a process known as myogenesis. There are various specialized forms of myocytes: cardiac, skeletal, and smooth muscle cells, with various properties. The striated cells of cardiac and skeletal muscles are referred to as muscle fibers.

It should be appreciated that for repairing skin wounds, nerve injuries, as well as for rebuilding bone, cartilage, tendon, and ligament, the biomaterial of the invention can be seeded with the appropriate cells, e.g., fibroblasts, nerve cells, connective tissue cells such as osteocytes, chondrocytes, and tendon and ligament fibrocytes, and applied in the injury.

In certain embodiments, the method of the invention may be suitable for in situ guiding cell growth in a subject in need thereof.

Therefore, "in situ guiding cell growth" as generally used herein refers to the ability of a cell, a mixture of cells or cell components which are substantially not arranged prior to and at the time of administration or application, to arrange and to grow at a desired direction, at a physiological temperature, at the site of administration or application in the body site.

The term "in situ" as used herein is meant, natural or original position or place. In connection with the present invention this term reflects that the cells and the biomaterial of the invention are aligned at the exact site and within the site of the injury.

In some embodiments, the subject may be an injured subject having an injured or wounded tissue or organ. Therefore, disclosed herein are methods for providing functional tissue or organ equivalents using artificial substrates as scaffolding for cellular repair and dynamic implantation of implants adjusted to the specific site of injury. Moreover, the methods encompassed by the invention provide tailored and personalized implants directly adjusted and fitted to the injured tissue. These implants comprise cells that are directed in a specific desired functional orientation.

Thus, in yet a further aspect, the invention relates to a method of treating or repairing tissue or organ injury in a subject. More specifically, the method of the invention may comprise the steps of: (a) providing into the site of the injured tissue or organ, at least one liquid biomaterial or biomaterial solution comprising cell/s, plurality of cells, or mixture of cells and magnetic particles or any conjugate, mixture, embedment and encasement thereof or any composition or matrix comprising the same. Next, in step (b), providing at least one or at least two magnetic sources placed at a distance providing a magnetic field having a strength of between about 5 G to about 5000 G. The next step (c) involves in situ solidifying the biomaterial while applying the magnetic field. More specifically, the alignment and solidification of the biomaterial occur at the exact site of the injured tissue or organ. Solidifying the biomaterial under magnetic field provide the alignment of at least one of the magnetic particles or aggregates thereof and/or components of the biomaterial along the magnetic field lines. In some alternative embodiments the method of the invention may comprise a further step of removing the magnetic sources once the biomaterial is solid. In the next step (d) allowing growth of cells or cell component/s within the solidified biomaterial. It should be noted that the growth of the f cells or cell component/s may be oriented along the aligned magnetic particles or aggregates thereof. Alternatively, the growth of the f cells or cell component/s may be aligned along the aligned components of the biomaterial. In yet some further embodiments, the growth of the cells or cell component/s may be aligned along the aligned magnetic beads and the biomaterial components, providing the dynamically adjustable implant discussed above, that result in treating or repairing the tissue injury.

It should be noted that in some embodiments, steps (a) to (d) of the method of the invention may be repeated several times, specifically, 1, 2, 3, 4, 5, 6, 7, 8, 9, 10 times or more, thereby creating within the site of injury different layers of solidified and aligned biomaterial comprising cell/s and magnetic particles. In yet some further embodiments, the layers may be either identical or different (e.g., having different composition of at least one of biomaterial, cells and beads).

A suitable body site where growth of the cell or cell component is desired can be, but not limited to, a body tissue or cavity or any aperture. The term "aperture" and term "biological aperture" will be used interchangeably to refer to any opening, slit, hole, gap, slot, vent, cut, crevice, chink, crack, interstice etc., within a bodily tissue, whether formed as a result of injury, deterioration, disease, or surgery, which would benefit from repair or closure. Apertures can occur naturally or through disease or injury in tissue sites of organs, joints, bone, and connective tissue, e.g. tendons, ligaments, capsular ligaments, and the like, or can be formed as the result of biopsy or excision.

As used herein, the term "tissue" refers to a collection of similar cells and the intercellular substances surrounding them, united in the performance of a particular function. It will be appreciated by those of ordinary skill in the art that there are four basic tissue types in the body, epithelium; connective tissue that include blood, bone and cartilage; muscle; and nerve. The methods of the invention are applicable to injuries, wounds, cut or any aperture in any of the tissues discussed herein. Moreover, the methods of the invention provide a dynamic and adjustable solution for injuries involving different types of tissues.

More specifically, the methods of the invention are specifically applicable for treating and repairing tissue or organ injury or any aperture in a subject.

It must be understood, that in some embodiments, the methods of the invention, by aligning in situ the cells and the biomaterial of the implant created thereby, also provide an improved scarring process, that results in an improved scar. Thus, in yet some further embodiments, the biomaterial and the methods and kits of the invention may provide a biological glue that may be applicable in any cut, injury or wound as discussed by the invention.

A tissue or organ injury/lesion may be any abnormal damage or change in the tissue of an organism, usually caused by disease or trauma. Lesions can occur anywhere in the body that consists of soft tissue or osseous matter, though most frequently found in the mouth, skin, and the brain, or anywhere. Generally, lesions may be classified by the patterns they form, their size, their location, or their cause. Lesions are often classified by their tissue type or location. For example, a "skin lesion" or a "brain lesion" are named for the tissue they are found in. If there is an added significance to regions within the tissue—such as in neural injuries where different locations correspond to different neurological deficits—they are further classified by location. For example, a lesion in the central nervous system is called a central lesion, and a peripheral lesion is one located in the peripheral nervous system. It should be appreciated that the methods of the invention may be applicable for any of the lesions and injuries indicated herein.

Still further, in some embodiments, different types of connective tissue injuries and disorders addressable and treatable by the methods of the invention may include, but are not limited to:

Tears and ruptures—Tendons and ligaments are subject to tears and ruptures. Conditions that make a tear or rupture more likely include the injection of steroids into a tendon or ligament, certain diseases (such as gout or hyperparathyroidism), and having type O blood. A tear or rupture can be a serious problem and may result in excruciating pain and permanent disability if untreated.

Sprains—The joints of the body are supported by ligaments. Ligaments are strong bands of connective tissue that connect one bone to another. A sprain is a simple stretch or tear of the ligaments. The area most vulnerable to sprains are the ankles, knees, and wrists.

Strains—The bones are supported by a combination of muscles and tendons. Tendons connect muscles to bones. A strain is the result of an injury to either a muscle or a tendon. The strain may be a simple stretch in the muscle or tendon, or it may be a partial or complete tear in the muscle-and-tendon combination.

Contusions—A contusion is a bruise caused by a blow to the muscle, tendon, or ligament.

Tendonitis/Tendinosis—An inflammation in a tendon or in the covering of the tendon is called tendonitis, which is inflammation of the tendons. Tendonitis is caused by a series of small stresses that repeatedly aggravate the tendon.

Stress Fractures—When one of the bones is stressed by overuse, tiny breaks in the bone can occur. The injury is termed a stress fracture. Early symptoms may be pain and swelling in the region of the stress fracture. The bones of the lower leg and foot are particularly prone to stress fractures.

Avulsion—An avulsion is an acute tendon injury resulting from high tensile loads, in which a tendon is forcibly torn away from its attachment site on the bone. In a majority of tensile stress injuries of the musculotendinous unit, fiber tearing occurs at the musculotendinous junction producing a strain. In some other cases these fibers remains intact and the tendon pulls away from its bony attachment site. Avulsion injuries occur in regions where a large muscle attaches at a relatively small site on the bone. Thus, in some specific embodiments, the methods of the invention provide suitable solution for any of the above connective tissue injuries, specifically, when replacement of injured tissue is required.

In yet a further aspects, the invention provides a method of promoting wound healing in a subject. More specifically, the method of the invention may comprise the steps of: (a) providing into the site of the wound, and optionally, in the surrounding adjacent tissue, at least one liquid biomaterial or biomaterial solution comprising cell/s, plurality or mixture of cells and magnetic particles or any conjugate, mixture, embedment and encasement thereof or any composition or matrix comprising the same. In the next step (b), providing at least one or at least two magnetic sources placed at a distance providing a magnetic field having a strength of between about 5 G to about 5000 G. The next step (c), involves solidifying the biomaterial while applying the magnetic field, thereby aligning at least one of the magnetic particles or aggregates thereof and components of the biomaterial, along the magnetic field lines. In step (d), allowing growth or partial growth of cells or cell component/s within the solidified biomaterial. It should be noted that in some embodiments, the growth of the f cells or cell component/s may be longitudinally oriented along at least one of the aligned magnetic particles or aggregates thereof and the aligned components of the biomaterial, thereby promoting wound healing.

In another embodiment, the methods of the invention may comprise a further step of removing the magnetic sources once the biomaterial is solid.

In yet some further embodiments, the method of the invention may further repeat steps (a) to (d) at least one further time.

As used herein, the term "wound" includes, but not be limited to, various types of cuts, abrasions, lesions, slits, burns including sunburn, surgical incisions, pressure ulcers, diabetic ulcers, traumatic damage, or other injuries or maladies, which can be chronic or non-chronic.

The invention therefore encompasses in some embodiments thereof methods for wound healing and methods for promoting wound healing.

As used herein, the term "promoting wound healing" means that the rate at which an injury or wound heals is faster in a treated subject compared to an untreated subject.

More specifically, wound healing is the process by which skin or other body tissue repairs itself after trauma. In undamaged skin, the epidermis (surface layer) and dermis (deeper layer) form a protective barrier against the external environment. When the barrier is broken, an orchestrated cascade of biochemical events is set into motion to repair the damage. This process may be divided into several predictable phases:

Hemostasis: Within the first few minutes of injury, platelets in the blood begin to stick to the injured site. This activates the platelets that change into an amorphous shape, more suitable for clotting, and further involves release of chemical signals to promote clotting. This results in the activation of fibrin, which forms a mesh acting as "glue" binding platelets thereby creating a clot that serves to plug the break in the blood vessel, slowing/preventing further bleeding.

Inflammation: During this phase, damaged and dead cells are cleared out, along with bacteria and other pathogens or debris, through the process of phagocytosis. Platelet-derived growth factors are released into the wound that cause the migration and division of cells during the proliferative phase.

Proliferation (growth of new tissue): In this phase, angiogenesis, collagen deposition, granulation tissue formation, epithelialization, and wound contraction occur. In angiogenesis, vascular endothelial cells form new blood vessels. In fibroplasia and granulation tissue formation, fibroblasts grow and form a new, provisional extracellular matrix (ECM) by excreting collagen and fibronectin. Concurrently, re-epithelialization of the epidermis occurs, in which epithelial cells proliferate and 'crawl' atop the wound bed, providing cover for the new tissue. In wound contraction, myofibroblasts decrease the size of the wound by gripping the wound edges and contracting using a mechanism that resembles that in smooth muscle cells.

Maturation (remodeling): During maturation and remodeling, collagen is realigned along tension lines, and cells that are no longer needed are removed by programmed cell death, thereby wound healing is completed. It should be appreciated that the methods of the invention may be applicable and relevant for each stage of wound healing, by promoting and facilitating the creation of a fully compatible implant perfectly adjusted to the wound, thereby providing a physical closure of the wounded tissue, that may be equivalent to the first stage of wound healing. Moreover, by providing cells and biomaterial as discussed herein before, the method of the invention may promote the proliferation and the angiogenesis stage, facilitating the growth of cells in the dynamic implant, in an aligned desirable orientation.

More specifically, the invention further provides an adjustable and compatible implant that is encompassed and prepared by the kits and methods of the invention for repairing biological apertures and injuries in situ. A specific implant as discussed above, may comprise the biomaterial of the invention that may comprise a material which further permits tissue ingrowth, such as fibrous tissue, into the material from the tissue immediately surrounding the aperture or wound. Specifically, the biomaterial used by the methods and kits of the invention may be porous. In some embodiments, the biomaterial of the invention that forms an implant upon in situ solidification and alignment of the magnetic beads, cells or cell component/s and biomaterial components, may enable ingrowth of the surrounding tissue. The term "tissue ingrowth" will refer to the growth of autologous or heterologous tissue, including tissue from any of the following sources: the patient's own natural tissue (e.g., surrounding the aperture itself), tissue from another site that is transplanted to the site (e.g., covering the implant), and cells seeded into the implant as described herein. Such ingrowth can be natural and/or induced. Tissue growth can occur, for instance, as a natural healing response to the presence of an implant as described herein, and/or in response to the use of bioactive agents, such as growth factors and the like, that may be as discussed herein before, attached or conjugated to the magnetic beads, or alternatively (or additionally) comprised within the biomaterial provided by the methods and kits of the invention.

In yet some further embodiments, the implants of the invention exhibits sufficient porosity to support tissue ingrowth as discussed above. The term "porosity", and inflections thereof, as used with regard to the implant of the present invention, will refer to a three-dimensional structure that permits or facilitates tissue ingrowth when placed and prepared within the body. Such three-dimensional structures include matrices such as open cells or channels, fibrous structures, textures having increased surface area, and the like. as noted above, in certain embodiments multiple MNPs can be mixed with different sizes to reach multiple layers in one magnetic field application. As for skin wounds, the orientation of the magnetic aggregates and collagen fibers can be modified according to need, for faster recovery (align the lines perpendicular to injured site) or for smooth skin regrowth (align along the cut, in parallel).

According to some embodiments, the liquid biomaterial used by the methods of the invention may be liquid hydrogel.

In yet some specific embodiments, the hydrogel used by the methods of the invention may be a collagen solution.

In some specific embodiments, the collagen used by the methods of the invention is collagen type I. It should be noted that any of the collagen types discussed herein before for any other aspects of the invention, may be applicable for this aspect as well.

In some embodiments, the concentration of the collagen solution may range between about 0.1 to about 10 mg/ml. Specifically, in some embodiments, a collagen solution having a concentration of 0.1, 0.2, 0.3, 0.4, 0.5, 0.6, 0.7, 0.8, 0.9, 1.1, 1.2, 1.3, 1.4, 1.5, 1.6, 1.7, 1.8, 1.9, 2, 2.5, 3, 3.5, 4, 4.5, 5, 5.5, 6, 6.5, 7, 7.5, 8, 8.5, 9, 9.5, 10 mg/ml or more, may be used. In more specific embodiments, a collagen solution of 1.4 mg/ml is used in the methods and kits of the invention. In yet some more specific embodiments, a collagen solution of 3 mg/ml is used in the methods and kits of the invention.

In some further embodiments, magnetic particles suitable for the methods of the invention, may be particles composed of any one of a magnetite core, a maghemite core, Ferrite core or iron oxide core.

In certain embodiments, magnetic particles suitable for the method of the invention, may be uncoated or coated magnetic particles.

In yet another embodiment, magnetic particles suitable for the method of the invention may be uncoated magnetic particles.

In yet another embodiment, magnetic particles suitable for the method of the invention may be coated magnetic particles.

In yet another embodiment, the magnetic particles of the method of the invention may be oleic acid-sodium salt coated magnetic particles.

In some embodiments, the magnetic particles may be coated particles, specifically, coated with anyone dextran, polyvinyl alcohol (PVA), polyethylenimine (PEI), silica, dextransulfate, starch, citric acid salt, PEG/Amine, Chitosan, Streptavidin, or Oleic acid sodium salt. In yet some specific embodiments, any magnetic particles of any size used by the methods and kits of the invention, specifically, in case of micro-particles, may be coated particles, provided that said coating is not a Streptavidin coating.

In other embodiments, the magnetic beads suitable for the method of the invention may be at least one of conjugated, attached, linked, mixed with, encapsulated within, or encapsulating at least one of cell growth and/or trophic factor, cell guiding and cell selective agent.

In more specific embodiments, the magnetic beads may be conjugated, attached, linked either directly by chemical and non-chemical bonding or alternatively, indirectly via a linker or linking moiety, e.g., PEG used herein.

It should be appreciated that any of the growth factors discussed herein before in connection with other aspects of the invention, may be applicable in the present aspect of the invention as well.

In some embodiments, the magnetic beads of the method of the invention may be conjugated, attached, linked, mixed with, encapsulated within, or encapsulating at least one cell growth factor.

In some specific embodiments, such growth factor may be Nerve Growth Factor In yet some further specific embodiments, the NGF may be conjugated to the magnetic beads used by the invention, specifically via a linker. In yet some further specific embodiments, such specific linker may be PEG.

In some embodiments, the diameter of the magnetic particles of the method of the invention, may range between about 0.1 nm to 100 μm.

In some specific embodiments, the diameter of the magnetic particles may ranges between about 1 nm to 1 μm. In more specific embodiments, the dry diameter of the magnetic particles may be 10 nm. In yet some further embodiments, the diameter of the magnetic particles may be 20 nm. In still further embodiments, the dry diameter of the magnetic particles may be 50 nm. In yet some further embodiments, the diameter of the magnetic particles may be 100 nm.

As indicated above, the methods of the invention involve the step of alignment of the magnetic beads and/or components of the biomaterial, along the lines of the magnetic field applied in situ on the biomaterial during solidification thereof.

Thus, in other embodiments, the component/s of the biomaterial used in the methods of the invention may be at least one of collagen fibrils and collagen fibers.

In some embodiments, the at least one or at least two magnetic sources used by the methods of the invention to provide a magnetic field having the desired strength as specified, may be external magnets. Such magnets in some embodiments may be placed outside of a subject's body to create an external source of magnetic field around or adjacent to the target injured tissue or organ.

In some embodiments, the magnetic sources of the method of the invention may be portable magnetic sources. In yet some further embodiments, such magnetic sources may be comprised within a device and held by or connected to adjustable holders.

It should be noted that in certain embodiments, these external portable magnetic source/s may be applicable in case of treating wounds or injuries in the skin or in any external tissue or organ. However, in some embodiments, the portable magnets may be also applicable for internal wound or tissue repair performed during a surgery. It should be understood that upon solidification and alignment of the magnetic beads and biomaterial components, the portable magnets are removed.

In some embodiments, the magnets are placed inside the body using surgical or percutaneous methods inside the target tissue, or outside the target tissue (e.g., around or adjacent to the target tissue).

As noted herein before, the biomaterial used by the invention of the invention can be applied using a biodegradable adjustable mold, which can provide a temporary border or cutaneous reconstruction to prevent evaporation and provide protection from the environment while the aligned solidified biomaterial is forming.

In certain embodiments, the liquid biomaterial of the methods of the invention may be provided and placed in the injured tissue within an adjustable biodegradable mold.

It should be noted that in some embodiments, the use of the optional biodegradable adjustable mold may be particularly suitable when the wound or injured tissue lacks adjacent surrounding tissue that holds the biomaterial solution applied in situ, until it is solidified.

Biodegradability of polymer molds plays an important role in tissue repair. They act to temporary hold the biomaterial solution in place until it has sufficiently solidified and aligned. The mold breakdowns into nontoxic degradable products which are capable of being disposed of by the body leaving behind the newly formed tissue. Biologically degradable material may be made in some particular and non-limiting examples from the following polymers: Synthetic polymers such as poly(glycolic) acid, poly(lactic acid); in general: glycolic- and lactic acid based polymers and copolymers, poly caprolactones; in general: poly hydroxyl alkanoates (PHAs), (poly(hydroxy alcanoic acids) all polyester), poly (ethylene glycol), poly vinyl alcohol, poly (orthoesters), poly (anhydrides), poly (carbonates), poly amides, poly imides, poly imines, poly (imino carbonates), poly (ethylene imines), polydioxanes, poly oxyethylene (poly ethylene oxide), poly (phosphazenes), poly sulphones, poly acrylic acids, poly methylmethacrylate (PMMA), poly acryl amides, poly acrylo nitriles, (poly cyano acrylates), poly HEMA, poly urethanes, poly olefins, poly styrene, poly terephthalates, poly fluorides, poly ethylenes, poly propylenes, poly ether ketones, poly vinylchlorides, silicones, poly silicates (bioactive glass), siloxanes (poly dimethyl siloxanes), hydroxyapatites, natural derived polymers such as poly aminoacids (natural and non-natural), polyesters, poly beta-aminoesters; in general: poly (peptides) such as albumines, alginates, cellulose, cellulosic biocomposites, cellulose acetates, chitin, chitosan, collagene, fibrine/fibrinogen, gelatine, lignine, starch composites with low, medium or high amount of starch; soy-based plastics, neutral polysaccharides (gellan gum, pullulan, laminarin and curdlan). Protein based polymers such as poly (lysine), poly (glutamate), poly (malonates), poly (hyaluronic acids), poly nucleic acids, poly saccharides, poly (hydroxyalkanoates), poly isoprenoids, starch based polymers and that all copolymers thereof, as linear, branched, hyperbranched, dendrimers, crosslinked, functionalized (surface, functional groups, hydrophilic-hydrophobic).

In yet some specific embodiments, a biodegradable mold of any adjustable hollow shape (tube, cigar, free-shape, etc.) may be inserted inside the cavity of the injured tissue in order to allow a delayed introduction or application and positioning of the biomaterial solution of the invention, seconds, minutes, hours, days, weeks, months, after the intervention, inside a cavity well defined by the biodegradable mold.

The tissue repair adjustable biodegradable mold that may be optionally used by the method of the invention, functioning as a substitute body part, may be flat, tubular, or of complex geometry. The shape of the biodegradable mold may will be decided by its intended use and formed and adjusted within the injury site. Thus, when or before forming the implant of the invention or any layers thereof, the mold or plate can be fashioned in situ to accommodate the desired shape, thereby being adjustable mold.

It should be appreciated that the tissue repair biomaterial solution of the invention can be implanted to repair, augment, or replace diseased or damaged organs, such as abdominal wall defects, pericardium, hernias, and various other organs and structures including, but not limited to, bone, periosteum, perichondrium, intervertebral disc, articular cartilage, dermis, epidermis, bowel, ligaments, and tendons.

It must be understood that in certain embodiments, the biomaterial of the invention, as well as the optional mold, may be made of a biocompatible material. The term "biocompatible" means that the polymer is non-toxic, non-mutagenic and, at most, elicits only a minimal to moderate inflammatory reaction. The term "biodegradable", when referred to the optional mold, means that the polymer either degrades or is resorbed after implantation into products that are used by, or are otherwise eliminated from, the body by existing biochemical pathways.

It should be further appreciated that the number and configuration of implant formed in situ using the biomaterial solution provided by the methods and kits of the invention, can be varied or altered according to the specific patient's needs. In order to optimize the compliancy of the implant to the tissue site, the biomaterial solution is provided in liquid form into the aperture and thus can itself be adjusted to perfectly fit the aperture, cut, wound or injury. In case of multiple injuries, more than one implant can be implanted at the respective tissue sites, as described herein.

As indicated above, any cell, plurality of cells, or any mixture of different cell types may be used in the biomaterial of the invention. In some embodiments, the cells are of a mammalian origin, thus, any mammalian cell may be used. In some exemplary embodiments for rebuilding and repairing skin, neuronal tissue, bone, cartilage, tendon, and ligament, the biomaterial of the invention can be seeded with the appropriate cells, and applied in the injury. In some specific embodiments, such mixtures may include any relevant cell type e.g., skin cells such as fibroblasts, keratinocytes, Langerhans cells, Merkel cells and melanocytes, neuronal cells, such as neurons and glia cells, connective tissue cells such as osteocytes, chondrocytes, and tendon and ligament fibrocytes.

In yet other embodiments, the cells suitable for the methods of the invention may be at least one of neuronal cells or skin cells.

In more specific embodiments, the cells suitable for the methods of the invention may be of an autologous or allogenic source.

Thus, in some embodiments, the cells encompassed by the biomaterial solution used by the methods and kits of the invention may be cells of an autologous source. The term "autologous" when relating to the source of cells, refers to cells derived or transferred from the same subject that is to be treated with the biomaterial.

In yet a further embodiments, the cells encompassed by the biomaterial solution used by the methods and kits of the invention may be cells of an allogenic source.

The term "allogenic" when relating to the source of cells, refers to cells derived or transferred from a different subject, referred to herein as a donor, of the same species.

Thus, the method of the invention may be applicable for the treatment, repair and replacement of any tissue, and as such, the biomaterial solution provided by the kits and methods of the invention may be seeded with variety of cells for complete recovery of the injured tissue.

Mammals suffer tissue loss from a variety of mechanisms including trauma, tumor removal, vascular disease, genetic defects, cosmetic surgery and infections. Replacement of lost tissue or organs is often essential for either survival or function of the mammal Many mammalian tissues can be thought of as multi-layer constructs. The surface layer contacts the environment or one or more body fluids, and the stromal layer provides mechanical support and a vascular supply to the surface layer (s). These multi-layer tissue types include skin, trachea, bronchi, vermillion, oral lining, nasal lining, stomach, intestines, biliary ducts, ureters, bladder and blood vessels. When replacing any of these tissues or structures, it is essential that all layers (e.g., the stromal and surface layers) be reconstituted. The methods and kits of the invention address such needs. More specifically, by enabling the optional preparation of different tissue layers, by repeating steps (a) to (d) of the method, the invention provides powerful and flexible personalized treatments of wound as will be detailed herein after.

In some embodiments, the injured tissue may involve skin. Thus, the method of the invention may be particularly applicable for repairing and treating injured skin. It should be noted that the skin is composed of multiple layers of cells and tissues, which are held to underlying structures by connective tissue. The deeper layer of skin is well vascularized (has numerous blood vessels). It also has numerous sensory, and autonomic and sympathetic nerve fibers ensuring communication to and from the brain.

The epidermis is composed of keratinized, stratified squamous epithelium. It is made of four or five layers of epithelial cells, depending on its location in the body. It does not have any blood vessels within it (i.e., it is avascular). Skin that has four layers of cells is referred to as "thin skin." From deep to superficial, these layers are the stratum basale, stratum spinosum, stratum granulosum, and stratum corneum. Most of the skin can be classified as thin skin. "Thick skin" is found only on the palms of the hands and the soles of the feet. It has a fifth layer, called the stratum lucidum, located between the stratum corneum and the stratum granulosum. The cells in all of the layers except the stratum basale are called keratinocytes. A keratinocyte is a cell that manufactures and stores the protein keratin. Keratin is an intracellular fibrous protein that gives hair, nails, and skin their hardness and water-resistant properties. The keratinocytes in the stratum corneum are dead and regularly slough away, being replaced by cells from the deeper layers.

The stratum basale (also called the stratum germinativum) is the deepest epidermal layer and attaches the epidermis to the basal lamina, below which lie the layers of the dermis. The cells in the stratum basale bond to the dermis via intertwining collagen fibers, referred to as the basement membrane. A finger-like projection, or fold, known as the dermal papilla is found in the superficial portion of the dermis. Dermal papillae increase the strength of the connection between the epidermis and dermis; the greater the folding, the stronger the connections made. The stratum basale is a single layer of cells primarily made of basal cells. A basal cell is a cuboidal-shaped stem cell that is a precursor of the keratinocytes of the epidermis. All of the keratinocytes are produced from this single layer of cells, which are constantly going through mitosis to produce new cells. As new cells are formed, the existing cells are pushed superficially away from the stratum basale. Two other cell types are found dispersed among the basal cells in the stratum basale. The first is a Merkel cell, which functions as a receptor and is responsible for stimulating sensory nerves that the brain perceives as touch. These cells are especially abundant on the surfaces of the hands and feet. The second is a melanocyte, a cell that produces the pigment melanin. Melanin gives hair and skin its color, and also helps protect the living cells of the epidermis from ultraviolet (UV) radiation damage.

As the name suggests, the stratum spinosum is spiny in appearance due to the protruding cell processes that join the cells via a structure called a desmosome. The desmosomes interlock with each other and strengthen the bond between the cells. The stratum spinosum is composed of eight to 10 layers of keratinocytes, formed as a result of cell division in the stratum basale. Interspersed among the keratinocytes of this layer is a type of dendritic cell called the Langerhans cell, which functions as a macrophage by engulfing bacteria, foreign particles, and damaged cells that occur in this layer. The keratinocytes in the stratum spinosum begin the synthesis of keratin and release a water-repelling glycolipid that helps prevent water loss from the body, making the skin relatively waterproof. As new keratinocytes are produced atop the stratum basale, the keratinocytes of the stratum spinosum are pushed into the stratum granulosum.

The stratum granulosum has a grainy appearance due to further changes to the keratinocytes as they are pushed from the stratum spinosum. The cells (three to five layers deep) become flatter, their cell membranes thicken, and they generate large amounts of the proteins keratin, which is fibrous, and keratohyalin, which accumulates as lamellar granules within the cells. These two proteins make up the bulk of the keratinocyte mass in the stratum granulosum and give the layer its grainy appearance. The nuclei and other cell organelles disintegrate as the cells die, leaving behind the keratin, keratohyalin, and cell membranes that will form the stratum lucidum, the stratum corneum, and the accessory structures of hair and nails.

The stratum lucidum is a smooth, seemingly translucent layer of the epidermis located just above the stratum granulosum and below the stratum corneum. This thin layer of cells is found only in the thick skin of the palms, soles, and digits. The keratinocytes that compose the stratum lucidum are dead and flattened. These cells are densely packed with eleiden, a clear protein rich in lipids, derived from keratohyalin, which gives these cells their transparent (i.e., lucid) appearance and provides a barrier to water.

The stratum corneum is the most superficial layer of the epidermis and is the layer exposed to the outside environment. The increased keratinization (also called cornification) of the cells in this layer gives it its name. There are usually 15 to 30 layers of cells in the stratum corneum. This dry, dead layer helps prevent the penetration of microbes and the dehydration of underlying tissues, and provides a mechanical protection against abrasion for the more delicate, underlying layers. Cells in this layer are shed periodically and are replaced by cells pushed up from the stratum granulosum (or stratum lucidum in the case of the palms and soles of feet).

The dermis might be considered the "core" of the integumentary system. It contains blood and lymph vessels, nerves, and other structures, such as hair follicles and sweat glands. The dermis is made of two layers of connective tissue that compose an interconnected mesh of elastin and collagenous fibers, produced by fibroblasts.

The papillary layer is made of loose, areolar connective tissue, which means the collagen and elastin fibers of this layer form a loose mesh. This superficial layer of the dermis projects into the stratum basale of the epidermis to form finger-like dermal papillae. Within the papillary layer are fibroblasts, a small number of fat cells (adipocytes), and an abundance of small blood vessels. In addition, the papillary layer contains phagocytes, defensive cells that help fight bacteria or other infections that have breached the skin. This layer also contains lymphatic capillaries, nerve fibers, and touch receptors called the Meissner corpuscles. Thus, for replacing, repairing or reconstructing this layer, the biomaterial of the invention may comprise a mixture of at least two of fibroblasts, adipocytes and nerve cells.

Underlying the papillary layer is the much thicker reticular layer, composed of dense, irregular connective tissue. This layer is well vascularized and has a rich sensory and sympathetic nerve supply. The reticular layer appears reticulated due to a tight meshwork of fibers. Elastin fibers provide some elasticity to the skin, enabling movement. Collagen fibers provide structure and tensile strength, with strands of collagen extending into both the papillary layer and the hypodermis. In addition, collagen binds water to keep the skin hydrated.

The hypodermis (also called the subcutaneous layer or superficial fascia) is a layer directly below the dermis and serves to connect the skin to the underlying fascia (fibrous tissue) of the bones and muscles. It is not strictly a part of the skin, although the border between the hypodermis and dermis can be difficult to distinguish. The hypodermis consists of well-vascularized, loose, areolar connective tissue and adipose tissue, which functions as a mode of fat storage and provides insulation and cushioning for the integument.

It must be appreciated that the multi-layer nature of different tissues and organs, for example, the skin, demonstrates one of the most important advantageous of the dynamic and compatible methods and kits of the invention. In case of injury in the skin, the method of the invention provides suitable solution for the multi-layer nature of the skin that depends on the depth of the injury and the extent, type and number of layers involved. More particularly, in case a skin injury involves variety of layers, the methods of the invention provides a step-by-step recovery and repair for each layer. In such specific embodiment, a biomaterial solution compatible for the deepest skin layer injured is applied first in the injured tissue. Such biomaterial may comprise specific cell population required for the specific layer. It should be also appreciated that the composition of the biomaterial used may also vary between the layers and may comprise in some embodiments, a mixture or more than one biomaterial polymer and a mixture of more than one type of magnetic particles. Upon alignment and solidification of the first layer, the next layer is applied. This layer may contain biomaterial comprising different composition of cells, different composition of magnetic beads (specifically, with different coating or size), and as noted above, even a different composition of biomaterial polymer. Upon alignment and solidification of said layer, the next layer is being applied. In such way, the wound is repaired and in some embodiments, the wounded tissue is replaced by a multi-layer implant that mimic the multi-layer nature of the original injured tissue.

Thus, it should be appreciated that the method of the invention comprise in certain embodiments, the provision of at least one biomaterial solution comprising at least one type of magnetic particles and cells, plurality of cells or cell mixtures, applied to the injured site. Upon solidification and alignment of the first layer under a magnetic field, in an optional additional step, the method of the invention further comprise the application of an additional layer of biomaterial that may be either identical or different in its composition with respect to the previous layer, particularly in composition of the cells or cell population and/or magnetic beads used. This step is repeated with further layers up to the coverage and closure of the entire wound or injured tissue.

In some specific embodiments, the method of the invention will enable solidification and alignment of one to 50 layers or more. Specifically, 1, 2, 3, 4, 5, 6, 7, 8 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 layers. In more specific embodiment, the width of the above mentioned layer is 0.1, 0.2, 0.3, 0.4, 0.5, 0.6, 0.7, 0.8, 0.9, 1, 2, 3, 4, 5, 6, 7, 8 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 nm.

In yet some further embodiments, the method of the invention may be applicable for repairing, replacing or treating any soft tissue injury. A Soft tissue injury (STI) is the damage of muscles, ligaments and tendons throughout the body. Common soft tissue injuries usually occur from a sprain, strain, a one off blow resulting in a contusion or overuse of a particular part of the body. Soft tissue injuries can result in pain, swelling, bruising and loss of function.

Still further, in certain embodiments, the methods of the invention may be suitable for repairing, replacing or treating any hard tissue injury. A hard tissue injury is damage to bone tissue. A hard tissue injury is also called a “fracture” and is defined as a “loss of continuity in the substance of a bone”. Hard tissue injuries, also known as “fractures” are commonly referred to as “broken bones”, or perhaps “cracked bones” in the case of stress fractures and hairline fractures.

There are several different types of fractures (broken bones). Some concern bones that have been completely broken (separated) into two or more pieces e.g. simple fractures and comminuted fractures, while others concern damage to bone tissue that is less severe than a complete clean break but may still be painful, e.g. hairline fractures and greenstick fractures.

In yet some further specific embodiments, the method of the invention may be applicable for repairing, replacing or treating any connective tissue injury. Connective tissues are specialized tissues, which provide support and hold the body’s tissues together. Connective tissue is made up of a small fraction of cells and a majority of extracellular substance which keeps the cells separated. The two types of cells found in connective tissue include fibrocytes (or fibroblasts) and fat cells, which are fixed cells. Additionally, the extracellular substance separating the cells is made up of three types of fibers, including collagen fibers, reticular fibers and elastic fibers. There are different types of connective tissues: cartilage, bone, adipose, blood, Hemapoetic/Lymphatic and Elastic connective tissues.

It should be understood that the methods and kits of the invention may be applicable for any of the connective tissue injuries disclosed herein above.

More specifically, in some embodiments, the method of the invention may be applicable for any injury in cartilage. Cartilage is a type of supporting connective tissue. Cartilage is a dense tough, flexible connective tissue, which act as shock absorbers, consisting of the chondrocyte cells. Cartilage connective tissue includes hyaline cartilage, fibrocartilage and elastic cartilage. The fibers in the cartilage connective tissue include collagen and elastic fibers. Cartilage connective tissue has limited ground substance and can range from semisolid to a flexible matrix. Cartilages cover the surface of joints found throughout the body and facilitate bones to slide over one another with reduced friction, and damage. There is no blood supply through cartilage unlike other tissues such as skin or muscle, which makes it difficult to regenerate damaged cartilage tissue. Articular cartilage lies between joints such as knee joints where the most common and serious damage occurs.

Still further, in certain embodiments, the methods of the invention may be applicable for injuries in the elastic connective tissue. Elastic connective tissue helps maintain blood pressure and promotes normal exhalation. Elastic connective tissues consist of chondrocytes cells and are made up of elastic fibers. The extracellular substance of elastic connective tissue is composed of limited ground substance and is structured in a flexible, but firm matrix.

In yet some further embodiments, the method of the invention may be applicable for treating and repairing injuries in the fibrous connective tissue. The fibrous connective tissue functions to provide strength to the inner layer of skin and strength, allowing it to handle forces of joint movements. Fibrous connective tissue contains fibroblast cells and is made up of fibrous fibers. It is a dense connective tissue, with its extracellular substance consisting of parallel or irregularly arranged bundles of fibers with few cells and little ground substance.

In some specific embodiments, the methods of the invention may be applicable for treating, repairing or replacing injuries in bone tissue. Bone tissue, or osseous tissue, is the major structural and supportive connective tissue of the body. Bone tissue forms the rigid part of the bones that make up the skeleton. Bones are organs that are made up of bone tissue as well as bone marrow, small blood vessels, epithelium and nerves. Bone tissue refers specifically to the bone mineral matrix that forms the rigid sections of the organ, and the bone cells within it. The two types of bone tissue are cortical bone and cancellous bone. There is another kind of tissue called subchondral bone which underlies the epiphyseal cartilage at the ends of bones. The bone cells develop new bone tissue and continual bone remodeling—maintaining the bones and the regulation of minerals in the body. Types of bone cell include osteoclasts, which break down bone tissue; osteoblasts, which build new bone tissue; osteocytes, which hold up the bone together; and lining cells, which protect the bone. It should be noted that at least one of these cell types may be included in the biomaterial solution of the invention when repairing bone tissue as indicated herein.

In yet some further specific embodiments, the methods of the invention may be applicable for treating, repairing or replacing injuries in muscle tissue. Muscle tissue is a soft tissue, and is one of the four fundamental types of tissue present in animals There are three types of muscle tissue recognized in vertebrates:

Skeletal muscle or “voluntary muscle” is anchored by tendons (or by aponeuroses at a few places) to bone and is used to effect skeletal movement such as locomotion and in maintaining posture. Though this postural control is generally maintained as an unconscious reflex, the muscles responsible react to conscious control like non-postural muscles. Smooth muscle or “involuntary muscle” is found within the walls of organs and structures such as the esophagus, stomach, intestines, bronchi, uterus, urethra, bladder, blood vessels, and the arrector pili in the skin (in which it controls erection of body hair). Unlike skeletal muscle, smooth muscle is not under conscious control.

Cardiac muscle (myocardium), is also an “involuntary muscle” but is more akin in structure to skeletal muscle, and is found only in the heart.

Cardiac and skeletal muscles are “striated” in that they contain sarcomeres that are packed into highly regular arrangements of bundles; the myofibrils of smooth muscle cells are not arranged in sarcomeres and so are not striated.

While the sarcomeres in skeletal muscles are arranged in regular, parallel bundles, cardiac muscle sarcomeres connect at branching, irregular angles (called intercalated discs). Striated muscle contracts and relaxes in short, intense bursts, whereas smooth muscle sustains longer or even near-permanent contractions.

Skeletal (voluntary) muscle is further divided into two broad types: slow twitch and fast twitch:

Type I, slow twitch, or "red" muscle, is dense with capillaries and is rich in mitochondria and myoglobin, giving the muscle tissue its characteristic red color. It can carry more oxygen and sustain aerobic activity using fats or carbohydrates as fuel. Slow twitch fibers contract for long periods of time but with little force.

Type II, fast twitch muscle, has three major subtypes (IIa, IIx, and IIb) that vary in both contractile speed and force generated. Fast twitch fibers contract quickly and powerfully but fatigue very rapidly, sustaining only short, anaerobic bursts of activity before muscle contraction becomes painful. They contribute most to muscle strength and have greater potential for increase in mass. Type IIb is anaerobic, glycolytic, "white" muscle that is least dense in mitochondria and myoglobin. In small animals (e.g., rodents) this is the major fast muscle type, explaining the pale color of their flesh.

Still further, as indicated herein, any internal or external, a tissue may be repaired or treated by the methods and kits of the invention, or replaced using the implants produced in situ using the methods and kits of the invention. Areas of tissue that have been destroyed or damaged may be surgically removed to prevent them from interfering with the healing process. The entire area of dead and damaged tissue may be thus excised, so that intact epithelial cells are present at the perimeter of the wound. The biomaterial of the invention, with the optional biodegradable mold, if present, is applied across the wound, in one or more layers, while avoiding the entrapment of air pockets between the wound and the biomaterial. Upon solidification of the biomaterial that forms an implant, the wound applied with the implant may be then covered with a bandage.

For example, abnormal tissue can be intentionally (e. g., surgically) removed from an individual and new tissue can be produced in its place using this method.

Alternatively, the method of the present invention can be used to produce new tissue in place of tissue which has been lost due to accident or disease.

The present invention has application to massively burned patients as well as to patients undergoing reconstructive surgery, tissue trauma, surgical resection, infection, chronic skin diseases and chronic wounds. The present invention will also be useful in the replacement of other specialized epithelial tissues in a variety of organ systems, including, but not limited to, bone, cartilage, oral mucosa, uroepithelial, gastrointestinal, respiratory and vascular. Tissue loss from malignancy, congenital or acquired disease and surgical removal can be replaced with tissue composed of the same specialized native cells. Specialized epithelial tissue such as bladder, ureter, oral mucosa, esophagus, trachea, blood vessel and intestine often requires replacement or reconstruction after surgical excision.

The implants and methods of preparing the same described herein can be used by the oncologic, trauma or reconstructive surgeon to replace tissue defects with a tissue composed of organ-specific cells identical to the native tissue, without the need to violate uninjured organs for donor tissue. Such tissue can be replaced after surgical resection for malignancy, disease or trauma. This method allows for replacement of various commonly lost tissues such as oropharyngeal, nasal and bronchial mucosa, lip vermillion, blood vessels, trachea, esophagus, stomach, small and large bowel, biliary ducts, ureter, bladder, urethra, periosteum, synovium, areolar tissue, chest wall, abdominal wall and vaginal mucosa. Structural defects such as ventral, inguinal and diaphragmatic hernias, replacement or augmentation of tendons, ligaments and bone and abdominal and thoracic wall reconstruction can also be repaired.

A further aspect of the invention is a therapeutic method and composition for repairing fractures and other conditions related to cartilage and/or bone defects or periodontal diseases. The invention further comprises therapeutic methods, kits and implants for wound healing and tissue repair, administering the biomaterial topically, or locally as an implant.

The term "repair" when applied to cartilage and other tissues is intended to mean without limitation repair, regeneration, reconstruction, reconstitution or bulking of tissues.

It should be appreciated that a variety of tissue types can be joined using the methods and kits of the invention. The method may thus be applicable to anastomoses of biological tubes including veins, arteries, lymphatics, nerves, vasa efferentia, fallopian tubes, bile ducts, tubes of the alimentary canal, the ureter, the urethra, tear ducts, bronchi and any other such bodily tubes as well as to repairs of incisions or tears of biological organs such as kidneys, liver or spleen, or of biological surfaces such as the peritoneum and skin. It will therefore be understood that the method can be used in a variety of join situations including the joining of cylindrical anastomoses and the closure of linear defects or injuries such as incisions.

The method of the invention can also be applicable for the repair of other discontinuities in tissue surfaces such as holes, resulting from accident or surgery. In this form of the invention the liquid biomaterial of the invention may be injected or provided otherwise into the injury site to conform to the shape of the repair site, and the edges of the repair site may not need to be aligned or abutted for the repair to be effected.

In yet a further aspect, the invention relates to a method for treating or repairing a nerve injury in a subject. More specifically, the method comprises the steps of: First in step (a), providing into the site of the nerve injury, at least one liquid biomaterial or biomaterial solution comprising neuronal cell/s, or mixture of neuronal cells and magnetic particles or any conjugate, mixture, embedment and encasement thereof or any composition or matrix comprising the same. In the next step (b), providing at least one, or at least two magnetic sources placed at a distance providing a magnetic field having a strength of between about 5 G to about 5000 G. The next step (c), involves solidifying the biomaterial while applying the magnetic field, thereby aligning at least one of the magnetic particles or aggregates thereof and components of the biomaterial, along the magnetic field lines. In the next step (d), allowing cell growth within the solidified biomaterial. The growth or partial growth of the cells is longitudinally oriented along at least one of the aligned magnetic particles or aggregates thereof and the aligned components of the biomaterial, thereby treating or repairing nerve tissue injury.

In more specific embodiments, the method of the invention may comprise a further step of removing the magnetic sources once the biomaterial is solid.

In yet some further embodiments, the method of the invention may comprise repeating steps (a) to (d) at least one more time.

In certain embodiments, the methods and kits or the invention and the implants prepared thereby, may be applicable for treating a subject suffering from any neuropathy. Neuropathy is the term used to describe a problem with the nerves, usually the 'peripheral nerves' as opposed to the 'central nervous system' (the brain and spinal cord). Neuropathy covers a wide area and many nerves and the symptoms depend on the type of affected nerves, specifically, sensory nerves, motor nerves and autonomic nerves.

As will be elaborated hereinafter, the invention provides in certain embodiments thereof, methods and kits for treating and repairing nerve injury in a subject. In some specific embodiments the methods of the invention provide regeneration or neuroregeneration of the injured nerve tissue. Nerve regeneration or neuroregeneration, refers to the regrowth or repair of nervous tissues, cells or cell products. Such mechanisms may include generation of new neurons, glia, axons, myelin, or synapses. Although neuroregeneration differs between the peripheral nervous system (PNS) and the central nervous system (CNS) by the functional mechanisms that control axon regrowth. Symptoms associated with a lack of nerve regeneration include, without limitation, abnormal movement, abnormal sensation, limb grasping, muscle weakness, atrophy, paralysis, loss of neuronal function, loss of motor neuron function, loss of sensory neuron function, inhibited neuronal growth, inhibited axon growth, inhibited synaptic plasticity, synaptic loss, astrocytic gliosis and/or glial scaring. The methods and kits of the invention as well as the implants created thereby, successfully address any of the above mentioned symptoms and conditions associated with the discussed neuronal injury.

In some embodiments, these disorders can be associated with the cell body of the neuron (which can receive signals directly), with the axons of the neuron (which generally conducts signals away from the cell body), and/or with the dendrites of the neuron (which receive signals from the axons of other neurons). The branching of the axon allows for passage of a signal to many target cells simultaneously. Similarly, dendrites can be so extensively branched as to receive as many as 100,000 inputs on a single neuron. The immense variety in the pattern of branching of axons and dendrites is characteristic of different functional classes of neurons. Neural tissue is classified as either peripheral or central. The central nervous system (CNS) comprises the brain and the spinal cord which is linked via the nerves to a large number of peripheral structures such as sense organs for input, and muscles and glands for output. Nerve cell clusters of the peripheral nervous system (PNS) are termed ganglia and are also connected via nerves to the central nervous system. All neural tissue, both peripheral and central, is made up of two major classes of cells: neurons and glial cells. Generally, once a neuron has reached maturity, it does not divide. As a result, when a neuron dies, the resulting functional deficit is not typically repaired, and the resultant pathology is irreversible. Neuronal cell death can occur in neurodegenerative diseases, neuropathies and nerve resection.

Peripheral neuropathy, including nerve resection, results from damage to neurons in the PNS. In this case, the neurons, once damaged, may or may not die. Typically, the axons of the neurons are affected, with destruction of the axon itself or the myelin sheath surrounding the axon. If the cell body of the neuron remains alive after axonal degeneration and/or demyelination, the neuron can sometimes repair itself. However, if the cell body dies, functional repair requires collateral nerve growth to compensate for the damage. Common causes of peripheral neuropathy include, for example, diabetes mellitus, chronic alcohol abuse, nutritional deficiencies (such as vitamins B and E), chronic renal failure, radiation therapy, HIV infection, and trauma or entrapment (like carpal tunnel syndrome). Entrapment of neurons can occur when surrounding structures impinge on the neuron, e. g., as a result of inflammation in the area. Peripheral neuropathy may be treated by agents which accelerate axonal repair, prevent neuronal death and induce collateral nerve growth. Nerve resection can occur during injury or trauma to the body and can also occur during surgical procedures such as when the nerve is accidentally cut. It should be understood that the invention provides methods and kits for repairing nerve injury in a subject suffering from any of the neuropathies indicated herein.

In yet some further embodiments, the method of the invention may be applicable for treating and repairing Neurotmesis. As used herein, Neurotmesis (in Greek tmesis signifies "to cut") is part of Seddon's classification scheme used to classify nerve damage. It is the most serious nerve injury in the scheme. In this type of injury, both the nerve and the nerve sheath are disrupted. Nerves are categorized into three groups based on the direction that signals are conducted: Afferent nerves conduct signals from sensory neurons to the central nervous system, for example from the mechanoreceptors in skin.

Efferent nerves conduct signals from the central nervous system along motor neurons to their target muscles and glands.

Mixed nerves contain both afferent and efferent axons, and thus conduct both incoming sensory information and outgoing muscle commands in the same bundle.

Still further, nerves can be categorized into two groups based on where they connect to the central nervous system:

Spinal nerves innervate (distribute to/stimulate) much of the body, and connect through the spinal column to the spinal cord and thus to the central nervous system. They are given letter-number designations according to the vertebra through which they connect to the spinal column.

Cranial nerves innervate parts of the head, and connect directly to the brain (especially to the brainstem).

Most typically, humans are considered to have twelve pairs of cranial nerves (I-XII). They are: the olfactory nerve (I), the optic nerve (II), oculomotor nerve (III), trochlear nerve (IV), trigeminal nerve (V), abducens nerve (VI), facial nerve (VII), vestibulocochlear nerve (VIII), glossopharyngeal nerve (IX), vagus nerve (X), accessory nerve (XI), and hypoglossal nerve (XII). (There may be a thirteenth cranial nerve, the terminal nerve (nerve O or N), which is very small and may or may not be functional in humans. It should be appreciated that in some embodiments, the method of the invention may be applicable for treating and repairing any injury or wound in any of the nerves indicated herein.

In some specific embodiments, the nerve injury may be a full cut in the sciatic nerve. The sciatic nerve provides the connection to the nervous system for nearly the whole of the skin of the leg, the muscles of the back of the thigh, and those of the leg and foot. It is derived from spinal nerves L4 to S3. It contains fibers from both the anterior and posterior divisions of the lumbosacral plexus.

Still further, in some embodiments, the invention provides methods and kits for enhancing and supporting functional and directional neurite outgrowth. As used herein, the term "neurite growth" or "neurite outgrowth" includes the process by which axons or dendrites extend from a neuron. The outgrowth can result in a new neuritic projection or in the extension of a previously existing cellular process. Neurite outgrowth may include linear extension of an axonal process by five cell-diameters or more.

In yet some further embodiments, repairing and treating nerve injury by the methods and kits of the invention may include dendritic outgrowth. As used herein, "dendrites" or "dendritic outgrowth" refers to nerve cell processes distinguishable from axons by virtue of their morphological and immunological characteristics. For example, dendrites are morphologically distinguishable in that dendrites are broad-based, exhibit a distinct taper, and branch in a "Y"-shaped pattern with daughter processes being distinctly smaller than the parent process. Additionally, dendrites are thicker than axons, and unlike axons, they terminate locally usually extending from the soma.

Still further, in some embodiments, the method of the invention may result in enhanced axonal sprouting. Axonal sprouting is a process where fine nerve processes sprouts grow out from the intact axons to reinnervate denervated muscle fibers. Thereby the sprouting sustains the nerve supply to muscles and, in turn, the ability to move.

As noted above and demonstrated by the following Examples, the invention provides effective methods for treating neuronal injury. Thus, in certain embodiments, the methods and kits of the invention may be applicable for treating a subject suffering from any neuronal or brain injury. As used herein the term "brain injury" is the destruction or degeneration of brain cells is in the brain of a living organism. Brain injuries can result from direct impacts to the head. Such injuries are for example traumatic brain injury and spinal cord injury. The present invention may also be used in treating other neuronal disorders, which include disease, disorder, or condition directly or indirectly affecting the normal functioning or anatomy of a subject's nervous system. The disorder may be a neuronal injury, which can be acute. Examples of acute injury are those that results from surgery, trauma, compression, contusion, transection or other physical injury, vascular pharmacologic or other insults including hemorrhagic or ischemic damage. The invention can be beneficial in all diseases that require regeneration or maintenance of axons, such as Traumatic brain injury (TBI) and Spinal cord injury (SCI).

In yet some further specific embodiments, the methods and kits of the invention may be applicable for treating and repairing nerve injury in a subject suffering from traumatic brain injury. Damaged areas in the brain can be filled with the biomaterial solution of the invention. "Traumatic brain injury (TBI)" as used herein includes the condition in which a traumatic blow to the head causes damage to the brain or connecting spinal cord, with or without penetrating the skull. It relates more specifically to the actual mechanical damage that occurs at the type of trauma, such as shearing, tearing and stretching of axons, neurons and blood vessels. Usually, the initial trauma can result in expanding hematoma, subarachnoid hemorrhage, cerebral edema, raised intracranial pressure, and cerebral hypoxia, which can, in turn, lead to severe secondary events due to low cerebral blood flow.

In some further specific embodiments, the methods and kits of the invention may be applicable for treating and repairing nerve injury in a subject suffering from a spinal cord injury. "A spinal cord injury (SCI)" as used herein is damage to any part of the spinal cord or nerves at the end of the spinal canal. It often causes permanent changes in strength, sensation and other body functions below the site of the injury. The spinal cord injury may be a complete severing of the spinal cord, a partial severing of the spinal cord, or a crushing or compression injury of the spinal cord. Spinal cord injury SCI proceeds over minutes, hours, days and even months after the initial traumatic insult and can lead to significant expansion of the original damage. These secondary events are a consequence of delayed biochemical, metabolic and cellular changes, which are initiated by the primary injury, and includes inflammation, free radical induced cell death and glutamate excitotoxicity.

A typical nerve repair using the method of the invention is one in which the edges are ends of a cut peripheral nerve fascicle that are to be joined together or an end of a nerve fascicle and the fascicle of substitute nerve graft material. This latter situation is particularly applicable where nerve repair is required but a section of the nerve under repair has been severely damaged or is unavailable, so that the available ends of the fascicle are too remote from each other to be directly joined.

It should be appreciated that in some embodiments, the invention provides implants prepared by the methods and kits of the invention and adapted for specific nerve tissue. Thus, in yet more specific embodiments the invention further provides and encompasses nerve guidance conduit. In more specific embodiments, these conduit/s are prepared by the methods of the invention. More specifically, a nerve guidance conduit (also referred to as an artificial nerve conduit or artificial nerve graft, as opposed to an autograft) is an artificial means of guiding axonal regrowth to facilitate nerve regeneration and is one of several clinical treatments for nerve injuries. The creation of artificial conduits is also known as entubulation because the nerve ends and intervening gap are enclosed within a tube composed of the biomaterial of the invention. The conduits of the invention facilitate neurotropic and neurotrophic communication between the proximal and distal ends of the nerve gap, block external inhibitory factors, and provide a physical guidance for axonal regrowth. The nerve guidance conduit of the invention therefore combines physical, chemical, and biological cues under conditions that will foster tissue formation.

The invention thus provides therapeutic methods, specifically, methods for treating injured subjects.

"Treatment," "treat,", "treating," or "repair", "repairing" as used herein covers any treatment of tissue or organ injury of a mammal, particularly a human, and includes: (a) preventing tissue or organ injury from occurring in a subject which may be predisposed to the tissue or organ injury; (b) inhibiting tissue or organ injury, i.e., arresting its development; (c) relieving and or ameliorating the tissue or organ injury, i.e., causing regression of the tissue or organ injury; or (d) curing the tissue or organ injury, i.e., stopping its development or progression. The population of subjects treated by the methods of the invention includes subjects suffering from tissue or organ injury, as well as subjects at risk for development of the tissue or organ injury. It should be appreciated that the methods and kits described by the invention may be applicable for treating and/or ameliorating any of the disorders disclosed herein or any condition associated therewith. It is understood that the interchangeably used terms "associated", "linked" and "related", when referring to pathologies herein, mean diseases, disorders, conditions, or any pathologies which at least one of: share causalities, co-exist at a higher than coincidental frequency, or where at least one disease, disorder condition or pathology causes the second disease, disorder, condition or pathology. More specifically, as used herein, "disease", "disorder", "condition", "pathology" and the like, as they relate to a subject's health, are used interchangeably and have meanings ascribed to each and all of such terms.

The present invention relates to the treatment of subjects or patients, in need thereof. By "patient" or "subject in need"

it is meant any organism who may be affected by the above-mentioned conditions, and to whom the therapeutic methods and kits herein described is desired, including humans, domestic and non-domestic mammals such as canine and feline subjects, bovine, simian, equine and murine subjects, rodents, domestic birds, aquaculture, fish and exotic aquarium fish. It should be appreciated that the subject may be also any reptile or zoo animal. More specifically, the methods of the invention are intended for mammals By "mammalian subject" is meant any mammal for which the proposed therapy is desired, including human, livestock, equine, canine, and feline subjects, most specifically humans It should be noted that the biomaterial of the invention is intended for medical use. Therefore, in some embodiments, the biomaterial of the invention may be formulated in a pharmaceutical composition.

As used herein, the term "pharmaceutical composition" refers to a preparation of at least at least one biomaterial solution comprising said cell/s, or mixture of cells and magnetic particles described herein with other chemical components such as at least one of pharmaceutically acceptable carrier/s, excipient/s, auxiliaries, and/or diluent/s. The purpose of a pharmaceutical composition is to facilitate administration of a compound to a subject.

The term "pharmaceutically acceptable carrier" includes any and all solvents, dispersion media, coatings, antibacterial and antifungal agents and the like and refers to a carrier or a diluent that does not cause significant irritation to an organism and does not abrogate the biological activity and properties of the administered antagonist. An adjuvant is included under this term. Herein, the term "excipient" refers to an inert substance added to a pharmaceutical composition to further facilitate administration of an active ingredient.

Examples, without limitation, of excipients include calcium carbonate, calcium phosphate, various sugars and types of starch, cellulose derivatives, gelatin, vegetable oils, and polyethylene glycols.

Pharmaceutical compositions according to the invention may be manufactured by processes well known in the art, using one or more pharmaceutically acceptable carriers, e.g., by means of conventional mixing, dissolving, granulating, emulsifying, encapsulating, entrapping, or lyophilizing processes. Proper formulation is dependent upon the route of administration chosen.

It should be further noted that the invention therefore encompasses pharmaceutical compositions comprising the biomaterial of the invention that contains, at least one type of cells and at least one type of magnetic particles. In some further embodiments, the composition of the invention may further comprise at least one of pharmaceutically acceptable carrier/s, excipient/s, auxiliaries, and/or diluent/s.

It should be noted that the biomaterial solution used by the methods and kits of the invention may be injected, applied, pored, sprayed and inserted in the injured site. In some specific embodiments, the biomaterial solution used by the invention (that comprise the appropriate cells and magnetic beads) may be injected into the injured site.

In some specific embodiments, the administration of the biomaterial solution of the invention for the treatment or repair of tissue or organ injury in a subject, is by means of injection (with a syringe and a needle), surgery, catheterization (through catheters or shunts) or any other means suitable for modulating tissue repair. The biomaterial solution flows as liquid but still maintains sufficient consistency until injection into the desired location in the body, where it forms a solid aligned biomaterial, by applying magnetic field.

Since the methods of the invention involve the provision of the biomaterial solution of the invention into the injury site (in situ), in liquid form, and since several conditions may affect its liquid state, in some embodiments, the container or the administration means used by the methods of the invention may provide control of the temperature and other conditions of the biomaterial kept therein. Thus, in some specific embodiments, when the biomaterial solution of the invention is to be administered into the injury, for example by injection, to keep the biomaterial in the appropriate liquid state, any container, catheter, or syringe having a temperature control, may be used. Temperature can be controlled by setting external temperature to the potential syringe, container or catheter that hold the biomaterial. Devices for controlling the syringe temperature while injecting are commercially available and include for example, Syringe Heater (SW-10/6) (Harvard Apparatus), that may be used by the methods of the invention in some embodiments thereof.

Routes of administration of the biomaterial solution of the invention thereof include, but are not limited to, intramuscular, subcutaneous, intranasal, intracerebral, intraventricular, intracerebroventricular, intrathecal, intracisternal, intraspinal and/or peri-spinal routes of administration by delivery via intracranial or intravertebral needles and/or catheters with or without pump devices.

Administration of the biomaterial solution of the present invention for treatment of muscle injury to a subject in need thereof can be effected via injection directly into the injured muscle tissue.

In some embodiments, for neuronal application specific procedures may be used in the present invention for applying the biomaterial of the invention at the injured neuronal tissue. For example, Stereotactic surgery or stereotaxy is a minimally invasive form of surgical intervention which makes use of a three-dimensional coordinate system to locate small targets inside the body and to perform on them some action such as ablation, biopsy, lesion, injection, stimulation, implantation, radiosurgery (SRS), traditionally and limited to brain surgery. In one embodiment, the biomaterial solution of the invention is administered by Stereotactic surgery or stereotaxy.

Still further, Endoscopic endonasal surgery is a minimally invasive technique used mainly in neurosurgery. A neurosurgeon, using an endoscope that is entered through the nose, fixes or removes brain defects in the anterior skull base. Normally an otolaryngologist performs the initial stage of surgery through the nasal cavity and sphenoid bone; a neurosurgeon performs the rest of the surgery involving drilling into any cavities containing a neural organ such as the pituitary gland. In one embodiment, the biomaterial solution of the invention is administered by Endoscopic endonasal surgery.

It should be noted that for topical injuries, the methods of the invention may apply the biomaterial solution by injection, by topical application, or transdermal application for example, by dressing using further non-absorbable material for holding the liquid biomaterial of the invention. As used herein, the term "transdermal" refers to delivery, administration or application of a biomaterial by means of direct contact with tissue, such as skin or mucosa.

In some specific embodiments, the administration of the invention for the treatment of skin disorders, is by topical dressing. The term "dressing" means a covering for a wound or surgical site, typically composed of a film, cloth, fabric, synthetic membrane, gauze, or the like. It is usually a polymer-containing matrix covering an area of the skin. The dressing may or may not be in intimate contact with the skin. It can be, for example, a cloth or gauze, or it can be a biomaterial polymer solution painted or sprayed on the skin, the polymer solidifying on the skin when the solvent dries off and/or when the polymer crosslinks Dressings also include gels, films, typically cross-linked hydrogels, which are intended principally to cover and protect wounds, surgical sites, and the like.

In a further embodiments of the invention, a prosthetic patch, such as a prosthetic repair fabric, may be used to help holding an keeping the liquid biomaterial of the invention in the injury site. The prosthetic material may define the repair area and contain or hold the hydrogel composition to the repair area as it is implanted and as it sets. Moreover, the prosthetic patch may provide a scaffold to promote additional tissue adhesion or ingrowth. Additionally, the prosthetic material may provide a delivery system for pharmaceuticals or other repair materials embedded in the interstitial spaces of the scaffold structure of the material or released when the prosthetic material biodegrades. The prosthetic patch may not only contain the biomaterial of the invention, but also may define the repair site larger than the mere recess defined by the edges of the defect in the underlying tissue, particularly if the defect has irregular edges or is defined over a large surface area of the tissue to be repaired. The repair material, such as the biomaterial of the invention discussed above, may then promote tissue ingrowth not only to repair the defect, but also to regain or build volume of the defective tissue. Moreover, the biomaterial of the invention may also surround the defect as well as the adjacent healthy tissue with the biomaterial of the invention to enhance the repair and promote cell proliferation and extracellular matrix production. Surgical materials which are suitable for repair composition reinforcement, containment, and tissue ingrowth may be utilized including collagen mesh or sponge, gel, foam, polyester or DACRON mesh available from E.I. DuPont de Nemours and Co., GORETEX available from W.L. Gore and Associates, Inc., polymers, poly L-lactic acid sheeting and poly L-lactide/glycolide, polyglactin (VICRYL) and polyglycolic acid (DEXON), also may be suitable. It is also contemplated that the patch may be formed from monofilament or multifilament yarns and that woven, knitted, interlaced, molded and other suitable methods of forming prosthetic materials may be employed.

It is to be appreciated that any suitable materials which are biocompatible may be used as a temporary mold or dressing material as would be apparent to one of skill in the art. Preferably the material is biodegradable and has a life of approximately 6 months. Preferably, the material of the patch allows tissue ingrowth either as the material itself biodegrades over time or provides spaces or interstices suitable for tissue ingrowth. Alternatively, it is to be appreciated that the material of the patch or any portion of the patch may resist adhesion or tissue ingrowth, as would be apparent to one of skill in the art. The patch can be a blend, mixture, or a hydrogel of any of the materials to form a temporary or permanent patch to contain or reinforce or repair tissue in the defect and/or promote tissue adhesion formation. The material of the patch is relatively flat and sufficiently pliable to allow a surgeon to manipulate the shape of the implanted patch to conform to the anatomical site of interest and to be sutured or stapled thereto. The shape and size of the patch may vary according to the surgical application as would be apparent to one of skill in the art. In this regard, it is contemplated that the material of the patch may be pre-shaped or shaped by the surgeon during the surgical procedure.

In one embodiment, the patch may be constructed as a film or mesh with small or microscopic interstices sufficient to promote tissue ingrowth, while still retaining the ability to contain the injected hydrogel biomaterial.

The attachment of the patch to the surrounding tissue need not be a waterproof seal. Rather, the surface tension of the hydrogel material may be sufficient to contain the hydrogel in the contained implant area and will not seep out of any openings between the edge of the patch and the adjacent tissue. Moreover, to sufficiently contain a hydrogel, any interstices or holes in the mesh should be small enough to retain the implanted hydrogel material before it sufficiently sets.

It should be understood that the methods of the invention use different elements or components that may be provided according to some embodiments, in a kit. Optionally, such elements may be provided in one or more containers. The kit of the invention provides flexibility in the provision of all elements required in the methods of the invention, specifically as discussed above.

Thus, in another aspect, the invention provides a kit or system comprising: (a) at least one liquid biomaterial or biomaterial solution comprising cell/s, or mixture of cells and magnetic particles or any conjugate, mixture, embedment and encasement thereof or any composition or matrix comprising the same; and (b) at least one or at least two magnetic sources placed at a distance providing a magnetic field having a strength of between about 5 G to about 5000 G.

In further embodiments, the magnetic sources suitable for the kit may be portable magnetic sources comprised within a device and held by or connected to adjustable holders.

In some other embodiments, the kit of the invention may optionally further comprises an adjustable biodegradable mold.

In certain embodiments, the liquid biomaterial of the kit of the invention may be liquid hydrogel.

In yet some further embodiments, the hydrogel of the kit of the invention may be a collagen solution. As discussed above in connection with other aspects of the invention, any collagen solution may be used in the kits of the invention. In some specific embodiments, the collagen used by the kit of the invention may be collagen type I.

In some embodiments, the concentration of the collagen solution of the kit of the invention ranges between about 0.1 to about 10 mg/ml. In more specific embodiments, a collagen solution of 1.4 mg/ml may be used in the kits of the invention. In yet some more specific embodiments, a collagen solution of 3 mg/ml may be used in the kits of the invention.

In certain embodiments, the magnetic particles suitable for the kit of the invention may be composed of any one of a magnetite core, a maghemite core, Ferrite core or iron oxide core. In some embodiments, the magnetic particles suitable for the kit of the invention may be uncoated or coated magnetic particles.

In certain embodiments, the magnetic particles suitable for the kit of the invention may be uncoated magnetic particles.

In certain embodiments, the magnetic particles suitable for the kit of the invention may be coated magnetic particles. In certain embodiments, the magnetic particles suitable for the kit of the invention may be coated with oleic acid-sodium salt.

In some embodiments, the magnetic particles suitable for the kit of the invention may be coated particles, specifically, coated with anyone of e.g., dextran, polyvinyl alcohol (PVA), polyethylenimine (PEI), silica, dextransulfate, starch, citric acid salt, PEG/Amine, Chitosan, Streptavidin, or Oleic acid sodium salt. In yet some specific embodiments, any magnetic particles of any size used by the kits of the invention, specifically, in case of micro-particles, may be coated particles, provided that said coating is not a Streptavidin coating.

In yet another embodiment, the magnetic beads of the kit of the invention may be at least one of conjugated, attached, linked, mixed with, encapsulated within, or encapsulating at least one of cell growth, cell guiding and cell selective agent. In yet another embodiment, the cell growth agent suitable for the kit of the invention may be at least one growth factor. In some embodiments, the magnetic beads of the kit of the invention may be conjugated, attached, linked, mixed with, encapsulated within, or encapsulating at least one cell growth factor. In some specific embodiments, such growth factor may be Nerve Growth Factor (NGF).

In another embodiment, the diameter of the magnetic particles suitable for the kit of the invention may range between about 0.1 nm to 100 μm.

In some embodiments, the diameter of the magnetic particles suitable for the kit of the invention ranges between about 1 nm to 1 μm. In more specific embodiments, the diameter of the magnetic particles may be 10 nm. In yet some further embodiments, the diameter of the magnetic particles may be 20 nm. In still further embodiments, the diameter of the magnetic particles may be 50 nm. In yet some further embodiments, the diameter of the magnetic particles may be 100 nm.

In further embodiments, the magnetic field of the kit of the invention may be a static magnetic field provided by at least two magnetic sources. In more specific embodiments, the magnets may be electromagnets or permanent magnets. It should be noted that any of the magnetic sources discussed above may be comprised within the kit of the invention. In yet some further embodiments, the magnetic sources may be provided in an array.

In some specific embodiments, the biomaterial of the kits of the invention may be collagen type I. In yet some further embodiments, the collagen type I is collagen solution of 1.4 or of 3 mg/ml. In yet some further embodiments, the solution of 1.4 or of 3 mg/ml suitable for the kit of the invention comprises cells or cell mixtures and magnetic beads having a diameter of about 10 nm. In yet some further embodiments, the magnetic beads used are beads having a diameter of about 20 nm or of 100 nm.

In certain embodiments, the cells used for the kit of the invention may be any mammalian cell. In yet more specific embodiments, such cells may be at least one of neuronal cells or skin cells.

In other embodiments, the kit of the invention may be for use in guiding growth of a cell, a mixture of cells or cell component/s in a subject in need thereof.

It should be noted that the kit of the invention may comprise any further compound, cross linker or growth factor, as specifically discussed above. In yet some further embodiments, the kits of the invention may further comprise any reagent or any instrument for providing suitable conditions for the provision of the biomaterial of the invention in the appropriate injury site, for growing cells (e.g., tissue culture media, serum, antibiotics and the like), and for the establishment of the prostatic implant created by the methods and kits of the invention. In yet some further embodiments, the kits of the invention may further comprise any apparatus, device or means for controlling conditions that affect the liquid state of the biomaterial of the invention. Such parameters may include, temperature, pH, and the use of cross linking agents. For example, the kit of the invention may comprise any container, catheter or syringe having a temperature control, as discussed above in connection with the methods of the invention.

Another aspect of the invention is directed to a temporary mold device for surgically implanting a hydrogel to repair a tissue defect. Still further, the invention provides a system containing a device that comprise at least one or at least two adjustable holders suitable for holding the magnetic sources in a distance providing a magnetic field having a strength of between about 5 G to about 5000 G.

In yet a further aspect, the invention relates to at least one liquid biomaterial or biomaterial solution comprising said cell/s, or mixture of cells and magnetic particles or any conjugate, mixture, embedment and encasement thereof or any composition or matrix comprising the same, and at least one or at least two magnetic sources placed at a distance providing a magnetic field having a strength of between about 5 G to about 5000 G, for use in a method for in situ treating or repairing tissue or organ injury in a subject.

In yet some further embodiments, the liquid biomaterial or biomaterial solution of the invention may be particularly suitable for use in a method for guiding cell growth in a subject in need thereof.

In yet a further aspect, the invention relates to at least one liquid biomaterial or biomaterial solution comprising said cell/s, or mixture of cells and at least one type of magnetic particles or any conjugate, mixture, embedment and encasement thereof or any composition or matrix comprising the same, and at least one or at least two magnetic sources placed at a distance providing a magnetic field having a strength of between about 5 G to about 5000 G, for use in a method for wound healing in a subject.

In further embodiments, the liquid biomaterial and at least two magnetic sources for use according to the invention, wherein the magnetic sources may be portable magnetic sources comprised within a device and held by or connected to adjustable holders.

In certain embodiments, the liquid biomaterial for use according to the invention may be provided and placed in the injured tissue within an adjustable biodegradable mold.

In yet another embodiment, the liquid biomaterial of the invention may be liquid hydrogel.

In another embodiment, the hydrogel may be a collagen solution.

In some specific embodiments, the collagen used in the invention is collagen type I.

In some embodiments, the concentration of the collagen solution may range between about 0.1 to about 10 mg/ml. In more specific embodiments, a collagen solution of 1.4 mg/ml is used in the invention. In yet some more specific embodiments, a collagen solution of 3 mg/ml is used in the invention.

In further embodiments, the magnetic particles for use according to the invention may be composed of any one of a magnetite core, a maghemite core, Ferrite core or iron oxide core. In other embodiments, the magnetic particles for use according to the invention may be uncoated or coated magnetic particles. In more specific embodiments, the magnetic particles for use according to the invention may be uncoated magnetic particles. In more specific embodiments, the magnetic particles for use according to the invention may be coated magnetic particles.

In more specific embodiments, the magnetic particles for use according to the invention may be coated with oleic acid-sodium salt.

In some embodiments, the magnetic particles may be coated particles, specifically, coated with any one of dextran, polyvinyl alcohol (PVA), polyethylenimine (PEI), silica, dextransulfate, starch, citric acid salt, PEG/Amine, Chitosan, Streptavidin, or Oleic acid sodium salt. In yet some specific embodiments, any magnetic particles of any size used by the invention, specifically, in case of micro-particles, may be coated particles, provided that said coating is not a Streptavidin coating.

In further embodiments, the magnetic beads for use according to the invention may be at least one of conjugated, attached, linked, mixed with, encapsulated within, or encapsulating at least one of cell growth, cell guiding and cell selective agent. In another embodiment, the cell growth agent is at least one growth factor.

In some embodiments, the magnetic beads for use according to the invention may be conjugated, attached, linked, mixed with, encapsulated within, or encapsulating at least one cell growth factor. In some specific embodiments, such growth factor may be Nerve Growth Factor (NGF).

In further embodiments, the diameter of the magnetic particles may range between about 0.1 nm to 100 μm.

In some embodiments, the diameter of the magnetic particles may range between about 1 nm to 1 μm. In more specific embodiments, the diameter of the magnetic particles may be 10 nm. In yet some further embodiments, the diameter of the magnetic particles may be 20 nm. In still further embodiments, the diameter of the magnetic particles may be 50 nm. In yet some further embodiments, the diameter of the magnetic particles may be 100 nm.

In further embodiments, the magnetic field of the invention may be a static magnetic field provided by at least two magnetic sources. In more specific embodiments, the magnets may be electromagnets or permanent magnets.

In some specific embodiments, the biomaterial of the invention may be collagen type I. In yet some further embodiments, the collagen type I is collagen solution of 1.4 or of 3 mg/ml. In yet some further embodiments, the solution of 1.4 or of 3 mg/ml comprises cells or cell mixtures and magnetic beads having a diameter of about 10 nm. In yet some further embodiments, the magnetic beads used are beads having a diameter of about 20 nm (core dry diameter) of 100 nm (hydrodynamic diameter).

In yet another embodiment, the cells for use according to the invention may be at least one of neuronal cells or skin cells.

In yet another embodiment, the biomaterial of the invention may be for use in guiding growth of a cell, a mixture of cells or cell component/s in a subject in need thereof.

Other purposes and advantages of the invention will become apparent as the description proceeds. While in the foregoing description describes in detail only a few specific embodiments of the invention, it will be understood by those skilled in the art that the invention is not limited thereto and that other variations in form and details may be possible without departing from the scope and spirit of the invention herein disclosed or exceeding the scope of the claims.

The present invention as defined by the claims, the contents of which are to be read as included within the disclosure of the specification, and will now be described by way of example with reference to the accompanying Figures.

All scientific and technical terms used herein have meanings commonly used in the art unless otherwise specified. The definitions provided herein are to facilitate understanding of certain terms used frequently herein and are not meant to limit the scope of the present disclosure.

The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range. As used herein the term "about" refers to ±10%.

The terms "comprises", "comprising", "includes", "including", "having" and their conjugates mean "including but not limited to". This term encompasses the terms "consisting of" and "consisting essentially of". The phrase "consisting essentially of" means that the composition or method may include additional ingredients and/or steps, but only if the additional ingredients and/or steps do not materially alter the basic and novel characteristics of the claimed composition or method. Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

It should be noted that various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Various embodiments and aspects of the present invention as delineated herein above and as claimed in the claims section below find experimental support in the following examples.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Reference is now made to the following examples, which together with the above descriptions illustrate the invention in a non-limiting fashion.

Experimental Procedures

Collagen Gel Preparation

The following collagen mixture was prepared under sterile conditions and held on ice to prevent initiation of gelation. In a sterile 1.5 mL reaction tube Collagen (type-I rat tail extract, in 0.02M acetic acid, BD-Biosciences, Bedford, Mass., USA initial concentration of 3.35-4 mg/mL) was diluted by the addition of 10×L-15 (Sigma Aldrich Co, Stienhiem, Germany) (filter sterilized) and 7.5% sodium carbonate (filter sterilized). Physiological pH was indicated by phenol red within the mixture. Final collagen concentration was brought to 3 mg/mL, or 1.4 mg/mL and volume of 10×L-15 was brought to ×1 concentration and sodium carbonate were adjusted with accordance to collagen batch (2.5%-3% of final volume). Gel mixture was then plated upon a 13 mm glass coverslip within a 35 mm petri dish (UV sterilized). The gel was then allowed to solidify and stabilize within a within 25° C. incubator for 40 minutes, as specified in the Examples, following which the gel was immersed in 2-3 mL medium.

Magnetic Actuation Setup

Collagen gel samples containing cells and magnetic particles were placed on a portable stage connected to two transverse movable plastic holders, each holder containing a magnet (NdFeB, Grade N50, coated NiCuNi, size D18*18 [mm]). (FIG. 1A) control over magnetic field strength was achieved by adjusting magnet to stage distance (FIG. 1B).

Magnetic Actuation and Magnetic Particle Organization

To 100 μL of freshly prepared collagen mixture, 0.05 mg magnetic particles were added. Collagen suspensions then were placed on a portable stage connected to two transverse movable plastic holders, each holder containing a magnet (NdFeB, Grade N50, coated NiCuNi, size D18*18 [mm]). Control of magnetic field strength was achieved by adjusting holder to stage distance (FIG. 1), and measured at 255 G. Effective magnetic field strength was measured at the center of the stage via A digital Gauss-meter (Scientific Equipment Roorkee, DGM-204). The following different magnetic particles of varying size and composition (chemicell GmbH, Berlin, Germany) were examined: The sizes listed are hydrodynamic diameter as supplied from the manufacturer.

1. SiMAG-Silanol 1 μm (product #1101-1, Maghemite core, silica matrix).
2. SiMAG-Silanol 3 μm (product #1101-1, Maghemite core, silica matrix).
3. nano-screenMAG/R-UC/C 100 nm (product #, 4430-1, Magnetite core).
4. fluidMAG-UC/C 100 nm (product #4130-1, Maghemite core).
5. nano-screenMAG/R-DXS 150 nm (product #4405-1, Magnetite core, dextran coating).
6. MAG/R-D 100 nm (product #4101-1, Magnetite core, starch coating).
7. fluidMag-CT (product #4122-1, Magnetite core, Citric acid-sodium salt coating).
8. PEG/Amine—fluidMAG-PEG/Amine (product #4131, magnetite core, 100 nm hydrodynamic diameter).
9. Chitosan—fluidMAG-Chitosan (product #4118, magnetite core, 100 nm hydrodynamic diameter).
10. Dextran Sulfate—fluidMAG/G-DXS (product #4405, magnetite core, 100 nm hydrodynamic diameter).
11. Uncoated cationic—fluidMAG-UC/C (product #4130, magnetite core, 50 nm hydrodynamic diameter).
12. Streptavidin—fluidMAG-Streptavidin (product #4205, magnetite core, 200 nm hydrodynamic diameter).
13. Oleic acid sodium salt—fluidMAG-OS (product #4113, magnetite core, 100 nm hydrodynamic diameter).

Magnetic Measurements

An amount of 0.1 mg of each sample was dried thoroughly at room temp for several days, and Magnetic measurements were performed at room temperature, by a Quantum Design MPMS-5XL SQUID Magnetometer. Normalized data is shown.

Magnetic Iron-Oxide Synthesis

Magnetic particles were synthesized by coprecipitation technique (Robert N. Muller, 2008). ferrous and ferric salts were dissolved in a 2:1 molar ratio in a non-oxidizing environment (4.7 g FeCl3 and 1.73 g FeCl2 in 100 ml degased-argonized DDW). 8.4 ml Ammonium hydroxide (28-30%) solution was added to induce basic pH environment, and the solution was mixed via magnetic stirring. Argon was continua sly bubbled through the solution. The magnetic particles obtained were then washed in DDW via repeated centrifugations. The particles were then dissolved in DMSO and a diluted sample in DDW was analyzed by TEM imaging.

Conjugation to NGF

Conjugation of NGF was obtained through EDC/NHS coupling of MNP with terminal COOH groups and free amines on NGF.

First, MNPs with terminal amines were modified through succinic anhydride to form carboxylate containing MNPs (Greg T. et al. Academic Press, 589-740 (2013). 250 μL of PEG/Amine-fluidMAG-PEG/Amine (product #4131, magnetite core, 100 nm hydrodynamic diameter) were separated via centrifugation from storage buffer and resuspended in sodium bicarbonate (1M, pH 8), 25 mg of succinic anhydride (Sigma Aldrich) were added and the vial was shaken for 1 h at room temperature, followed by 3 sequential washes (1×1M NaCl, and 2×DDW). To activate the reaction MNPs were suspended in 250 μL MES buffer (Chem-Impax, pH 4.8), and 50 μL of EDC/Solfo-NHS solution was added (Sigma Aldrich, 400 mM and 200 mM respectively). Following shaking for 1 hour, the MNP mixture was centrifuged and 200 μL were replaced with PBS. Simultaneously, 20 μg Murine β-NGF (Peprotech, Israel) were solubilized in 100 μL DDW, and added to MNP activated solution. The mixture was shaken overnight at 4° C., followed by thorough washes in DDW. Finally the MNP solution was suspended in 250 μL 0.1% BSA in DDW. The conjugation of NGF was monitored via ELISA assay (Chemicon Int.)

High Resolution Scanning Electron Microscopy

Collagen gels were fixed using 2.5% paraformaldehyde/2.5% gluteraldehyde in 0.1M sodium cacodylate buffer for 1 h at room temperature. After fixation, gels were repeatedly rinsed with PBS (without $Ca^{+2}$ or $Mg^{+2}$, pH 7.4) and then treated with guanidine-HCl/tannic acid (4:5) solution (2%) for 1 h at room temperature. Cultures were repeatedly rinsed with PBS and then dehydrated in graded series of 50%, 70%, 80%, 90%, and 100% ethanol/water (v/v) for 10 minutes each. The residual ethanol was then removed using a series of 50%, 75%, and 100% (×3) Freon solutions in ethanol, for 10 minutes each. Finally, the samples were left for a few seconds to dry under air. In order to view the cells inside the scaffolds, the samples were broken into pieces using fine tips. The dried samples were mounted on aluminum stubs, sputter coated with carbon, and viewed with the SEM (Model FEI Quanta250 FEG, OR).

Confocal Reflectance Microscopy (CRM)

Collagen samples were prepared as described above, containing 0.05 mg MPs (MAG/R-UC/C Magnetite core 100 nm, chemicell GmbH, Berlin, Germany) and solidified under the influence of a magnetic field set to 255 G. Control samples, without MPs but sulidified under the influence of 255 G were prepared as well. Polymerized 3D collagen gels were imaged using Leica TCS SP5 confocal microscope via a X63, 0.9 NA water immersion lens, or ×20 0.5 NA water immersion lens. Samples were illuminated with 488 nm Argon laser light and the Meta channel of the microscope was set to detect wavelengths between 474 and 494 nm to allow reflectance mode. Images were taken from random areas and planes from the center of the gel, to avoid edges of the gel.

Gel pore size measurements: Image J was used to measure the pore areas from CRM images (5 images minimum for each gel, 150 measurements minimum per sample). Gel pores are of an irregular polygonal shape, measured pore diameter presented is of the large perpendicular.

Magnetically Aligned Gel FFT Analysis

To measure fiber alignment we used two-dimensional (2D) fast Fourier transform (FFT) analysis of SEM and CRM images obtained. Images were cropped to adjust for fiber continuing windows only, as shown in FIG. 3C-D. Angular analysis of the FFT data was performed in accordance to a method described in Ayres et al, 2008. The CRM images of magnetically aligned gel images were analyzed and compared to control gels. All alignment data was normalized so that the sum of all angle bins is 1. For analysis, each gel sample a minimum of 10 CRM images were considered.

Live Imaging Microscopy

Collagen gels samples, with or without MNPs, were prepared on ice as described. 60 μl of each suspension was then pipetted on a glass bottomed petri dish, which was placed beforehand on the microscopy stage securely. The samples were observed using a Nikon TE2000E inverted microscope with a X40 air coupled lens (0.95 NA or 0.6 NA), focused above the glass plane. Images were acquired with a Retiga 2000R imager (QImaging, Surrey, British Columbia, Canada). The microscope and camera were controlled using Nikon NIS Elements software. Images were acquired prior to placing the collagen liquid to petri dish, to capture the gelation process completely. Images were acquired every 10 seconds for 20 minutes at least. Control samples were obtained of collagen gel 3 mg/mL without MNPs and with MNPs without magnetic field. Aligned gels were achieved by placing a collagen solution 3 mg/mL containing MNPs within an actuating magnetic field. No image processing was conducted.

Genipin Cross-Linked Gels:

For gels containing genipin, a stock solution of freshly made genipin in 10×PBS containing 1% DMSO (6 mg/mL) was used in place of a volume of 10×DMEM to obtain the desired genipin concentration (0.25 or 0.5 mM). Gels were then placed in a 37° C. for 30 minutes to induce gelation, following which gels were immersed in PBS.

Absorbance & Fluorescence Measurements of Genipin Cross-Linked Gels

Collagen solutions containing 0 mM, 0.25 mM or 0.5 mM genipin were prepared as described and plated in triplicates into 96 well plates (100 μL 1×PBS was pipetted on each gel following 30 minutes of gelation in a 37° C. incubator. Plates were measured immediately following gelation (t=0 h) and at regular time intervals. Measurements were taken using a synergy4 plate reader (BioTek, USA) at 595 & 630 nm (absorbance) or excitation 595 nm, emission 630 nm (fluorescence) at room temperature.

The fluorescence was corrected for the internal filter effect as described by Macaya et al. (Macaya, et al. Advanced Functional Materials 21.24, 4788-4797 (2011)) and Palmier, et al. (Palmier Mark O et al. Analytical biochemistry 371.1, 43-51 (2007)).

F corrected=F observed*10(Aex+Aem)/2 Where A ex and A em are the measured absorbance at the excitation and emission wavelengths respectively. Experiment was conducted (n=3) and a representative measurement is shown.

Leech Neuronal Culture

Neurons were isolated from the central nervous system of adult medicinal leeches *Hirudo medicinalis* as following: Leeches were anaesthetized in ice for 20 min before dissection. The Animal was then stretched longitudinally and pinned dorsal side down on a Sylgard ice-cooled surface. The dorsal skin was cut full length of the animal and access blood washed with leech ringer solution (115 mM Nacl2, 1.8 mM CaCl2, 4 mM KCl, 10 mM Tris maleate, pH 7.4). Nerve cord and ganglia were then exposed and dissected with fine scissor tips taking care not to cut nerve roots or connectives. Ganglia were pinned down on a Sylgard-184 petri dish using 0.002" tangsten cord, and immersed in Leibovitz-15 (L-15) complete medium (L-15 supplemented with 6 mg/ml glucose, 0.1 mg/ml gentamycin, 2 mM/ml glutamine and 2% fetal bovine serum). Next, ganglia were treated enzymatically with 2 mg/ml Collagenase/Dispase enzyme solution (Roche, Mannheim, Germany) within L-15 complete medium for 1 h at room temperature Finally, ganglia capsules were opened carefully using fine scissors to expose cells. Cells were collected by micropipite to a 1 mL test tube containing L-15 medium. Following 3 successive washes by spin-down (1,500 rpm), cells were suspended in 20-30 μL L-15 and immediately seeded within 3D collagen gel. Gels were allowed to solidify within 25° C. incubator for 40 minutes.

Leech Neuronal Magnetically Aligned Collagen Hydrogels Cultures

To 100 μL of freshly prepared of collagen suspension 5-10 μL of L-15 containing extracted leech neurons along with 2 μL (0.05 mg, # of particles 9×10^10) magnetic particles (MAG/R-UC/C Magnetite core 100 nm, chemicell GmbH, Berlin, Germany), following which the mixture was mixed carefully by pipettation, taking care not to introduce air bubbles. The mixture was then transferred and spread upon a 13 mm glass coverslip placed in a chamber within a magnetic field (both UV sterilized). The magnetic field at the gel sample location was measured as 255 G. The gel was then allowed to solidify and stabilize within a 25° C. humidified chamber for 40 minutes, during which the nanoparticles aligned to form lines in accordance to the magnetic field lines. Following the 40 minutes allowing the gel to solidify the gel was removed from the magnetic field and placed in a sterile petri dish. The gel was then immersed in 3-4 mL L-15 complete medium. Typically, cultures were kept in the dark at 25° C. in a humidified chamber, and L-15 complete medium was replaced daily. Neuronal growth was followed for 7 days.

Live/Dead Assay—Leech Neuron Viability Assay

Following 7 days in magnetically aligned cultures leech neurons were stained for Live/Dead (Live/Dead imaging kit R37601, Life Technologies) and examined with a fluorescent microscope. Neurons grown in gels absent of MPs or magnetic field solidification were examined as well. Live cells were examined at green fluorescence (ex/em 488 nm/515 nm) and dying cells at red fluorescence (ex/em 570 nm/602 nm). Total of 1600 cells were manually counted and death rate was quantified (total of four gels).

Electrophysiological Recording

Microelectrodes for intracellular recordings were made with borosilicate glass of 1 mm exterior diameter and 0.75 mm internal diameter pulled in a P97 puller (Sutter Instruments) to create a tip diameter of 0.7-0.9 μm. The microelectrodes had resistances of 18-23MΩ when filled with 3M potassium acetate. A standard single-electrode current-clamp intracellular recording technique was used to monitor spike activity in leech neuronal culture embedded in thin collagen films. Signals are amplified (Molecular devices multi clamp 700B) filtered and digitized by an analog-to-digital board Digidata 1400A (Axon Instruments). Date were stored on a PC using pClamp 10.3 software (Molecular devices).

Rheometry

Rheological analysis was performed on a rheometer TA instruments HR-3 using a 8 mm parallel plate geometry. Collagen gels were prepared as described and samples were placed on rheometer stage. Rheometer plate was then lowered and the stage was adjusted so gel sample was placed directly under the plate. A solvent trap was employed to reduce effects of dehydration. Settings were held at 25° C. and Frequency sweeps from 1 to 100 Rad/s were performed using a controlled stress of 0.5 Pa and 5% strain. Storage, loss and complex moduli were recorded and values found to be within the linear viscoelastic range of the system are presented. Three experiments in triplicates were recorded.

The magnitude of response at 10 rad/s was compared to literature.

Elastic Modulus was calculated as described in Healy, 2008.

$$E'=2G'(1+\nu)$$

Where G' is the storage modulus at 1 Hz as measured by the rheometer and ν is Poisson's ratio, assumed to be 0.5.

Degradation Assay

Collagen gels were fabricated as described (n=3) containing genipin (0, 0.25, and 0.5 mM) and allowed to gel at 37° C. for 30 minutes as well as control gels without genipin. Collagenase (0.1 U/mg Collogenase/Dispase 10269638001 sigma) at 0.5 mg/mL in 1×PBS, was added on top of the gel and the plates were placed on a shaker table in a 37° C. incubator at 150 rpm. After 18 h, the degradation medium was removed, the gels were dried thoroughly on Whitman filter paper, and weighed. The dry weights of the scaffolds were compared to the weights of identical gels exposed to 1×PBS buffer for the same amount of time; data are reported as % weight remaining Average of 4 individual experiments is shown.

In order to compare genipin cross linking on collagen gel degradation rate a standardized assay of degradation was developed. To note, Collagenase concentration (0.5 mg/mL) was chosen to provide an accelerated evaluation of genipin effect on gel robustness. The concentration is much greater than what would be found in in-vivo.

Turbidity

Rate of fibrillogenesis was measured using turbidity. The collagen solutions were prepared on ice as described above, and 100-1 L aliquots were pipetted into a cooled 96-well plate, in triplicates. The absorbance of the solution was measured at 405 nm every 30 seconds at temperatures of 25° C. in a synergy4 plate reader (BioTek, USA). For analysis normalized absorbance was calculated (as shown by FIG. 13B).

Immunocytochemistry

Medium was removed from collagen gel cultures and each culture well was rinsed 2-3 mL PBS, followed by fixation with 4% paraformaldehyde for 45 min at room temperature. The cultures were again washed with PBS and permeabilized with 0.5% Triton X-100 in PBS (PBT) for 10 min. Gels were then incubated in a blocking solution (containing 1% bovine serum albumin (BSA) and 1% normal donkey serum (NDS) in 0.25% PBT) for 1 h. Next, cultures were treated with 1:500 rabbit antibody to α-tubulin antibody (Santa Cruz Biotechnology, Inc., Santa Cruz, Calif.) in blocking solution overnight at 4° C. The cultures were then rinsed 3 times with PBS and incubated for 45 min at room temperature with 1:50 Cy3-conjugated AffiniPure Donkey Antirabbit secondary antibody in blocking solution (Jackson ImmunoResearch Laboratories, Inc., West Grove, Pa.). Confocal imaging was performed using Leica TCS SP5 to acquire fluorescent, collagen reflectance and bright field images.

PC12 Collagen Gel Culture

PC12 cells were grown in suspension in RPMI medium supplemented with 10% horse serum (HS), 5% fetal bovine serum (FBS), 1% L-glutamine, 1% penicillin-streptomycin and 0.2% amphotericin, in a humidified incubator at 37° C. containing 5% CO2. To obtain 3D collagen gel system appropriate for PC12 cells a collagen solution was prepared in a similar method as described for leech neuronal culture. Briefly, a collagen mixture containing collagen (type-I rat tail extract, in 0.02M acetic acid, BD-Biosciences, Bedford, Mass., USA), an appropriate amount of PC12 serum reduced medium (1% HS), and 7.5% sodium carbonate (filter sterilized) was prepared under sterile conditions on ice. Physiological pH was indicated by phenol red within the mixture and final collagen concentration was brought to 1.5 mg/mL, or 3 mg/mL. For the 3 mg/mL collagen gels 5000 PC12 cells were added to 100 μL of collagen mixture containing 0.05 mg) magnetic particles (MAG/R-UC/C Magnetite core 100 nm, chemicell GmbH, Berlin, Germany), and for 1.4 mg/mL magnetic particles (0.05 mg of SiMAG-Silanol Maghemite core and silica matrix 1 μm, chemicell GmbH, Berlin, Germany), Following which the mixture was mixed carefully by pipettation, taking care not to introduce air bubbles. and plated upon a 13 mm glass coverslip placed in the magnetic actuation setup at 255 G. The gel was then allowed to solidify and stabilize within a 37° C. humidified incubator for 1 hour, following which the gel was removed from the magnetic actuation setup and placed in a petri dish (UV sterilized). The gel was then immersed in 2 mL serum reduced media (1% HS). To induce PC12 differentiation, 24 h after seeding Murine β-NGF (Peprotech, Israel) was added to the medium at a final concentration 50 ng/mL. Medium containing Murine β-NGF was replaced every 2 days in 2 sequential treatments.

Morphometric Analysis

The morphometric parameters of neurons grown were measured within magnetically aligned gels. Neurons out of 5-6 ganglia were plated per gel (as described in the Cell Culture subsection). Confocal 3D stacks of gels were submitted to further analysis. To measure process length in 3D collagen gels Simple neurite tracer and ImageJ plugins (US National Institutes of Health, Bethesda, Md.) were both used, which enables semiautomatic tracing of neurites and 3D length measurements. Neurites were traced individually, as shown in FIG. 14C. Morphometric parameters measured: average neurite number per cell, average neurite length per cell and neurites total branching tree length (as summed length of neurites for each cell). Measurements are summarized in bar charts. Error bars represent standard errors, and P-value is shown as calculated by t-test. Leech neuronal culture in magnetically aligned gels measurements were taken for N=25 cells, control of N=18 cells. PC12 measurements of 3 mg/mL collagen gel containing 100 nm MNPs, and 1.4 mg/mL collagen gel containing 1 μm N=23, and N=34 respectively.

To analyze 3D growth and cell orientation within magnetically aligned gels, data from confocal z-stacks was extracted manually and analyzed using a MATLAB script. A representation of the spatial arrangement of each cell was plotted in the form of a cuboid (FIG. 15C, 15D, circles represent end points of neurites, or soma.

Measurement of cuboids longest axis divided by the second longest axis (x'/y') gave cellular elongation. Measurements of the cuboid's longest axis length gave growth direction, designated 2D orientation. Magnetic string orientation (2D) was measured via the same MATLAB script, using vectors extracted from collagen gel images. Cell orientation was compared to magnetic string orientation and the angle difference was designated as AO and data was binned to ±15° or ±30° and statistically analyzed. First one-sample Kolmogorov-Smirnov test was evaluated to calculate the probability of distribution of AO. Null Hypothesis of normal and uniform distributions were rejected for Leech neuronal culture in magnetically aligned gel. Secondly, Chi-square test for the binned results±30° was performed, with expected equal distribution of AO.

SH-SY5Y and 3T3 Collagen Gel Culture

SH-SY5Y and 3T3 cells were grown in DMEM medium supplemented with 10% fetal bovine serum (FBS), 1% L-glutamine, 1% penicillin-streptomycin and 0.2% amphotericin, in a humidified incubator at 37 □C containing 5% CO2. Collagen mixture was prepared on ice as described, containing 0.05 mg fluidMAG-OS (product #4113), containing 0 mM, 0.25 mM or 0.5 mM Genipin. 10,000 cells were added in appropriate medium (volume of 1-5 uL) to 100 uL collagen gel mixture, to final collagen concentration of 3 mg/mL. The mixture was mixed carefully by pipettation, taking care not to introduce air bubbles. Gel mixture was then plated upon a 13 mm glass coverslip placed in the magnetic actuation setup at 950 G. The gel was then allowed to solidify and stabilize within a 37° C. humidified incubator for 30 minutes, following which the gel was removed from the magnetic actuation setup and placed in a petri dish, or 24-well plate (UV sterilized). The gel was then immersed in 2 mL medium.

Cell Viability

SH-SY5Y or 3T3 cells were seeded in collagen gels as described, containing magnetic particles 0.05 mg fluidMAG-OS (product #4113) with and without 0.25 mM or 0.5 mM genipin. Control gels without magnetic particles or genipin were prepared as well. Gel mixtures were then plated in triplicates in a 96 well plate. Gels were allowed to gel in a 37° C. incubator for 30 minutes, following which the gel was immersed in 100 μL medium. Medium was replaced at 72 h, to reduce the amount of genipin extracted from the gel induced by medium replacement. Following a week of incubation PrestoBlue cell viability reagent (Molecular probes, A-13261) was added to gel culture medium at final concentration of 1×, and incubated for 2 hours in a 37° C. incubator, to allow diffusion inside the gel. 100 μL of the medium was removed and transferred to a black 96 well plate (Greiner 655090). Fluorescence measurements were taken using a synergy4 plate reader (BioTek, USA) at excitation 540 nm emission 590 nm. Background fluorescence was corrected by subtracting the average fluorescent in control wells containing cell media without cells incubated with PrestoBlue reagent. Results were normalized to control collagen gel cultures without particles or genipin. To explore the influence of the magnetic field on cell viability, an experiment was conducted using 950 G on gels (as described in gel culture section) showing no influence of magnetic field on cell viability, as reported previously (Antman-Passig 2016) Results are shown on 3 individual experiments.

DRG Explant

All animal studies were conducted in accordance with animal care and protection regulations as approved by the Bar-Ilan university ethics committee (24042015 license number). Adult C57b1 mice, 6-9 week old, were euthanized. An incision was made along the back with a scalpel to expose the spinal cord. Connective tissue was removed using small sharp scissors, and then cleaned spine column was transferred to a petri dish at room temperature. The spinal cord was removed under a dissecting microscope using fine forceps, and the Dorsal Root Ganglia were located (DRG). Whole DRG's were transferred to a clean petri dish containing F-12 (Thermo-Fisher Scientific) media supplemented with 10% fetal calf serum (FCS) and 1% penicillin-streptomycin. DRGs were immediately transferred using fine tweezers to the collagen gel solution. Both control, untreated gels and gels containing 0.05 mg uncoated MNPs and placed in a 255 G fields, were allowed to set and solidify for 40 minutes of within a 37° C. incubator. Media was replaced daily, and neurite sprouting from explant was monitored. Following 1 week in culture neuronal outgrowth was labeled with a mouse anti-Neurofilament H (NF-H) primary antibody overnight at 4° C. (BioLegend, San Diego, USA). Following the incubation, gels were rinsed with PBS and incubated for 45 min at room temperature with Donkey anti mouse IgG H&L conjugated Alexa Fluor 488 for secondary antibody. (Thermo-Fisher Scientific, Pittsburgh, Pa., USA).

Example 1

General Strategy for Creation of a 3D Scaffold In Situ

To create a scaffold that can be aligned dynamically and remotely in situ in response to a pathological need, a 3D scaffold was developed, based on a collagen hydrogel, combined with magnetic nanoparticles. More specifically, magnetic particles were embedded in collagen liquid suspension (FIG. 2A), and the collagen gel was allowed to solidify under a permanent magnetic field (FIG. 2B). Application of the magnetic field during the solidification period enabled the controlled aggregation of magnetic particles within the gel, forming "magnetic particle strings", which aggregate along the magnetic field lines (FIG. 2C). It appears that utilizing this method with different magnetic particles affected gel complex formation dynamics and allowed the inventors to achieve alignment of the collagen fibers. Once the external magnetic field was removed the particle aggregates remained embedded within the collagen gel and gel fibers maintained their induced orientation. Both particles and fibers, may serve as topographic guiding cues for directing neurite outgrowth (FIGS. 2C and 2D).

Example 2

Effect of Magnetic Particles Sizes and Compositions

To better control gel complex structure orientation and in order to achieve maximal collagen fiber alignment, magnetic particles of different sizes and compositions were examined Nano- and micro-particles with different parameters were mixed with a collagen precursor gel solution (collagen-type-I, diluted by the addition of 10×L-15 and brought to neutral pH by 7.5% sodium carbonate, as detailed in Experimental procedures. The liquid solution was then placed on a tunable platform (also referred to herein as a portable stage) between two bar magnets (contained within transverse movable plastic holders (NdFeB, Grade N50, coated NiCuNi, size D18*18 [min]) and allowed to solidify under effective magnetic fields of 162 G to 2110 G in a 25° C. humidified incubator (FIG. 1).

FIG. 3 shows manipulation of line size and width, 3D dispersion as a function of particle size (FIG. 3A, B, C: Si Mag particles of 3 μm; D: MAG/R-DXS 150 nm), magnetic field (FIG. 3B: 1120 G; C, D: 255 G) and gel composition (FIG. 3A, B, D: 1.5 mg/ml; C 3 mg/ml). The collagen fiber alignment in magnetic particle gels was investigated also by confocal reflectance microscopy: FIGS. 4A, 4B show gels containing magnetic particles solidified in the influence of a magnetic field show oriented collagen fibers.

Applying relatively weak magnetic field, around 255 G, has resulted in more uniform distribution of the magnetic strings, therefore, it was chosen as the actuator magnetic field. Two gel concentrations were examined, 3 mg/ml (FIG. 5D, 5E, 5F, bottom panels) and 1.4 mg/ml (FIG. 5A, 5B, 5C, top panels). For both concentrations, the embedded magnetic particles aggregated into distinct line-shaped strings, whereas, without the external magnetic field the particles were homogeneously dispersed within the gel (FIG. 5A, 5D). In the low concentration gels (1.4 mg/ml) magnetic strings tended to aggregate at a lower Z-plane and did not disperse in 3D. In high concentration gels (3 mg/ml) multi-plane aggregation was observed which is beneficial for 3D scaffolds. Therefore, the 3D platforms was based on the 3 mg/ml collagen gels.

The effect of magnetic particle size on gel alignment was next analyzed, focusing on particles at the nanoscale, suitable for tissue engineering platforms. Using uncoated MNPs of 50 nm and 100 nm (hydrodynamic diameter) has demonstrated better gel fiber alignment for the 100 nm MNPs (for both magnetite and maghemite cores).

Notably, functional coating of the MNPs (with dextran-sulfate, starch or citric acid salt, FIG. 6A, 6B, 6C, 6D) has led to less fiber alignment than the uncoated MNPs. To note, embedding in the complex gels micron size magnetic particles (diameter of 1 and 3 μm) also demonstrated non-sufficient level of fiber alignment.

The variability of magnetically induced alignment was further examined using a range of magnetic nanoparticles (MNPs) as alignment actuators. Magnetite particles with various coatings were in embedded in 3 mg/mL collagen suspension (0.05 mg of MP's to 100 μL of collagen suspension). Collagen was allowed to solidify under a magnetic field of 255 G, 570 G or 950 G for 40 minutes in a 25° C. humidified incubator. Collagen fiber alignment was examined via confocal reflectance microscopy (CRM), sample images are shown in FIG. 7. As seen, oleic acid-sodium salt coating under 950 G exhibit strong fiber orientation. High magnification SEM images of collagen gels magnetically oriented via incorporation of Oleic acid sodium salt MNPs and solidified under 950 G are shown in FIG. 8. CRM images were analyzed via FFT analysis and a rate of alignment was measured (FIG. 9A). To determine the importance of the coating the magnetization of each particle (FIG. 9B), was next measured. As shown, there is no correlation between the magnetization of the particles and the degree of alignment induced by the particles.

To expand the variability of the aligned magnetic gel system, iron oxide nanoparticles were synthesized via co-precipitation. FIG. 10A shows a TEM image of uncoated iron oxide nanoparticles having a 10-20 nm core diameter. MNPs were integrated with 3 mg/mL collagen suspension and allowed to solidify under magnetic field of 570 G showing fiber alignment (FIG. 10C) compared to collagen gel control without MNPs and magnetic field (FIG. 10B).

Example 3

Characterization of Gel Complex Formation

To characterize gel complex formation, the uncoated 100 nm MNPs (Magnetite core, average dry diameter of 10 nm) that have resulted in excellent fiber alignment, was further used. Gel was fabricated as previously described, and 0.05 mg of uncoated MNPs were combined in the liquid solution. The gel was allowed to set under the influence of 255 G in a 25° C. incubator for 40 minutes. A scanning electron microscope (SEM) image of a control gel containing the same MNPs that has been solidified without the influence of an external magnetic field, presents no preferred fiber orientation (FIG. 11A). Under an external magnetic field, the fibers of the particle-containing gel tended to align according to the particle strings orientation (FIG. 11B). A confocal reflectance microscopy (CRM) of the 3D collagen gels (illumination with 488 nm, detection between 474 and 494 nm) was next performed (FIG. 11D-11E). It can be seen that the control samples show a random distribution of the collagen fibers, in all dimensions (FIG. 11D), while in the magnetically actuated gels collagen fibers align along the direction of the magnetic particle strings (FIG. 11E and FIG. 12A, 12B, 12C, 12E). In order to obtain a quantitative evaluation of the effect on the fibers images of magnetically aligned gels (SEM and CRM) were compared to control samples either without actuating magnetic fields or without magnetic particles. Two-dimensional (2D) fast Fourier transform (FFT) was calculated for the SEM images (FIG. 11C) and for the CRM images (FIG. 11F). CRM images were acquired from random areas of the gels at different depths (not shown) and demonstrated a significantly higher degree of correlation between fibers in the aligned magnetic gels than in the control gels, solidified under 255 G with no MNPs (an average peak value of 0.06±0.01 [au] and 0.03±0.004 [au] respectively). In addition, using the same FFT analysis, the orientation of fibers of the magnetically actuated gels was compared to the orientation of the corresponding image of particle strings demonstrating closely matched peak angles (FIG. 12D).

To have a better understanding of the gel complex formation along with fiber alignment, time lapse microscopy imaging was performed (NIKON TE2000 with a mounted Retiga camera). Collagen gel samples, with and without MNPs, were imaged along the entire gelation process, starting from the liquid phase and up to 25 min. During spontaneous gel polymerization, collagen nucleates and elongates, creating the hydrogel matrix. This process is usually random, leading to tangled fibers of no discernible organization. Embedding the 100 nm MNPs in the collagen without applying an actuating magnetic field has led to the formation of dispersed aggregates of MNPs with no effect on fiber orientation. Aggregates can move freely when in collagen liquid phase and stabilize during the gelation process. Applying the actuating magnetic field during solidification presents a movement of the forming MNP strings up the magnetic gradient, leading to flow. As gel fibers polymerize the MNP strings are no longer free to move. It seems that the orientation of strings movement together with the collagen flow at the beginning of the gelation phase lead to preferable directionality of the newly formed fibers. Following MNP stabilization, collagen fibers keep elongating, retaining the initial orientation in a template-like manner. To note, gel complexes with less particle movement, such as the gels containing microscale particles under 255 G, demonstrate non-oriented gel fibers.

Rheological measurements have showed that the resulting gels are fairly compliant and correlate previous studies of neuronal growth in hydrogels as well as moduli of nervous tissue. No significant changes of the physical properties of the gels and gelation kinetics have been detected following the addition of MNPs to the gels (FIG. 13A).

Example 4

Directed Neuronal Growth, Leech Neurons Model

Next, to examine the magnetically aligned gel as a scaffold for directed neuronal growth, primary neurons were seeded within the gel, prior to the gelation. Neurons of a simple model system, the medicinal leech (*Hirudo medicinalis*), that can develop at low density cultures allowing for tracking of single neurons and neurites, were employed. Neurons were dissociated out of the adult central nervous system (CNS), similarly to 2D culture protocol as described by Baranes et al., [Baranes, K.; et al., *Biotechnol. Bioeng.* 109, 1791-1797 (2012); and Baranes, K.; et al., *J. Mol. Histol.* 43, 437-447 (2012)] and were incorporated in the collagen gel precursor liquid solution. The gel solution containing magnetic particles and cells was allowed to solidify under an external magnetic field (255 G) for 40 minutes within a 25° C. incubator. Once the field was removed and the solidification process was complete, growth medium was added (conditioned L15) to allow neuronal regeneration.

During the outgrowth period within the gel neurites initiated from the cell soma then branched and developed into a complex 3D dendritic tree. After 7 days of growth, neurons were stained (α-tubulin, Santa Cruz Biotechnology, Inc.) and imaged by confocal microscopy (FIG. 14A). The 3D data from confocal z-stacks was extracted and analyzed semi-automatically using a neurite tracer 44 (ImageJ plugin, US National Institutes of Health, Bethesda, Md.) and a MATLAB script. Then, the representation of the spatial arrangement of each cell was plotted as a cuboid (FIG. 14B) and the aspect ratio between the long axis and the short axis was measured. High aspect ratio represents an elongated neuronal shape and an aspect ratio closer to 1 represents a multidirectional growth. It appears that growth within the oriented gels have led to significantly elongated neuronal shape with an aspect ratio close to 3 (twice the aspect ratio of the control) (FIG. 14C). To examine the effect on the neuronal directionality, the orientation of the longest axis was designated as the direction of neuronal growth and measured the deviation angle Δθ from magnetic string orientation (detailed measurements of single neurons are presented in FIG. 15). Notably, the growth of neurons that regenerated within the aligned gels was co-oriented; the majority of the cells exhibited highly significant correlation with the magnetic line orientation (60% of the cells developed within the range of $\Delta\theta<\pm15°$ compared to the magnetic lines and additional 12% of cells exhibited moderate correlation of cell orientation of $\Delta\theta<\pm30°$; chi-square value of −16.88 df 2; FIG. 14D).

To reveal the nature of neuronal alignment within the magnetically actuated gels, the neuronal growth was examined in several gel complexes with different gel concentrations, particles and magnetic fields. Neurons grown in gels containing aligned magnetic strings but without fiber alignment (for example, 3 mg/mL gels with particles of 1 μm, solidified under 255 G and 3 mg/mL gels with MNPs, solidified under 620 G) have demonstrated less elongation and less directionality (FIG. 16) than within the aligned gel complex (as presented in FIG. 14) suggesting that the induced alignment of collagen fibers is key in neurite pathfinding.

Example 5

Viability Assay of Seeded Leech Neurons

To examine further the scaffold as a regenerative platform, viability of the seeded leech neurons was examined After 7 days in culture, live and dead cells were labeled (Live/Dead imaging kit R37601, Life Technologies). It appears that there was no decrease in viability within the magnetic gel in comparison to the control gels (FIG. 17A) similarly to MNPs effects on viability in previous studies. A standard current-clamp intracellular recording to monitor spike activity was also used. Neuronal spikes were sampled for several neurons demonstrating characteristic spontaneous spikes as well as action potentials in response to 2-10 nA stimuli (FIG. 17B). Moreover, measurements of morphometric parameters of neurons within the magnetically aligned gel demonstrated a similar neurite length, less branched dendritic trees and slightly shorter total tree length, compared to control cells, within gels with no particles or magnetic field (FIG. 17C, 17D, 17E, 17F). Within the aligned gels neurons presented an elongated and directed growth with less branching as can be expected for efficient neuronal pathfinding within an anisotropic environment. Such branching formation and shape maturation have been also observed in other 2D and 3D setups for directed growth.

Example 6

Directed Neuronal Growth, a Mammalian Model

To further validate the tunablity and efficiency of the magnetically aligned gels in directing neuronal growth, a mammalian cell line was next assessed. PC12 rat cells serve as a model of neuronal differentiation. PC12 cells were seeded and the collagen gel was used as the differentiating platform. We embedded PC12 cells in 3 mg/mL gels, and 1.4 mg/mL gels, combined 0.05 mg uncoated MNPs and allowed the gel to solidify under 255 G in a 37° C. incubator. Following treatment with nerve growth factor (NGF), PC12 cells have developed neurites in 3-dimensions within the gel matrix (as specified in Experimental procedures). After 5 days in culture cells were stained and analyzed. As in the primary neurons, PC12 cells grown in the magnetically aligned gels developed co-oriented neurites (FIG. 18A). Growth orientation analysis revealed that 56.5% of the cells exhibited a significant correlation of growth with the magnetic line orientation, within $\Delta\theta<\pm30°$ (FIG. 18C; chi-square value of 9.739 df 2). Within this range, 34.7% exhibited high correlation ($\Delta\theta<\pm15'$; not shown). Additionally, these cells were used to examine the response to magnetically aligned gels of low collagen concentration (FIG. 18B) demonstrating similar trend (FIG. 18D; $\Delta\theta<\pm30°$ chi-square value of 8.313 df 2). To note, within the low concentration gels, oriented neurons were observed more clearly in proximity to the magnetic strings. Since these gels are more diluted and fiber density was lower, neurons have relied on the particles as topographical cues.

MNPs were further functionalized by conjugating Nerve Growth Factor (NGF) to MNPs. (conjugation via PEG linker to fluidMag-PEG/Amine, produce #4131). FIG. 19A shows scheme of MNP conjugation. The effect of NGF conjugated MNPs on collagen fiber orientation and on PC12 differentiation, was next examined. In the presence of NGF PC12 cells grow neuronal process in all directions (FIG. 19B). However, PC12 cells grown within gels oriented by NGF-coated MNPs (950 G) for 1 week exhibit directional neurite growth (FIG. 19C). In the absence of NGF, cells do not grow neuronal processes (FIG. 19D).

In order to further demonstrate the orienting effect of magnetically aligned collagen gels on neurite extension and within a mammalian model, whole mouse Dorsal Root Ganglia (DRG) neurons were encapsulated within aligned gels. Mouse DRG neurons in-vitro show radial outgrowth from their explant, and are known to follow nano topographic cue, and were therefore used to further exemplify the orientation effect of magnetically aligned gels. DRG explants were embedded within collagen solution containing 0.05 mg uncoated MNPs and solidified under 255 G at a 25° C., or maintained in control gels, without MNPs and an external field. Following the gelation period (40 min) the external magnetic field was removed and culture was maintained for 1 week. To validate the guidance of neurite extensions within the aligned gels, gel cultures with anti-neurofilament were immunostained. Within control collagen gels, DRG explants showed extensive neuronal outgrowth with no preferred direction. Within aligned gels, directed neurite extension guided by fiber alignment was observed. FIG. 20 shows a fluorescently labeled neuronal outgrowth from control (FIG. 20A) and magnetically aligned gels (FIG. 20B).

Example 7

Cross Linking of Magnetically Aligned Collagen Gels

To expand the versatility of magnetically aligned gels, the effect of cross linking on collagen gels was next explored. The effect of an in-situ cross-linker, genipin, was examined on magnetically aligned gels.

First, the cross linking effect via the change in spectral properties of collagen induced by cross linking was examined. To 3 mg/mL collagen gels, genipin was added at final concentration of 0.25 or 0.5 mM. The cross-linking of collagen and genipin molecules induced a blue/purple color change. The change in fluorescence was measured for a week post gelation (abs 595 nm fluorescence: ex. 595 nm em. 630 nm). FIG. 21A shows that cross linking was most prominent in the first 72 h following gelation and stabilized following a week post gelation. As expected, 0.5 mM of genipin induced more cross linking then 0.25 mM (FIG. 21A). Rheometry measurements reveled a small increase in modules, as reflected by the complex modulus of the genipin cross-linked gels (0.5 mM) (FIG. 21B).

Cross linked gels showed in FIG. 22A, FIG. 22B and FIG. 22C, exhibit a small decrease in pore size distribution (FIG. 22D) and a significant increase in stability to degradation in collogenase. (FIG. 22E).

Next, the inventors examined the effect of cross linking on magnetic alignment of collagen gels. Oleic acid-sodium salt MNPs were used for these experiments and the gels were allowed to solidify under 950 G at 25° C. for 40 min. Using these parameters, cross-linking with genipin had little influence on fiber orientation, and magnetically induced alignment was maintained (FIG. 23A, FIG. 23B, FIG. 23C and FIG. 24A). The inventors further examined the effect on cell growth. Fibroblast cells (3T3) were incorporated within cross-linked and magnetically aligned gels for 1 week, and show directed growth (FIG. 23A, FIG. 23B and FIG. 23C). Cross linking by 0.5 mM genipin decreased viability of 3T3 cells, compared to 0.25 mM and control samples (FIG. 23D). This effect was further examined on SHSY-5Y neuroblastoma cells which also show directed growth within cross-linked magnetically aligned gels (FIG. 24A) with a similar trend in viability to 3T3 cells (FIG. 24B).

Example 8

Peripheral Nerve Injury In Vivo Model

To evaluate the method and implants of the invention, the effect of magnetically aligned gels is next examined on rat sciatic nerve injury model. Toxicology of injectable collagen gels containing MNPs is evaluated on mice and rat model. Following known procedures, rat full cut sciatic nerve injury model is implemented and collagen gel containing MNPs is injected in a pre-formed clinical grade tube. Magnetic alignment is induced by placing magnet strategically in site for the gelation period in-vivo. The following experimental groups (each group containing 10 animals) were used: (1) control untreated (2) injected magnetically aligned collagen gels; and (3) nerve autologous graft. Following 3 months post-operation functional recovery is assessed, blood brain barrier (BBB) locomotor rating is valued. Collagen gel implant is extracted for evaluation of fiber alignment and integration in-vivo. Clearance of MNPs from rat organs is also investigated. Histological and electrophysiological assays are performed on injury site.

Example 9

Central Nervous System Injury In Vivo Model

Following known procedures, injectable magnetically aligned gels are implemented in Spinal Cord Injury (SPI) rat model, complete and crush model. The gel is injected within the injury site, and magnetic alignment is induced via an external magnetic field. The following experimental groups were examined (each containing 5 animals) of (1) control untreated (2) magnetically aligned gels (3) modified gels containing growth factors. Following a recovery period, BBB locomotor rating is valued. Collagen gel implant is extracted for evaluation of fiber alignment and integration in-vivo. Gel is examined histologically for axonal sprouting.

Example 10

Skin Regeneration In Vivo Model

Alignment of collagen gel and cross-linked gels is investigated for skin regeneration. Keratinocytes are cultured in magnetically aligned collagen gels. Cross-linked gels, or are evaluated as suitable scaffolds for growth. Scratch assay is performed on keratinocyte culture, whereas confluency of 80% is reached a scratch of 100 μm is preformed and regeneration is examined on specific time points (1 h, 3 h, 5 h, 24 h). Groups of (1) control untreated culture (2) injecting collagen gel on scratch wound and (3) injecting magnetically aligned collagen gels, are being investigated.

Moreover, cross-linked and magnetically aligned collagen gels scaffolds are being investigated as preferable directing agents for keratinocyte migration.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A method for guiding growth of a cell, guiding growth of a mixture of cells or guiding growth of cellular extension(s), the method comprising the steps of:

(a) providing at least one biomaterial solution comprising: (i) magnetic particles; and (ii) said cell(s), or plurality of cells of different types, with the proviso that said cell(s), or plurality of cells are not magnetically labeled cells;

(b) providing at least two magnetic sources providing a magnetic field having a strength of between 162 G to 2110 G;

(c) solidifying said biomaterial while applying said magnetic field, thereby aligning along the magnetic field lines, at least one of said magnetic particles or aggregates thereof and components of said biomaterial; and (d) allowing growth of at least one of cell(s) and cellular extension(s) within said solidified biomaterial, thereby guiding the growth of said cell(s) and/or cellular extension(s) longitudinally oriented along at least one of the aligned magnetic particles or aggregates thereof and the aligned components of said biomaterial.

2. The method according to claim 1, wherein said biomaterial solution is liquid hydrogel.

3. The method according to claim 2, wherein said hydrogel is a collagen solution and wherein said component(s) of said biomaterial are at least one of collagen fibrils and collagen fibers.

4. The method according to claim 1, wherein said magnetic particles comprising any one of a magnetite core, a maghemite core, Ferrite core or iron oxide core and wherein said magnetic particles are uncoated or coated magnetic particles.

5. The method according to claim 4, wherein said magnetic particles are oleic acid-sodium salt coated magnetic particles.

6. The method according to claim 4, wherein said magnetic particles are at least one of conjugated, attached, linked, mixed with, encapsulated within, or encapsulating at least one of cell growth agent(s), cell guiding agent(s) and cell selective agent(s).

7. The method according to claim 4, wherein the diameter of said magnetic particles ranges between about 0.1 nm to 100 μm.

8. The method according to claim 1, wherein said magnetic sources are portable magnetic sources comprised within a device and held by or connected to adjustable holders.

9. The method according to claim 1, wherein said cell are at least one of neuronal cells or skin cells.

10. The method according to claim 1, wherein the method is performed in situ for guiding cell growth in a subject in need thereof.

11. A method for treating or repairing tissue or organ injury in a subject, comprising the steps of:

(a) providing into the site of said tissue or organ injury, at least one biomaterial solution comprising: (i) magnetic particles; and (ii) cell(s), or plurality of cells of different types, with the proviso that said cell(s), or plurality of cells are not magnetically labeled cells;

(b) providing at least two magnetic sources providing a magnetic field having a strength of between 162 G to 2110 G;

(c) solidifying said biomaterial while applying said magnetic field, thereby aligning along the magnetic field lines, at least one of said magnetic particles or aggregates thereof and components of said biomaterial; and (d) allowing growth of at least one of cell(s) and cellular extension(s) within said solidified biomaterial, wherein the growth of said cell(s) and/or cellular extension(s) is longitudinally oriented along at least one of the aligned magnetic particles or aggregates thereof and the aligned components of said biomaterial, thereby treating or repairing tissue injury.

12. A method for promoting wound healing in a subject, comprising the steps of:

(a) providing into the site of said wound at least one biomaterial solution comprising: (i) magnetic particles; and (ii) cell(s), or plurality of cells of different types, with the proviso that said cell(s), or plurality of cells are not magnetically labeled cells;

(b) providing at least two magnetic sources providing a magnetic field having a strength of between 162 G to 2110 G;

(c) solidifying said biomaterial while applying said magnetic field, thereby aligning at least one of said magnetic particles or aggregates thereof and components of said biomaterial, along the magnetic field lines;

(d) allowing growth of at least one of cell(s) and cellular extension(s) within said solidified biomaterial, wherein the growth of said cell(s) and/or cellular extension(s) is longitudinally oriented along at least one of the aligned magnetic particles or aggregates thereof and the aligned components of said biomaterial, thereby promoting wound healing.

13. The method according to claim 11, wherein the biomaterial solution is provided and placed in the injured tissue within an adjustable biodegradable mold.

14. The method according to claim 11, wherein said cell are at least one of neuronal cells or skin cells and wherein said cells are of an autologous or allogenic source.

15. The method according to claim 11, for treating or repairing a nerve injury in a subject, wherein in step (a), at least one biomaterial solution comprising: (i) magnetic particles; and (ii) neuronal cell(s), or mixture of neuronal cells, is provided into the site of said nerve injury.

* * * * *

SEQUENCE LISTING

```
<160> NUMBER OF SEQ ID NOS: 6

<210> SEQ ID NO 1
<211> LENGTH: 1464
<212> TYPE: PRT
<213> ORGANISM: Homo sapiens

<400> SEQUENCE: 1

Met Phe Ser Phe Val Asp Leu Arg Leu Leu Leu Leu Leu Ala Ala Thr
1               5                   10                  15

Ala Leu Leu Thr His Gly Gln Glu Glu Gly Gln Val Glu Gly Gln Asp
            20                  25                  30

Glu Asp Ile Pro Pro Ile Thr Cys Val Gln Asn Gly Leu Arg Tyr His
        35                  40                  45

Asp Arg Asp Val Trp Lys Pro Glu Pro Cys Arg Ile Cys Val Cys Asp
    50                  55                  60

Asn Gly Lys Val Leu Cys Asp Asp Val Ile Cys Asp Glu Thr Lys Asn
65                  70                  75                  80

Cys Pro Gly Ala Glu Val Pro Glu Gly Glu Cys Cys Pro Val Cys Pro
                85                  90                  95

Asp Gly Ser Glu Ser Pro Thr Asp Gln Glu Thr Thr Gly Val Glu Gly
            100                 105                 110

Pro Lys Gly Asp Thr Gly Pro Arg Gly Pro Arg Gly Pro Ala Gly Pro
        115                 120                 125

Pro Gly Arg Asp Gly Ile Pro Gly Gln Pro Gly Leu Pro Gly Pro Pro
    130                 135                 140

Gly Pro Pro Gly Pro Pro Gly Pro Pro Gly Leu Gly Gly Asn Phe Ala
145                 150                 155                 160

Pro Gln Leu Ser Tyr Gly Tyr Asp Glu Lys Ser Thr Gly Gly Ile Ser
                165                 170                 175

Val Pro Gly Pro Met Gly Pro Ser Gly Pro Arg Gly Leu Pro Gly Pro
            180                 185                 190

Pro Gly Ala Pro Gly Pro Gln Gly Phe Gln Gly Pro Pro Gly Glu Pro
        195                 200                 205

Gly Glu Pro Gly Ala Ser Gly Pro Met Gly Pro Arg Gly Pro Pro Gly
    210                 215                 220

Pro Pro Gly Lys Asn Gly Asp Asp Gly Glu Ala Gly Lys Pro Gly Arg
225                 230                 235                 240
```

```
Pro Gly Glu Arg Gly Pro Pro Gly Pro Gln Gly Ala Arg Gly Leu Pro
                245                 250                 255

Gly Thr Ala Gly Leu Pro Gly Met Lys Gly His Arg Gly Phe Ser Gly
            260                 265                 270

Leu Asp Gly Ala Lys Gly Asp Ala Gly Pro Ala Gly Pro Lys Gly Glu
        275                 280                 285

Pro Gly Ser Pro Gly Glu Asn Gly Ala Pro Gly Gln Met Gly Pro Arg
    290                 295                 300

Gly Leu Pro Gly Glu Arg Gly Arg Pro Gly Ala Pro Gly Pro Ala Gly
305                 310                 315                 320

Ala Arg Gly Asn Asp Gly Ala Thr Gly Ala Ala Gly Pro Pro Gly Pro
                325                 330                 335

Thr Gly Pro Ala Gly Pro Pro Gly Phe Pro Gly Ala Val Gly Ala Lys
            340                 345                 350

Gly Glu Ala Gly Pro Gln Gly Pro Arg Gly Ser Glu Gly Pro Gln Gly
        355                 360                 365

Val Arg Gly Glu Pro Gly Pro Pro Gly Pro Ala Gly Ala Ala Gly Pro
    370                 375                 380

Ala Gly Asn Pro Gly Ala Asp Gly Gln Pro Gly Ala Lys Gly Ala Asn
385                 390                 395                 400

Gly Ala Pro Gly Ile Ala Gly Ala Pro Gly Phe Pro Gly Ala Arg Gly
                405                 410                 415

Pro Ser Gly Pro Gln Gly Pro Gly Gly Pro Pro Gly Pro Lys Gly Asn
            420                 425                 430

Ser Gly Glu Pro Gly Ala Pro Gly Ser Lys Gly Asp Thr Gly Ala Lys
        435                 440                 445

Gly Glu Pro Gly Pro Val Gly Val Gln Gly Pro Pro Gly Pro Ala Gly
    450                 455                 460

Glu Glu Gly Lys Arg Gly Ala Arg Gly Glu Pro Gly Pro Thr Gly Leu
465                 470                 475                 480

Pro Gly Pro Pro Gly Glu Arg Gly Gly Pro Gly Ser Arg Gly Phe Pro
                485                 490                 495

Gly Ala Asp Gly Val Ala Gly Pro Lys Gly Pro Ala Gly Glu Arg Gly
            500                 505                 510

Ser Pro Gly Pro Ala Gly Pro Lys Gly Ser Pro Gly Glu Ala Gly Arg
        515                 520                 525

Pro Gly Glu Ala Gly Leu Pro Gly Ala Lys Gly Leu Thr Gly Ser Pro
    530                 535                 540

Gly Ser Pro Gly Pro Asp Gly Lys Thr Gly Pro Pro Gly Pro Ala Gly
545                 550                 555                 560

Gln Asp Gly Arg Pro Gly Pro Pro Gly Pro Pro Gly Ala Arg Gly Gln
                565                 570                 575

Ala Gly Val Met Gly Phe Pro Gly Pro Lys Gly Ala Ala Gly Glu Pro
            580                 585                 590

Gly Lys Ala Gly Glu Arg Gly Val Pro Gly Pro Pro Gly Ala Val Gly
        595                 600                 605

Pro Ala Gly Lys Asp Gly Glu Ala Gly Ala Gln Gly Pro Pro Gly Pro
    610                 615                 620

Ala Gly Pro Ala Gly Glu Arg Gly Glu Gln Gly Pro Ala Gly Ser Pro
625                 630                 635                 640

Gly Phe Gln Gly Leu Pro Gly Pro Ala Gly Pro Pro Gly Glu Ala Gly
                645                 650                 655
```

```
Lys Pro Gly Glu Gln Gly Val Pro Gly Asp Leu Gly Ala Pro Gly Pro
            660                 665                 670

Ser Gly Ala Arg Gly Glu Arg Gly Phe Pro Gly Glu Arg Gly Val Gln
        675                 680                 685

Gly Pro Pro Gly Pro Ala Gly Pro Arg Gly Ala Asn Gly Ala Pro Gly
    690                 695                 700

Asn Asp Gly Ala Lys Gly Asp Ala Gly Ala Pro Gly Ala Pro Gly Ser
705                 710                 715                 720

Gln Gly Ala Pro Gly Leu Gln Gly Met Pro Gly Glu Arg Gly Ala Ala
                725                 730                 735

Gly Leu Pro Gly Pro Lys Gly Asp Arg Gly Asp Ala Gly Pro Lys Gly
            740                 745                 750

Ala Asp Gly Ser Pro Gly Lys Asp Gly Val Arg Gly Leu Thr Gly Pro
        755                 760                 765

Ile Gly Pro Pro Gly Pro Ala Gly Ala Pro Gly Asp Lys Gly Glu Ser
    770                 775                 780

Gly Pro Ser Gly Pro Ala Gly Pro Thr Gly Ala Arg Gly Ala Pro Gly
785                 790                 795                 800

Asp Arg Gly Glu Pro Gly Pro Pro Gly Pro Ala Gly Phe Ala Gly Pro
                805                 810                 815

Pro Gly Ala Asp Gly Gln Pro Gly Ala Lys Gly Glu Pro Gly Asp Ala
            820                 825                 830

Gly Ala Lys Gly Asp Ala Gly Pro Pro Gly Pro Ala Gly Pro Ala Gly
        835                 840                 845

Pro Pro Gly Pro Ile Gly Asn Val Gly Ala Pro Gly Ala Lys Gly Ala
    850                 855                 860

Arg Gly Ser Ala Gly Pro Pro Gly Ala Thr Gly Phe Pro Gly Ala Ala
865                 870                 875                 880

Gly Arg Val Gly Pro Pro Gly Pro Ser Gly Asn Ala Gly Pro Pro Gly
                885                 890                 895

Pro Pro Gly Pro Ala Gly Lys Glu Gly Gly Lys Gly Pro Arg Gly Glu
            900                 905                 910

Thr Gly Pro Ala Gly Arg Pro Gly Glu Val Gly Pro Pro Gly Pro Pro
        915                 920                 925

Gly Pro Ala Gly Glu Lys Gly Ser Pro Gly Ala Asp Gly Pro Ala Gly
    930                 935                 940

Ala Pro Gly Thr Pro Gly Pro Gln Gly Ile Ala Gly Gln Arg Gly Val
945                 950                 955                 960

Val Gly Leu Pro Gly Gln Arg Gly Glu Arg Gly Phe Pro Gly Leu Pro
                965                 970                 975

Gly Pro Ser Gly Glu Pro Gly Lys Gln Gly Pro Ser Gly Ala Ser Gly
            980                 985                 990

Glu Arg Gly Pro Pro Gly Pro Met  Gly Pro Pro Gly Leu  Ala Gly Pro
        995                 1000                1005

Pro Gly  Glu Ser Gly Arg Glu  Gly Ala Pro Gly Ala  Glu Gly Ser
    1010                 1015                 1020

Pro Gly  Arg Asp Gly Ser Pro  Gly Ala Lys Gly Asp  Arg Gly Glu
    1025                 1030                 1035

Thr Gly  Pro Ala Gly Pro Pro  Gly Ala Pro Gly Ala  Pro Gly Ala
    1040                 1045                 1050

Pro Gly  Pro Val Gly Pro Ala  Gly Lys Ser Gly Asp  Arg Gly Glu
    1055                 1060                 1065
```

-continued

```
Thr Gly  Pro Ala Gly Pro Ala  Gly Pro Val Gly Pro  Val Gly Ala
    1070                 1075                 1080

Arg Gly  Pro Ala Gly Pro Gln  Gly Pro Arg Gly Asp  Lys Gly Glu
    1085                 1090                 1095

Thr Gly  Glu Gln Gly Asp Arg  Gly Ile Lys Gly His  Arg Gly Phe
    1100                 1105                 1110

Ser Gly  Leu Gln Gly Pro Pro  Gly Pro Pro Gly Ser  Pro Gly Glu
    1115                 1120                 1125

Gln Gly  Pro Ser Gly Ala Ser  Gly Pro Ala Gly Pro  Arg Gly Pro
    1130                 1135                 1140

Pro Gly  Ser Ala Gly Ala Pro  Gly Lys Asp Gly Leu  Asn Gly Leu
    1145                 1150                 1155

Pro Gly  Pro Ile Gly Pro Pro  Gly Pro Arg Gly Arg  Thr Gly Asp
    1160                 1165                 1170

Ala Gly  Pro Val Gly Pro Pro  Gly Pro Pro Gly Pro  Pro Gly Pro
    1175                 1180                 1185

Pro Gly  Pro Pro Ser Ala Gly  Phe Asp Phe Ser Phe  Leu Pro Gln
    1190                 1195                 1200

Pro Pro  Gln Glu Lys Ala His  Asp Gly Gly Arg Tyr  Tyr Arg Ala
    1205                 1210                 1215

Asp Asp  Ala Asn Val Val Arg  Asp Arg Asp Leu Glu  Val Asp Thr
    1220                 1225                 1230

Thr Leu  Lys Ser Leu Ser Gln  Gln Ile Glu Asn Ile  Arg Ser Pro
    1235                 1240                 1245

Glu Gly  Ser Arg Lys Asn Pro  Ala Arg Thr Cys Arg  Asp Leu Lys
    1250                 1255                 1260

Met Cys  His Ser Asp Trp Lys  Ser Gly Glu Tyr Trp  Ile Asp Pro
    1265                 1270                 1275

Asn Gln  Gly Cys Asn Leu Asp  Ala Ile Lys Val Phe  Cys Asn Met
    1280                 1285                 1290

Glu Thr  Gly Glu Thr Cys Val  Tyr Pro Thr Gln Pro  Ser Val Ala
    1295                 1300                 1305

Gln Lys  Asn Trp Tyr Ile Ser  Lys Asn Pro Lys Asp  Lys Arg His
    1310                 1315                 1320

Val Trp  Phe Gly Glu Ser Met  Thr Asp Gly Phe Gln  Phe Glu Tyr
    1325                 1330                 1335

Gly Gly  Gln Gly Ser Asp Pro  Ala Asp Val Ala Ile  Gln Leu Thr
    1340                 1345                 1350

Phe Leu  Arg Leu Met Ser Thr  Glu Ala Ser Gln Asn  Ile Thr Tyr
    1355                 1360                 1365

His Cys  Lys Asn Ser Val Ala  Tyr Met Asp Gln Gln  Thr Gly Asn
    1370                 1375                 1380

Leu Lys  Lys Ala Leu Leu Leu  Gln Gly Ser Asn Glu  Ile Glu Ile
    1385                 1390                 1395

Arg Ala  Glu Gly Asn Ser Arg  Phe Thr Tyr Ser Val  Thr Val Asp
    1400                 1405                 1410

Gly Cys  Thr Ser His Thr Gly  Ala Trp Gly Lys Thr  Val Ile Glu
    1415                 1420                 1425

Tyr Lys  Thr Thr Lys Thr Ser  Arg Leu Arg Ile Ile  Asp Val Ala
    1430                 1435                 1440
```

```
Pro Leu  Asp Val Gly Ala Pro  Asp Gln Glu Phe Gly  Phe Asp Val
    1445                 1450                 1455

Gly His  Val Cys Phe Leu
    1460


<210> SEQ ID NO 2
<211> LENGTH: 4395
<212> TYPE: DNA
<213> ORGANISM: Homo sapiens

<400> SEQUENCE: 2

atgttcagct ttgtggacct ccggctcctg ctcctcttag cggccaccgc cctcctgacg     60

cacggccaag aggaaggcca agtcgagggc caagacgaag acatcccacc aatcacctgc    120

gtacagaacg gcctcaggta ccatgaccga gacgtgtgga aacccgagcc ctgccggatc    180

tgcgtctgcg acaacggcaa ggtgttgtgc gatgacgtga tctgtgacga gaccaagaac    240

tgccccggcg ccgaagtccc cgagggcgag tgctgtcccg tctgccccga cggctcagag    300

tcacccaccg accaagaaac caccggcgtc gagggaccca agggagacac tggcccccga    360

ggcccaaggg gacccgcagg cccccctggc cgagatggca tccctggaca gcctggactt    420

cccggacccc ccggaccccc cggacctccc ggacccccctg gcctcggagg aaactttgct    480

ccccagctgt cttatggcta tgatgagaaa tcaaccggag gaatttccgt gcctggcccc    540

atgggtccct ctggtcctcg tggtctccct ggccccccctg gtgcacctgg tccccaaggc    600

ttccaaggtc cccctggtga gcctggcgag cctggagctt caggtcccat gggtccccga    660

ggtcccccag gtcccccctgg aaagaatgga gatgatgggg aagctggaaa acctggtcgt    720

cctggtgagc gtgggcctcc tgggcctcag ggtgctcgag gattgcccgg aacagctggc    780

ctccctggaa tgaagggaca cagaggtttc agtggtttgg atggtgccaa gggagatgct    840

ggtcctgctg gtcctaaggg tgagcctggc agccctggtg aaaatggagc tcctggtcag    900

atgggccccc gtggcctgcc tggtgagaga ggtcgccctg gagcccctgg ccctgctggt    960

gctcgtggaa atgatggtgc tactggtgct gccgggcccc ctggtcccac cggccccgct   1020

ggtcctcctg gcttccctgg tgctgttggt gctaagggtg aagctggtcc ccaagggccc   1080

cgaggctctg aaggtcccca gggtgtgcgt ggtgagcctg gcccccctgg ccctgctggt   1140

gctgctggcc ctgctggaaa ccctggtgct gatggacagc ctggtgctaa aggtgccaat   1200

ggtgctcctg gtattgctgg tgctcctggc ttccctggtg cccgaggccc ctctggaccc   1260

cagggccccg gcggccctcc tggtcccaag ggtaacagcg gtgaacctgg tgctcctggc   1320

agcaaaggag acactggtgc taagggagag cctggccctg ttggtgttca aggacccccct   1380

ggccctgctg gagaggaagg aaagcgagga gctcgaggtg aacccggacc cactggcctg   1440

cccggacccc ctggcgagcg tggtggacct ggtagccgtg gtttccctgg cgcagatggt   1500

gttgctggtc ccaagggtcc cgctggtgaa cgtggttctc ctggccctgc tggccccaaa   1560

ggatctcctg gtgaagctgg tcgtcccggt gaagctggtc tgcctggtgc caagggtctg   1620

actggaagcc ctggcagccc tggtcctgat ggcaaaactg gccccccctgg tcccgccggt   1680

caagatggtc gccccggacc cccaggccca cctggtgccc gtggtcaggc tggtgtgatg   1740

ggattccctg gacctaaagg tgctgctgga gagcccggca aggctggaga gcgaggtgtt   1800

cccggacccc ctggcgctgt cggtcctgct ggcaaagatg gagaggctgg agctcaggga   1860

cccccctggcc ctgctggtcc cgctggcgag agaggtgaac aaggccctgc tggctccccc   1920
```

-continued

```
ggattccagg gtctccctgg tcctgctggt cctccaggtg aagcaggcaa acctggtgaa   1980
cagggtgttc ctggagacct tggcgcccct ggcccctctg gagcaagagg cgagagaggt   2040
ttccctggcg agcgtggtgt gcaaggtccc cctggtcctg ctggtccccg aggggccaac   2100
ggtgctcccg gcaacgatgg tgctaagggt gatgctggtg cccctggagc tcccggtagc   2160
cagggcgccc ctggccttca gggaatgcct ggtgaacgtg gtgcagctgg tcttccaggg   2220
cctaagggtg acagaggtga tgctggtccc aaaggtgctg atggctctcc tggcaaagat   2280
ggcgtccgtg gtctgaccgg ccccattggt cctcctggcc ctgctggtgc ccctggtgac   2340
aagggtgaaa gtggtcccag cggccctgct ggtcccactg gagctcgtgg tgcccccgga   2400
gaccgtggtg agcctggtcc ccccggccct gctggctttg ctggcccccc tggtgctgac   2460
ggccaacctg gtgctaaagg cgaacctggt gatgctggtg ctaaaggcga tgctggtccc   2520
cctggccctg ccggacccgc tggacccccct ggccccattg gtaatgttgg tgctcctgga   2580
gccaaaggtg ctcgcggcag cgctggtccc cctggtgcta ctggtttccc tggtgctgct   2640
ggccgagtcg gtcctcctgg cccctctgga aatgctggac cccctggccc tcctggtcct   2700
gctggcaaag aaggcggcaa aggtccccgt ggtgagactg gccctgctgg acgtcctggt   2760
gaagttggtc cccctggtcc ccctggccct gctggcgaga aaggatcccc tggtgctgat   2820
ggtcctgctg gtgctcctgg tactcccggg cctcaaggta ttgctggaca gcgtggtgtg   2880
gtcggcctgc ctggtcagag aggagagaga ggcttccctg gtcttcctgg cccctctggt   2940
gaacctggca aacaaggtcc ctctggagca agtggtgaac gtggtccccc tggtcccatg   3000
ggcccccctg gattggctgg acccccctggt gaatctggac gtgagggggc tcctggtgcc   3060
gaaggttccc ctggacgaga cggttctcct ggcgccaagg gtgaccgtgg tgagaccggc   3120
cccgctggac cccctggtgc tcctggtgct cctggtgccc ctggccccgt tggccctgct   3180
ggcaagagtg gtgatcgtgg tgagactggt cctgctggtc ccgccggtcc tgtcggccct   3240
gttggcgccc gtggccccgc cggaccccaa ggcccacgtg gtgacaaggg tgagacaggc   3300
gaacagggcg acagaggcat aaagggtcac cgtggcttct ctggcctcca gggtcccccct   3360
ggccctcctg gctctcctgg tgaacaaggt ccctctggag cctctggtcc tgctggtccc   3420
cgaggtcccc ctggctctgc tggtgctcct ggcaaagatg gactcaacgg tctccctggc   3480
cccattgggc cccctggtcc tcgcggtcgc actggtgatg ctggtcctgt tggtcccccc   3540
ggccctcctg gacctcctgg tccccctggt cctcccagcg ctggtttcga cttcagcttc   3600
ctgccccagc cacctcaaga gaaggctcac gatggtggcc gctactaccg ggctgatgat   3660
gccaatgtgg ttcgtgaccg tgacctcgag gtggacacca ccctcaagag cctgagccag   3720
cagatcgaga acatccggag cccagagggc agccgcaaga accccgcccg cacctgccgt   3780
gacctcaaga tgtgccactc tgactggaag agtggagagt actggattga ccccaaccaa   3840
ggctgcaacc tggatgccat caaagtcttc tgcaacatgg agactggtga gacctgcgtg   3900
taccccactc agcccagtgt ggcccagaag aactggtaca tcagcaagaa ccccaaggac   3960
aagaggcatg tctggttcgg cgagagcatg accgatggat tccagttcga gtatggcggc   4020
cagggctccg accctgccga tgtggccatc cagctgacct tcctgcgcct gatgtccacc   4080
gaggcctccc agaacatcac ctaccactgc aagaacagcg tggcctacat ggaccagcag   4140
actggcaacc tcaagaaggc cctgctcctc cagggctcca acgagatcga gatccgcgcc   4200
gagggcaaca gccgcttcac ctacagcgtc actgtcgatg gctgcacgag tcacaccgga   4260
gcctggggca agacagtgat tgaatacaaa accaccaaga cctcccgcct gcgcatcatc   4320
```

```
gatgtggccc ccttggacgt tggtgcccca gaccaggaat tcggcttcga cgttggccat   4380

gtctgcttcc tgtaa                                                    4395


<210> SEQ ID NO 3
<211> LENGTH: 1366
<212> TYPE: PRT
<213> ORGANISM: Homo sapiens

<400> SEQUENCE: 3

Met Leu Ser Phe Val Asp Thr Arg Thr Leu Leu Leu Leu Ala Val Thr
1               5                   10                  15

Leu Cys Leu Ala Thr Cys Gln Ser Leu Gln Glu Glu Thr Val Arg Lys
            20                  25                  30

Gly Pro Ala Gly Asp Arg Gly Pro Arg Gly Glu Arg Gly Pro Pro Gly
        35                  40                  45

Pro Pro Gly Arg Asp Gly Glu Asp Gly Pro Thr Gly Pro Pro Gly Pro
    50                  55                  60

Pro Gly Pro Pro Gly Pro Pro Gly Leu Gly Gly Asn Phe Ala Ala Gln
65                  70                  75                  80

Tyr Asp Gly Lys Gly Val Gly Leu Gly Pro Gly Pro Met Gly Leu Met
                85                  90                  95

Gly Pro Arg Gly Pro Pro Gly Ala Ala Gly Ala Pro Gly Pro Gln Gly
            100                 105                 110

Phe Gln Gly Pro Ala Gly Glu Pro Gly Glu Pro Gly Gln Thr Gly Pro
        115                 120                 125

Ala Gly Ala Arg Gly Pro Ala Gly Pro Pro Gly Lys Ala Gly Glu Asp
    130                 135                 140

Gly His Pro Gly Lys Pro Gly Arg Pro Gly Glu Arg Gly Val Val Gly
145                 150                 155                 160

Pro Gln Gly Ala Arg Gly Phe Pro Gly Thr Pro Gly Leu Pro Gly Phe
                165                 170                 175

Lys Gly Ile Arg Gly His Asn Gly Leu Asp Gly Leu Lys Gly Gln Pro
            180                 185                 190

Gly Ala Pro Gly Val Lys Gly Glu Pro Gly Ala Pro Gly Glu Asn Gly
        195                 200                 205

Thr Pro Gly Gln Thr Gly Ala Arg Gly Leu Pro Gly Glu Arg Gly Arg
    210                 215                 220

Val Gly Ala Pro Gly Pro Ala Gly Ala Arg Gly Ser Asp Gly Ser Val
225                 230                 235                 240

Gly Pro Val Gly Pro Ala Gly Pro Ile Gly Ser Ala Gly Pro Pro Gly
                245                 250                 255

Phe Pro Gly Ala Pro Gly Pro Lys Gly Glu Ile Gly Ala Val Gly Asn
            260                 265                 270

Ala Gly Pro Ala Gly Pro Ala Gly Pro Arg Gly Glu Val Gly Leu Pro
        275                 280                 285

Gly Leu Ser Gly Pro Val Gly Pro Pro Gly Asn Pro Gly Ala Asn Gly
    290                 295                 300

Leu Thr Gly Ala Lys Gly Ala Ala Gly Leu Pro Gly Val Ala Gly Ala
305                 310                 315                 320

Pro Gly Leu Pro Gly Pro Arg Gly Ile Pro Gly Pro Val Gly Ala Ala
                325                 330                 335

Gly Ala Thr Gly Ala Arg Gly Leu Val Gly Glu Pro Gly Pro Ala Gly
            340                 345                 350
```

-continued

```
Ser Lys Gly Glu Ser Gly Asn Lys Gly Glu Pro Gly Ser Ala Gly Pro
        355                 360                 365

Gln Gly Pro Pro Gly Pro Ser Gly Glu Glu Gly Lys Arg Gly Pro Asn
    370                 375                 380

Gly Glu Ala Gly Ser Ala Gly Pro Pro Gly Pro Pro Gly Leu Arg Gly
385                 390                 395                 400

Ser Pro Gly Ser Arg Gly Leu Pro Gly Ala Asp Gly Arg Ala Gly Val
                405                 410                 415

Met Gly Pro Pro Gly Ser Arg Gly Ala Ser Gly Pro Ala Gly Val Arg
            420                 425                 430

Gly Pro Asn Gly Asp Ala Gly Arg Pro Gly Glu Pro Gly Leu Met Gly
        435                 440                 445

Pro Arg Gly Leu Pro Gly Ser Pro Gly Asn Ile Gly Pro Ala Gly Lys
    450                 455                 460

Glu Gly Pro Val Gly Leu Pro Gly Ile Asp Gly Arg Pro Gly Pro Ile
465                 470                 475                 480

Gly Pro Ala Gly Ala Arg Gly Glu Pro Gly Asn Ile Gly Phe Pro Gly
                485                 490                 495

Pro Lys Gly Pro Thr Gly Asp Pro Gly Lys Asn Gly Asp Lys Gly His
            500                 505                 510

Ala Gly Leu Ala Gly Ala Arg Gly Ala Pro Gly Pro Asp Gly Asn Asn
        515                 520                 525

Gly Ala Gln Gly Pro Pro Gly Pro Gln Gly Val Gln Gly Gly Lys Gly
    530                 535                 540

Glu Gln Gly Pro Ala Gly Pro Pro Gly Phe Gln Gly Leu Pro Gly Pro
545                 550                 555                 560

Ser Gly Pro Ala Gly Glu Val Gly Lys Pro Gly Glu Arg Gly Leu His
                565                 570                 575

Gly Glu Phe Gly Leu Pro Gly Pro Ala Gly Pro Arg Gly Glu Arg Gly
            580                 585                 590

Pro Pro Gly Glu Ser Gly Ala Ala Gly Pro Thr Gly Pro Ile Gly Ser
        595                 600                 605

Arg Gly Pro Ser Gly Pro Pro Gly Pro Asp Gly Asn Lys Gly Glu Pro
    610                 615                 620

Gly Val Val Gly Ala Val Gly Thr Ala Gly Pro Ser Gly Pro Ser Gly
625                 630                 635                 640

Leu Pro Gly Glu Arg Gly Ala Ala Gly Ile Pro Gly Gly Lys Gly Glu
                645                 650                 655

Lys Gly Glu Pro Gly Leu Arg Gly Glu Ile Gly Asn Pro Gly Arg Asp
            660                 665                 670

Gly Ala Arg Gly Ala Pro Gly Ala Val Gly Ala Pro Gly Pro Ala Gly
        675                 680                 685

Ala Thr Gly Asp Arg Gly Glu Ala Gly Ala Ala Gly Pro Ala Gly Pro
    690                 695                 700

Ala Gly Pro Arg Gly Ser Pro Gly Glu Arg Gly Glu Val Gly Pro Ala
705                 710                 715                 720

Gly Pro Asn Gly Phe Ala Gly Pro Ala Gly Ala Ala Gly Gln Pro Gly
                725                 730                 735

Ala Lys Gly Glu Arg Gly Ala Lys Gly Pro Lys Gly Glu Asn Gly Val
            740                 745                 750

Val Gly Pro Thr Gly Pro Val Gly Ala Ala Gly Pro Ala Gly Pro Asn
        755                 760                 765
```

```
Gly Pro Pro Gly Pro Ala Gly Ser Arg Gly Asp Gly Gly Pro Pro Gly
    770                 775                 780

Met Thr Gly Phe Pro Gly Ala Ala Gly Arg Thr Gly Pro Pro Gly Pro
785                 790                 795                 800

Ser Gly Ile Ser Gly Pro Pro Gly Pro Pro Gly Pro Ala Gly Lys Glu
                805                 810                 815

Gly Leu Arg Gly Pro Arg Gly Asp Gln Gly Pro Val Gly Arg Thr Gly
            820                 825                 830

Glu Val Gly Ala Val Gly Pro Pro Gly Phe Ala Gly Glu Lys Gly Pro
        835                 840                 845

Ser Gly Glu Ala Gly Thr Ala Gly Pro Pro Gly Thr Pro Gly Pro Gln
    850                 855                 860

Gly Leu Leu Gly Ala Pro Gly Ile Leu Gly Leu Pro Gly Ser Arg Gly
865                 870                 875                 880

Glu Arg Gly Leu Pro Gly Val Ala Gly Ala Val Gly Glu Pro Gly Pro
                885                 890                 895

Leu Gly Ile Ala Gly Pro Pro Gly Ala Arg Gly Pro Pro Gly Ala Val
            900                 905                 910

Gly Ser Pro Gly Val Asn Gly Ala Pro Gly Glu Ala Gly Arg Asp Gly
        915                 920                 925

Asn Pro Gly Asn Asp Gly Pro Pro Gly Arg Asp Gly Gln Pro Gly His
    930                 935                 940

Lys Gly Glu Arg Gly Tyr Pro Gly Asn Ile Gly Pro Val Gly Ala Ala
945                 950                 955                 960

Gly Ala Pro Gly Pro His Gly Pro Val Gly Pro Ala Gly Lys His Gly
                965                 970                 975

Asn Arg Gly Glu Thr Gly Pro Ser Gly Pro Val Gly Pro Ala Gly Ala
            980                 985                 990

Val Gly Pro Arg Gly Pro Ser Gly  Pro Gln Gly Ile Arg  Gly Asp Lys
        995                 1000                 1005

Gly Glu  Pro Gly Glu Lys Gly  Pro Arg Gly Leu Pro  Gly Leu Lys
    1010                 1015                 1020

Gly His  Asn Gly Leu Gln Gly  Leu Pro Gly Ile Ala  Gly His His
    1025                 1030                 1035

Gly Asp  Gln Gly Ala Pro Gly  Ser Val Gly Pro Ala  Gly Pro Arg
    1040                 1045                 1050

Gly Pro  Ala Gly Pro Ser Gly  Pro Ala Gly Lys Asp  Gly Arg Thr
    1055                 1060                 1065

Gly His  Pro Gly Thr Val Gly  Pro Ala Gly Ile Arg  Gly Pro Gln
    1070                 1075                 1080

Gly His  Gln Gly Pro Ala Gly  Pro Pro Gly Pro Pro  Gly Pro Pro
    1085                 1090                 1095

Gly Pro  Pro Gly Val Ser Gly  Gly Gly Tyr Asp Phe  Gly Tyr Asp
    1100                 1105                 1110

Gly Asp  Phe Tyr Arg Ala Asp  Gln Pro Arg Ser Ala  Pro Ser Leu
    1115                 1120                 1125

Arg Pro  Lys Asp Tyr Glu Val  Asp Ala Thr Leu Lys  Ser Leu Asn
    1130                 1135                 1140

Asn Gln  Ile Glu Thr Leu Leu  Thr Pro Glu Gly Ser  Arg Lys Asn
    1145                 1150                 1155

Pro Ala  Arg Thr Cys Arg Asp  Leu Arg Leu Ser His  Pro Glu Trp
    1160                 1165                 1170
```

```
Ser Ser  Gly Tyr Tyr Trp Ile  Asp Pro Asn Gln Gly  Cys Thr Met
    1175                 1180                 1185

Asp Ala  Ile Lys Val Tyr Cys  Asp Phe Ser Thr Gly  Glu Thr Cys
    1190                 1195                 1200

Ile Arg  Ala Gln Pro Glu Asn  Ile Pro Ala Lys Asn  Trp Tyr Arg
    1205                 1210                 1215

Ser Ser  Lys Asp Lys Lys His  Val Trp Leu Gly Glu  Thr Ile Asn
    1220                 1225                 1230

Ala Gly  Ser Gln Phe Glu Tyr  Asn Val Glu Gly Val  Thr Ser Lys
    1235                 1240                 1245

Glu Met  Ala Thr Gln Leu Ala  Phe Met Arg Leu Leu  Ala Asn Tyr
    1250                 1255                 1260

Ala Ser  Gln Asn Ile Thr Tyr  His Cys Lys Asn Ser  Ile Ala Tyr
    1265                 1270                 1275

Met Asp  Glu Glu Thr Gly Asn  Leu Lys Lys Ala Val  Ile Leu Gln
    1280                 1285                 1290

Gly Ser  Asn Asp Val Glu Leu  Val Ala Glu Gly Asn  Ser Arg Phe
    1295                 1300                 1305

Thr Tyr  Thr Val Leu Val Asp  Gly Cys Ser Lys Lys  Thr Asn Glu
    1310                 1315                 1320

Trp Gly  Lys Thr Ile Ile Glu  Tyr Lys Thr Asn Lys  Pro Ser Arg
    1325                 1330                 1335

Leu Pro  Phe Leu Asp Ile Ala  Pro Leu Asp Ile Gly  Gly Ala Asp
    1340                 1345                 1350

Gln Glu  Phe Phe Val Asp Ile  Gly Pro Val Cys Phe  Lys
    1355                 1360                 1365
```

<210> SEQ ID NO 4
<211> LENGTH: 4100
<212> TYPE: DNA
<213> ORGANISM: Homo sapiens

<400> SEQUENCE: 4

```
atgctcagct ttgtggatac gcggactttg ttgctgcttg cagtaacctt atgcctagca     60

acatgccaat ctttacaaga ggaaactgta agaaagggcc cagccggaga tagaggacca    120

cgtggagaaa ggggtccacc aggcccccca ggcagagatg gtgaagatgg tcccacaggc    180

cctcctggtc cacctggtcc tcctggcccc cctggtctcg gtgggaactt tgctgctcag    240

tatgatggaa aaggagttgg acttggccct ggaccaatgg gcttaatggg acctagaggc    300

ccacctggtg cagctggagc cccaggccct caaggtttcc aaggacctgc tggtgagcct    360

ggtgaacctg gtcaaactgg tcctgcaggt gctcgtggtc cagctggccc tcctggcaag    420

gctggtgaag atggtcaccc tggaaaaccc ggacgacctg gtgagagagg agttgttgga    480

ccacagggtg ctcgtggttt ccctggaact cctggacttc ctggcttcaa aggcattagg    540

ggacacaatg gtctggatgg attgaaggga cagcccggtg ctcctggtgt gaagggtgaa    600

cctggtgccc ctggtgaaaa tggaactcca ggtcaaacag gagcccgtgg gcttcctggt    660

gagagaggac gtgttggtgc ccctggccca gctggtgccc gtggcagtga tggaagtgtg    720

ggtcccgtgg gtcctgctgg tcccattggg tctgctggcc ctccaggctt cccaggtgcc    780

cctggcccca agggtgaaat tggagctgtt ggtaacgctg gtcctgctgg tcccgccggt    840

ccccgtggtg aagtgggtct tccaggcctc tccggccccg ttggacctcc tggtaatcct    900

ggagcaaacg gccttactgg tgccaagggt gctgctggcc ttcccggcgt tgctggggct    960
```

-continued

```
cccggcctcc ctggaccccg cggtattcct ggccctgttg gtgctgccgg tgctactggt   1020
gccagaggac ttgttggtga gcctggtcca gctggctcca aaggagagag cggtaacaag   1080
ggtgagcccg gctctgctgg gccccaaggt cctcctggtc ccagtggtga agaaggaaag   1140
agaggcccta atggggaagc tggatctgcc ggccctccag gacctcctgg gctgagaggt   1200
agtcctggtt ctcgtggtct tcctggagct gatggcagag ctggcgtcat gggccctcct   1260
ggtagtcgtg gtgcaagtgg ccctgctgga gtccgaggac ctaatggaga tgctggtcgc   1320
cctggggagc ctggtctcat gggacccaga ggtcttcctg gttcccctgg aaatatcggc   1380
cccgctggaa aagaaggtcc tgtcggcctc cctggcatcg acggcaggcc tggcccaatt   1440
ggcccagctg gagcaagagg agagcctggc aacattggat tccctggacc caaaggcccc   1500
actggtgatc ctggcaaaaa cggtgataaa ggtcatgctg gtcttgctgg tgctcggggt   1560
gctccaggtc ctgatggaaa caatggtgct cagggacctc ctggaccaca gggtgttcaa   1620
ggtggaaaag gtgaacaggg tcccgctggt cctccaggct tccagggtct gcctggcccc   1680
tcaggtcccg ctggtgaagt tggcaaacca ggagaaaggg gtctccatgg tgagtttggt   1740
ctccctggtc ctgctggtcc aagaggggaa cgcggtcccc caggtgagag tggtgctgcc   1800
ggtcctactg gtcctattgg aagccgaggt ccttctggac cccagggccc tgatggaaac   1860
aagggtgaac ctggtgtggt tggtgctgtg ggcactgctg gtccatctgg tcctagtgga   1920
ctcccaggag agaggggtgc tgctggcata cctggaggca agggagaaaa gggtgaacct   1980
ggtctcagag gtgaaattgg taaccctggc agagatggtg ctcgtggtgc tcctggtgct   2040
gtaggtgccc ctggtcctgc tggagccaca ggtgaccggg gcgaagctgg ggctgctggt   2100
cctgctggtc ctgctggtcc tcggggaagc cctggtgaac gtggtgaggt cggtcctgct   2160
ggccccaatg gatttgctgg tcctgctggt gctgctggtc aacctggtgc taaaggagaa   2220
agaggagcca aagggcctaa gggtgaaaac ggtgttgttg gtcccacagg ccccgttgga   2280
gctgctggcc cagctggtcc aaatggtccc cccggtcctg ctggaagtcg tggtgatgga   2340
ggcccccctg gtatgactgg tttccctggt gctgctggac ggactggtcc cccaggaccc   2400
tctggtattt ctggccctcc tggtcccccct ggtcctgctg ggaaagaagg gcttcgtggt   2460
cctcgtggtg accaaggtcc agttggccga actggagaag taggtgcagt tggtcccccct   2520
ggcttcgctg gtgagaaggg tccctctgga gaggctggta ctgctggacc tcctggcact   2580
ccaggtcctc agggtcttct tggtgctcct ggtattctgg gtctccctgg ctcgagaggt   2640
gaacgtggtc taccaggtgt tgctggtgct gtgggtgaac ctggtcctct tggcattgcc   2700
ggccctcctg ggcccgtgg tcctcctggt gctgtgggta gtcctggagt caacggtgct   2760
cctggtgaag ctggtcgtga tggcaaccct gggaacgatg gtcccccagg tcgcgatggt   2820
caacccggac acaagggaga gcgcggttac cctggcaata ttggtcccgt tggtgctgca   2880
ggtgcacctg gtcctcatgg ccccgtgggt cctgctggca aacatggaaa ccgtggtgaa   2940
actggtcctt ctggtcctgt tggtcctgct ggtgctgttg gcccaagagg tcctagtggc   3000
ccacaaggca ttcgtggcga taagggagag cccggtgaaa aggggcccag aggtcttcct   3060
ggcttaaagg gacacaatgg attgcaaggt ctgcctggta tcgctggtca ccatggtgat   3120
caaggtgctc ctggctccgt gggtcctgct ggtcctaggg gccctgctgg tccttctggc   3180
cctgctggaa aagatggtcg cactggacat cctggtacag ttggacctgc tggcattcga   3240
ggccctcagg gtcaccaagg ccctgctggc ccccctggtc cccctggccc tcctggacct   3300
ccaggtgtaa gcggtggtgg ttatgacttt ggttacgatg gagacttcta cagggctgac   3360
```

```
cagcctcgct cagcaccttc tctcagaccc aaggactatg aagttgatgc tactctgaag   3420

tctctcaaca accagattga gacccttctt actcctgaag gctctagaaa gaacccagct   3480

cgcacatgcc gtgacttgag actcagccac ccagagtgga gcagtggtta ctactggatt   3540

gaccctaacc aaggatgcac tatggatgct atcaaagtat actgtgattt ctctactggc   3600

gaaacctgta tccgggccca acctgaaaac atcccagcca agaactggta taggagctcc   3660

aaggacaaga aacacgtctg gctaggagaa actatcaatg ctggcagcca gtttgaatat   3720

aatgtagaag gagtgacttc caaggaaatg gctacccaac ttgccttcat gcgcctgctg   3780

gccaactatg cctctcagaa catcacctac cactgcaaga acagcattgc atacatggat   3840

gaggagactg gcaacctgaa aaaggctgtc attctacagg gctctaatga tgttgaactt   3900

gttgctgagg gcaacagcag gttcacttac actgttcttg tagatggctg ctctaaaaag   3960

acaaatgaat ggggaaagac aatcattgaa tacaaaacaa ataagccatc acgcctgccc   4020

ttccttgata ttgcaccttt ggacatcggt ggtgctgacc aggaattctt tgtggacatt   4080

ggcccagtct gtttcaaata                                               4100
```

<210> SEQ ID NO 5
<211> LENGTH: 257
<212> TYPE: PRT
<213> ORGANISM: Homo sapiens

<400> SEQUENCE: 5

```
Met Ser Ile Leu Phe Tyr Val Ile Phe Leu Ala Tyr Leu Arg Gly Ile
1               5                   10                  15

Gln Gly Asn Asn Met Asp Gln Arg Ser Leu Pro Glu Asp Ser Leu Asn
            20                  25                  30

Ser Leu Ile Ile Lys Leu Ile Gln Ala Asp Ile Leu Lys Asn Lys Leu
        35                  40                  45

Ser Lys Gln Met Val Asp Val Lys Glu Asn Tyr Gln Ser Thr Leu Pro
    50                  55                  60

Lys Ala Glu Ala Pro Arg Glu Pro Glu Arg Gly Gly Pro Ala Lys Ser
65                  70                  75                  80

Ala Phe Gln Pro Val Ile Ala Met Asp Thr Glu Leu Leu Arg Gln Gln
                85                  90                  95

Arg Arg Tyr Asn Ser Pro Arg Val Leu Leu Ser Asp Ser Thr Pro Leu
            100                 105                 110

Glu Pro Pro Pro Leu Tyr Leu Met Glu Asp Tyr Val Gly Ser Pro Val
        115                 120                 125

Val Ala Asn Arg Thr Ser Arg Arg Lys Arg Tyr Ala Glu His Lys Ser
    130                 135                 140

His Arg Gly Glu Tyr Ser Val Cys Asp Ser Glu Ser Leu Trp Val Thr
145                 150                 155                 160

Asp Lys Ser Ser Ala Ile Asp Ile Arg Gly His Gln Val Thr Val Leu
                165                 170                 175

Gly Glu Ile Lys Thr Gly Asn Ser Pro Val Lys Gln Tyr Phe Tyr Glu
            180                 185                 190

Thr Arg Cys Lys Glu Ala Arg Pro Val Lys Asn Gly Cys Arg Gly Ile
        195                 200                 205

Asp Asp Lys His Trp Asn Ser Gln Cys Lys Thr Ser Gln Thr Tyr Val
    210                 215                 220

Arg Ala Leu Thr Ser Glu Asn Asn Lys Leu Val Gly Trp Arg Trp Ile
225                 230                 235                 240
```

-continued

```
Arg Ile Asp Thr Ser Cys Val Cys Ala Leu Ser Arg Lys Ile Gly Arg
                245                 250                 255

Thr


<210> SEQ ID NO 6
<211> LENGTH: 774
<212> TYPE: DNA
<213> ORGANISM: Homo sapiens

<400> SEQUENCE: 6

atgtccatct tgttttatgt gatatttctc gcttatctcc gtggcatcca aggtaacaac     60

atggatcaaa ggagtttgcc agaagactcg ctcaattccc tcattattaa gctgatccag    120

gcagatattt tgaaaaacaa gctctccaag cagatggtgg acgttaagga aaattaccag    180

agcaccctgc ccaaagctga ggctccccga gagccggagc ggggagggcc cgccaagtca    240

gcattccagc cagtgattgc aatggacacc gaactgctgc gacaacagag acgctacaac    300

tcaccgcggg tcctgctgag cgacagcacc cccttggagc cccgcccctt gtatctcatg    360

gaggattacg tgggcagccc cgtggtggcg aacagaacat cacggcggaa acggtacgcg    420

gagcataaga gtcaccgagg ggagtactcg gtatgtgaca gtgagagtct gtgggtgacc    480

gacaagtcat cggccatcga cattcgggga caccaggtca cggtgctggg ggagatcaaa    540

acgggcaact ctcccgtcaa acaatatttt tatgaaacgc gatgtaagga agccaggccg    600

gtcaaaaacg gttgcagggg tattgatgat aaacactgga actctcagtg caaaacatcc    660

caaacctacg tccgagcact gacttcagag aacaataaac tcgtgggctg gcggtggata    720

cggatagaca cgtcctgtgt gtgtgccttg tcgagaaaaa tcggaagaac atga          774
```